United States Patent
Ahn et al.

(10) Patent No.: US 10,388,889 B2
(45) Date of Patent: Aug. 20, 2019

(54) SUBSTITUTED PHOSPHINES AS COMPONENTS OF ORGANIC LIGHT-EMITTING DEVICES

(71) Applicant: SAMSUNG DISPLAY CO., LTD., Yongin-si, Gyeonggi-do (KR)

(72) Inventors: Heechoon Ahn, Yongin-si (KR); Soobyung Ko, Yongin-si (KR); Mieun Jun, Yongin-si (KR); Youngkook Kim, Yongin-si (KR); Seokhwan Hwang, Yongin-si (KR)

(73) Assignee: SAMSUNG DISPLAY CO., LTD., Yongin-si, Gyeonggi-do (KR)

( * ) Notice: Subject to any disclaimer, the term of this patent is extended or adjusted under 35 U.S.C. 154(b) by 0 days.

(21) Appl. No.: 15/634,392

(22) Filed: Jun. 27, 2017

(65) Prior Publication Data

US 2018/0026206 A1    Jan. 25, 2018

(30) Foreign Application Priority Data

Jul. 25, 2016 (KR) .................. 10-2016-0094145

(51) Int. Cl.
| | | |
|---|---|---|
| C07F 9/28 | (2006.01) | |
| H01L 51/00 | (2006.01) | |
| C07F 9/64 | (2006.01) | |
| C09K 11/02 | (2006.01) | |
| H01L 51/50 | (2006.01) | |
| H01L 51/52 | (2006.01) | |

(52) U.S. Cl.
CPC ............ *H01L 51/0072* (2013.01); *C07F 9/64* (2013.01); *C09K 11/025* (2013.01); *H01L 51/0067* (2013.01); *H01L 51/5012* (2013.01); *H01L 51/5016* (2013.01); *H01L 51/5206* (2013.01); *H01L 51/5221* (2013.01)

(58) Field of Classification Search
CPC ......................................................... C07F 9/28
USPC ........................................................... 568/14
See application file for complete search history.

(56) References Cited

U.S. PATENT DOCUMENTS

| 8,722,208 B2 | 5/2014 | Kai et al. |
| 2010/0253212 A1 | 10/2010 | Cheng et al. |
| 2014/0070146 A1 | 3/2014 | Parham et al. |

FOREIGN PATENT DOCUMENTS

| KR | 10-2011-0129421 A | 12/2011 |
| KR | 10-2012-0020901 A | 3/2012 |
| KR | 10-2014-0045368 A | 4/2014 |
| KR | 10-2016-0123 | * 10/2016 |

* cited by examiner

*Primary Examiner* — Douglas M Willis
(74) *Attorney, Agent, or Firm* — Lee & Morse, P.C.

(57) ABSTRACT

A heterocyclic compound and an organic light emitting device, the compound being represented by Formula 1:

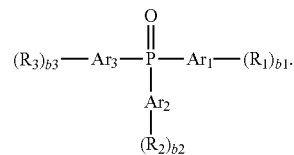

Formula 1

19 Claims, 4 Drawing Sheets

| 190 |
|-----|
| 150 |
| 110 |

| 190 |
|---|
| 150 |
| 110 |
| 210 |

| 220 |
|---|
| 190 |
| 150 |
| 110 |

| 220 |
|-----|
| 190 |
| 150 |
| 110 |
| 210 |

SUBSTITUTED PHOSPHINES AS COMPONENTS OF ORGANIC LIGHT-EMITTING DEVICES

CROSS-REFERENCE TO RELATED APPLICATION

Korean Patent Application No. 10-2016-0094145, filed on Jul. 25, 2016, in the Korean Intellectual Property Office, and entitled: "Heterocyclic Compound and Organic Light-Emitting Device Including the Same," is incorporated by reference herein in its entirety.

BACKGROUND

1. Field

Embodiments relate to a heterocyclic compound and an organic light-emitting device including the same.

2. Description of the Related Art

Organic light-emitting devices are self-emission devices that have relatively wide viewing angles, relatively high contrast ratios, relatively short response times, and increased luminance, driving voltage, and response speed characteristics. Organic light-emitting devices may produce full-color images.

Organic light-emitting devices may include a first electrode on a substrate. Organic light-emitting devices may include a hole transport region, an emission layer, an electron transport region, and a second electrode sequentially on the first electrode. Holes provided from the first electrode may move toward the emission layer through the hole transport region. Electrons provided from the second electrode may move toward the emission layer through the electron transport region. Carriers, such as holes and electrons, may recombine in the emission layer to produce excitons. The excitons may transition from an excited state to a ground state, thereby generating light.

SUMMARY

Embodiments are directed to a heterocyclic compound and an organic light-emitting device including the same.

The embodiments may be realized by providing a heterocyclic compound represented by Formula 1:

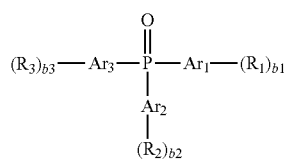

Formula 1 wherein, in Formula 1, $Ar_1$ to $Ar_3$ are each independently a substituted or unsubstituted $C_5$-$C_{60}$ carbocyclic group or a substituted or unsubstituted $C_2$-$C_{60}$ heterocyclic group, two adjacent groups of $Ar_1$ to $Ar_3$ are separate or are bound to form a substituted or unsubstituted $C_5$-$C_{60}$ carbocyclic group or a substituted or unsubstituted $C_2$-$C_{60}$ heterocyclic group, $R_1$ to $R_3$ are each independently represented by the following Formula 2, b1 to b3 are each independently an integer of 0 to 3, b1 to b3 satisfy b1+b2+b3≥1; or when $Ar_1$ to $Ar_3$ are each a substituted or unsubstituted benzene group, b1+b2+b3≥2,

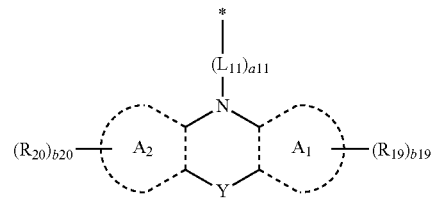

Formula 2 wherein, in Formula 2, $A_1$ and $A_2$ are each independently a benzene group, a naphthalene group, a phenanthrene group, a fluoranthene group, a triphenylene group, a pyrene group, a chrysene group, a pyridine group, or a pyrimidine group, $L_{11}$ is a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, or a substituted or unsubstituted divalent non-aromatic condensed heteropolycyclic group, a11 is an integer of 0 to 3; when a11 is 2 or 3, the 2 or 3 $L_{11}$(s) are identical to or different from each other, Y is $C(R_{17})(R_{18})$, sulfur (S), $Si(R_{17})(R_{18})$, S(=O), S(=O)$_2$, or P(=O)($R_{17}$), $R_{17}$ to $R_{20}$ are each independently hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —S(=O)($Q_1$), or —P(=O)($Q_1$)($Q_2$), b19 and b20 are each independently an integer of 0 to 8, wherein, in Formulae 1 and 2, at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, or a $C_1$-$C_{60}$ alkoxy group; a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si$(Q_{11})(Q_{12})(Q_{13})$, —N$(Q_{11})(Q_{12})$, —B$(Q_{11})(Q_{12})$, —C(=O)$(Q_{11})$, —S(=O)$_2$$(Q_{11})$, or —P(=O)$(Q_{11})(Q_{12})$; a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group; a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si$(Q_{21})(Q_{22})(Q_{23})$, —N$(Q_{21})(Q_{22})$, —B$(Q_{21})(Q_{22})$, —C(=O)$(Q_{21})$, —S(=O)$_2$$(Q_{21})$, or —P(=O)$(Q_{21})(Q_{22})$; or —Si$(Q_{31})(Q_{32})(Q_{33})$, —N$(Q_{31})(Q_{32})$, —B$(Q_{31})(Q_{32})$, —C(=O)$(Q_{31})$, —S(=O)$_2$$(Q_{31})$, and —P(=O)$(Q_{31})(Q_{32})$, wherein $Q_1$, $Q_2$, $Q_{11}$ to $Q_{13}$, $Q_{21}$ to $Q_{23}$, and $Q_{31}$ to $Q_{33}$ are each independently hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, or a terphenyl group, and * indicates a binding site to an adjacent atom.

The embodiments may be realized by providing an organic light emitting device including a first electrode; a second electrode facing the first electrode; and an organic layer between the first electrode and the second electrode, wherein the organic layer includes an emission layer, and wherein the organic layer includes the heterocyclic compound according to an embodiment.

BRIEF DESCRIPTION OF THE DRAWINGS

Features will be apparent to those of skill in the art by describing in detail exemplary embodiments with reference to the attached drawings in which:

FIG. 1 illustrates a schematic cross-sectional view of an organic light-emitting device according to an embodiment;

FIG. 2 illustrates a schematic cross-sectional view of an organic light-emitting device according to an embodiment;

FIG. 3 illustrates a schematic cross-sectional view of an organic light-emitting device according to an embodiment; and FIG. 4 illustrates a schematic cross-sectional view of an organic light-emitting device according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout.

As used herein, the terms "or" and "and/or" are not exclusive, and include any and all combinations of one or more of the associated listed items. Expressions such as "at least one of" when preceding a list of elements, modify the entire list of elements and do not modify the individual elements of the list.

A heterocyclic compound may be represented by Formula 1.

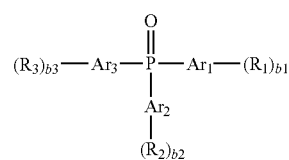

Formula 1

In Formula 1, $Ar_1$ to $Ar_3$ may each independently be or include, e.g., a substituted or unsubstituted $C_5$-$C_{60}$ carbocyclic group or a substituted or unsubstituted $C_2$-$C_{60}$ heterocyclic group. In an implementation, in Formula 1, at least two adjacent groups of $Ar_1$ to $Ar_3$ may be separate or may be bound to form a substituted or unsubstituted $C_5$-$C_{60}$ carbocyclic group or a substituted or unsubstituted $C_2$-$C_{60}$ heterocyclic group.

In an implementation, in Formula 1, $Ar_1$ to $Ar_3$ may each independently be selected from or include, e.g., a benzene group, a naphthalene group, a pyridine group, a pyrazine group, a pyrimidine group, a pyridazine group, a triazine group, a quinoline group, an isoquinoline group, a benzoquinoline group, a phthalazine group, a naphthyridine group, a quinoxaline group, and a quinazoline group; and a benzene group, a naphthalene group, a pyridine group, a pyrazine group, a pyrimidine group, a pyridazine group, a triazine group, a quinoline group, an isoquinoline group, a benzoquinoline group, a phthalazine group, a naphthyridine group, a quinoxaline group, and a quinazoline group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In an implementation, in Formula 1, $Ar_1$ to $Ar_3$ may each independently be selected from, e.g., a benzene group and a pyridine group; and a benzene group and a pyridine group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In an implementation, in Formula 1, at least one selected from $Ar_1$ to $Ar_3$ may be selected from, e.g., a substituted or unsubstituted π electron-depleted nitrogen-containing $C_2$-$C_{60}$ heterocyclic group.

In an implementation, in Formula 1, at least one selected from $Ar_1$ to $Ar_3$ may be selected from, e.g., a pyridine group, a pyrimidine group, a triazine group, a quinoline group, an isoquinoline group, a quinazoline group, and a quinoxaline group; and a pyridine group, a pyrimidine group, a triazine group, a quinoline group, an isoquinoline group, a quinazoline group, and a quinoxaline group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In Formula 1, b1 to b3 may each independently be, e.g., an integer of 0 to 3. In an implementation, b1 to b3 may each independently be, e.g., 0, 1, or 2.

In Formula 1, b1 to b3 may satisfy b1+b2+b3≥1. In an implementation, when $Ar_1$ to $Ar_3$ are each a substituted or unsubstituted benzene group, b1+b2+b3≥2.

In an implementation, when $Ar_1$ to $Ar_3$ are each a benzene group, b1 may be 2, b2 may be 0, and b3 may be 0. In an implementation, b1 may be 1, b2 may be 1, and b3 may be 0.

In Formula 1, $R_1$ to $R_3$ may each independently be a group represented by Formula 2.

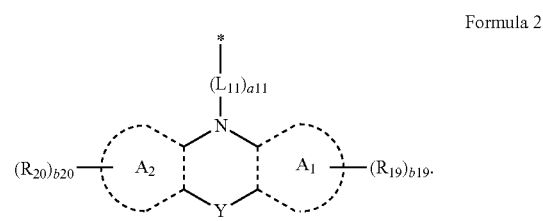

Formula 2

In Formula 2, $A_1$ and $A_2$ may each independently be selected from, e.g., a benzene group, a naphthalene group, a phenanthrene group, a fluoranthene group, a triphenylene group, a pyrene group, a chrysene group, a pyridine group, and a pyrimidine group.

In an implementation, in Formula 2, $A_1$ and $A_2$ may each independently be a benzene group.

In Formula 2, $L_{11}$ may be selected from or include, e.g., a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In an implementation, in Formula 2, $L_{11}$ may be selected from, e.g., a phenylene group, a pentalenylene group, an indenylene group, a naphthylene group, an azulenylene group, an indacenylene group, an acenaphthylene group, a fluorenylene group, a spiro-bifluorenylene group, a spiro-benzofluorene-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a perylenylene group, a pentacenylene group, a pyrrolylene group, a thiophenylene group, a furanylene group, a silolylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an indolylene group, an isoindolylene group, an indazolylene group, a purinylene group, a quinolinylene group, an isoquinolinylene group, a benzoquinolinylene group, a benzoisoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, a benzofuranylene group, a benzothiophenylene group, a benzosilolylene group, a benzothiazolylene group, an isobenzothiazolylene group, a benzoxazolylene group, an isobenzoxazolylene group, a triazolylene group, a tetrazolylene group, an oxadiazolylene group, a triazinylene group, a carbazolylene group, a dibenzofuranylene group, a dibenzothiophenylene group, a dibenzosilolylene group, a benzocarbazolylene group, a naphthobenzofuranylene group, a naphthobenzothiophenylene group, a naphthobenzosilolylene group, a dibenzocarbazolylene group, a dinaphthofuranylene group, a dinaphthothiophenylene group, a dinaphthosilolylene group a thiadiazolylene group, an imidazopyridinylene group, an imidazopyrimidinylene group, an oxazolopyridinylene group, a thiazolopyridinylene group, a benzonaphthyridinylene group, an azafluorenylene group, an azaspiro-bifluorenylene group, an azacarbazolylene group, an azadibenzofuranylene group, an azadibenzothiophenylene group, an azadibenzosilolylene group, an indenopyrrolylene group, an indolopyrrolylene group, an indenocarbazolylene group, and an indolocarbazolylene group; and a phenylene group, a pentalenylene group, an indenylene group, a naphthylene group, an azulenylene group, an indacenylene group, an acenaphthylene group, a fluorenylene group, a spiro-bifluorenylene group, a spiro-benzofluorene-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a perylenylene group, a pentacenylene group, a pyrrolylene group, a thiophenylene group, a furanylene group, a silolylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an indolylene group, an isoindolylene group, an indazolylene group, a purinylene group, a quinolinylene group, an isoquinolinylene group, a benzoquinolinylene group, a benzoisoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, a benzofuranylene group, a benzothiophenylene group, a benzosilolylene group, a benzothiazolylene group, an isobenzothiazolylene group, a benzoxazolylene group, an isobenzoxazolylene group, a triazolylene group, a tetrazolylene group, an oxadiazolylene group, a triazinylene group, a carbazolylene group, a dibenzofuranylene group, a dibenzothiophenylene group, a dibenzosilolylene group, a benzocarbazolylene group, a naphthobenzofuranylene group, a naphthobenzothiophenylene group, a naphthobenzosilolylene group, a dibenzocarbazolylene group, a dinaphthofuranylene group, a dinaphthothiophenylene group, a dinaphthosilolylene group, a thiadiazolylene group, an imidazopyridinylene group, an imidazopyrimidinylene group, an oxazolopyridinylene group, a thiazolopyridinylene group, a benzonaphthyridinylene group, an azafluorenylene group, an azaspiro-bifluorenylene group, an azacarbazolylene group, an azadibenzofuranylene group, an azadibenzothiophenylene group, an azadibenzosilolylene group, an indenopyrrolylene group, an indolopyrrolylene group, an indenocarbazolylene group, and an indolocarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{20}$ aryl group, a $C_1$-$C_{20}$ heteroaryl group, a monovalent non-aromatic condensed polycyclic group, a monovalent non-aromatic condensed heteropolycyclic group, a methylphenyl group, a biphenyl group, and —Si($Q_{31}$)($Q_{32}$)($Q_{33}$), wherein $Q_{31}$ to $Q_{33}$ may each independently be selected from, e.g., a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group.

In an implementation, in Formula 2, $L_{11}$ may be, e.g., a group represented by one of the following Formulae 3-1 to 3-46.

Formula 3-1
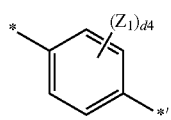
Formula 3-2
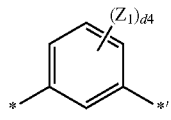
Formula 3-3
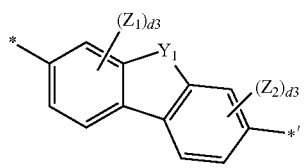
Formula 3-4
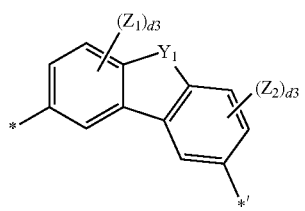
Formula 3-5
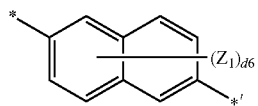
Formula 3-6
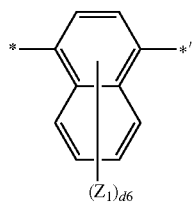
Formula 3-7
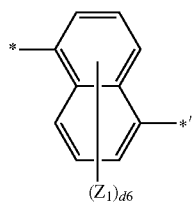
Formula 3-8
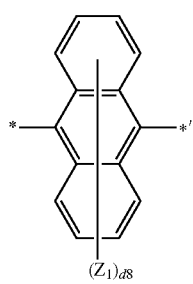
Formula 3-9
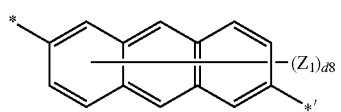
Formula 3-10
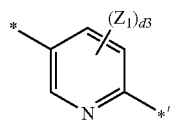
Formula 3-11
Formula 3-12
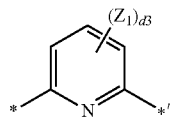
Formula 3-13
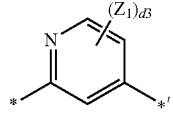
Formula 3-14
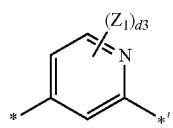
Formula 3-15
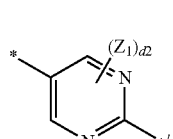
Formula 3-16
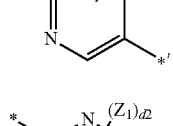
Formula 3-17
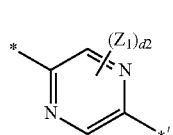
Formula 3-18
Formula 3-19
Formula 3-20
Formula 3-21
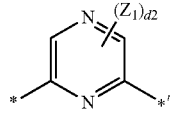

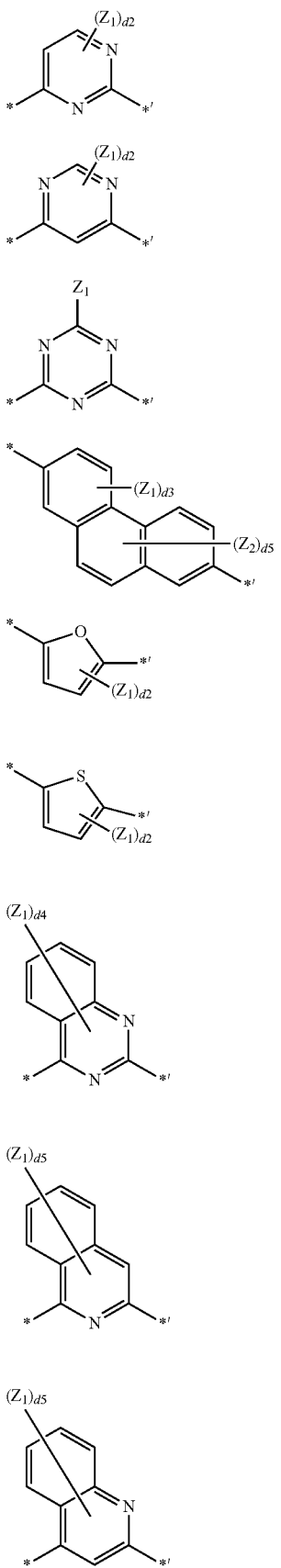
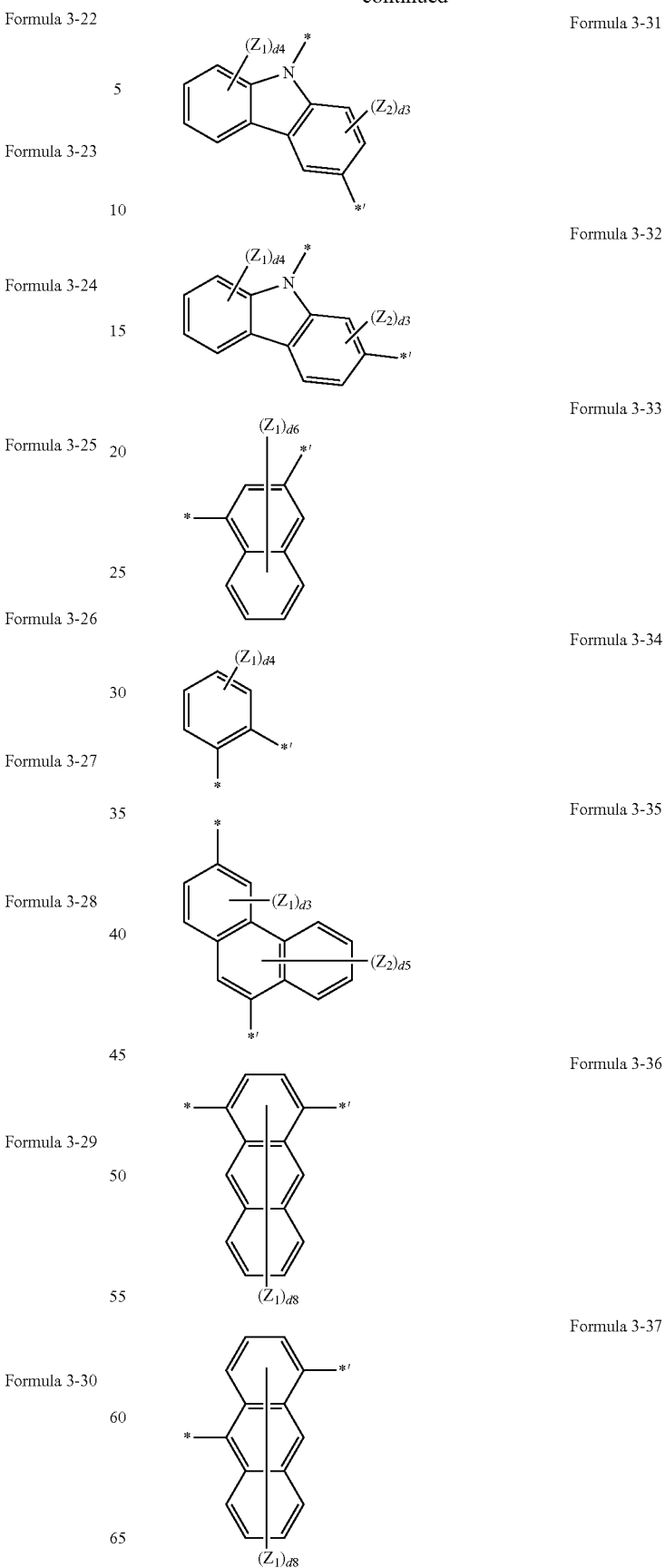

Formula 3-38

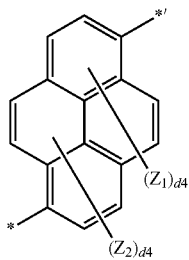

Formula 3-39

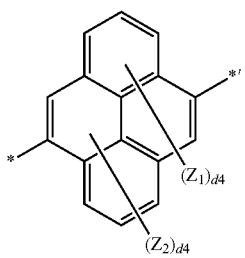

Formula 3-40

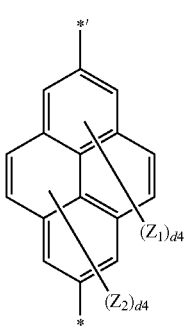

Formula 3-41

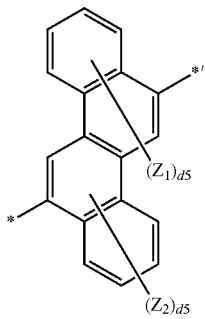

Formula 3-42

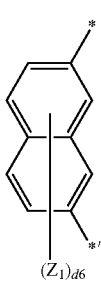

Formula 3-43

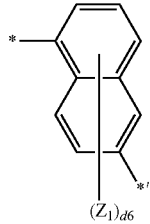

Formula 3-44

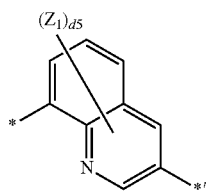

Formula 3-45

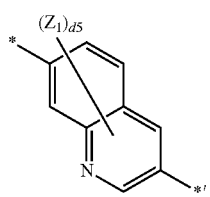

Formula 3-46

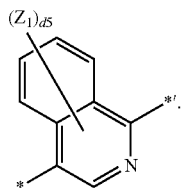

In Formulae 3-1 to 3-46, $Y_1$ may be selected from, e.g., oxygen (O), sulfur (S), $C(Z_3)(Z_4)$, $N(Z_5)$, and $Si(Z_6)(Z_7)$.

$Z_1$ to $Z_7$ may each independently be selected from, e.g., hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group, d2 may be 1 or 2,
d3 may be an integer of 1 to 3,
d4 may be an integer of 1 to 4,
d5 may be an integer of 1 to 5,
d6 may be an integer of 1 to 6, and
d8 may be an integer of 1 to 8.

In an implementation, $L_{11}$ may be a group represented by Formula 3-2, Formula 3-12, or Formula 3-31.

In Formula 2, a11 may be, e.g., an integer of 0 to 3. In an implementation, a11 may be 0, 1, or 2. In an implementation, a11 may be 0 or 1. When a11 is 2 or 3, the 2 or 3 $L_{11}$(s) may be identical to or different from each other.

In Formula 2, Y may be selected from, e.g., $C(R_{17})(R_{18})$, S, $Si(R_{17})(R_{18})$, $S(=O)$, $S(=O)_2$, and $P(=O)(R_{17})$.

In an implementation, in Formula 2, Y may be $C(R_{17})(R_{18})$ or $Si(R_{17})(R_{18})$, wherein $R_{17}$ and $R_{18}$ may each independently be selected from, e.g., hydrogen, deuterium, a methyl group, an ethyl group, an n-propyl group, an iso-propyl group, an n-butyl group, an iso-butyl group, a sec-butyl group, and a tert-butyl group.

In an implementation, in Formula 2, Y may be $C(R_{17})(R_{18})$, and $R_{17}$ and $R_{18}$ may each be, e.g., a methyl group.

In an implementation, in Formula 2, $R_{17}$ to $R_{20}$ may each independently be selected from or include, e.g., hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —S(=O)($Q_1$), and —P(=O)($Q_1$)($Q_2$).

In an implementation, in Formula 2, $R_{19}$ and $R_{20}$ may each independently be selected from, e.g., hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, a pyrimidinyl group, a pyrazinyl group, a quinolinyl group, an isoquinolinyl group, a quinoxalinyl group, and a quinazolinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, a pyrimidinyl group, a pyrazinyl group, a quinolinyl group, an isoquinolinyl group, a quinoxalinyl group, and a quinazolinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, a pyrimidinyl group, a pyrazinyl group, a quinolinyl group, an isoquinolinyl group, a quinoxalinyl group, a quinazolinyl group —Si($Q_{31}$)($Q_{32}$)($Q_{33}$), and —N($Q_{31}$)($Q_{32}$); and —P(=O)($Q_1$)($Q_2$) and —S(=O)($Q_1$), wherein $Q_1$ to $Q_2$ and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In an implementation, in Formula 2, $R_{19}$ and $R_{20}$ may each independently be selected from, e.g., hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, and a hydrazono group;

a phenyl group, a biphenyl group, a terphenyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a pyridinyl group, a pyrimidinyl group, a pyrazinyl group, a quinolinyl group, an isoquinolinyl group, a quinoxalinyl group, and a quinazolinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a pyridinyl group, a pyrimidinyl group, a pyrazinyl group, a quinolinyl group, an isoquinolinyl group, a quinoxalinyl group, and a quinazolinyl group; and —P(=O)($Q_1$)($Q_2$) and —S(=O)($Q_1$), wherein $Q_1$ to $Q_2$ and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In an implementation, in Formula 2, $R_{19}$ and $R_{20}$ may each independently be selected from, e.g., hydrogen, a cyano group, a $C_1$-$C_{20}$ alkyl group, a phenyl group, a carbazole group, —P(=O)($Q_1$)($Q_2$), and —S(=O)($Q_1$), and $Q_1$ and $Q_2$ may each be a phenyl group.

In an implementation, in Formula 2, b19 and b20 may each independently be, e.g., an integer of 0 to 8. In an implementation, b19 and b20 may each independently be, e.g., an integer of 0 to 4. In an implementation, b19 and b20 may each independently be, e.g., an integer of 0 to 2.

In an implementation, the heterocyclic compound represented by Formula 1 may be represented by Formula 1-1, and groups represented by Formula 2 may be represented by Formula 2-1.

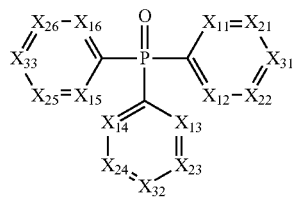

Formula 1-1

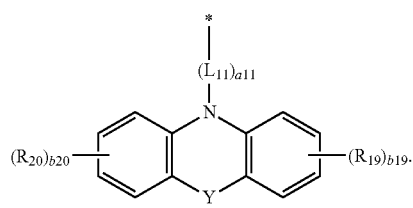

Formula 2-1

In Formula 1-1, $X_{11}$ may be nitrogen (N) or $C(R_{11})$, $X_{12}$ may be N or $C(R_{12})$, $X_{13}$ may be N or $C(R_{13})$, $X_{14}$ may be N or $C(R_{14})$, $X_{15}$ may be N or $C(R_{15})$, $X_{16}$ may be N or $C(R_{16})$, $X_{21}$ may be N or $C(R_{21})$, $X_{22}$ may be N or $C(R_{22})$, $X_{23}$ may be N or $C(R_{23})$, $X_{24}$ may be N or $C(R_{24})$, $X_{25}$ may be N or $C(R_{25})$, $X_{26}$ may be N or $C(R_{26})$, $X_{31}$ may be N or $C(R_{31})$, $X_{32}$ may be N or $C(R_{32})$, $X_{33}$ may be N or $C(R_{33})$, $R_{11}$ to $R_{16}$, $R_{21}$ to $R_{26}$, and $R_{31}$ to $R_{33}$ may each independently be selected from, e.g., a group represented by Formula 2-1, hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, when $X_{11}$ is $C(R_{11})$, $X_{12}$ is $C(R_{12})$, $X_{13}$ is $C(R_{13})$, $X_{14}$ is $C(R_{14})$, $X_{15}$ is $C(R_{15})$, $X_{16}$ is $C(R_{16})$, $X_{21}$ is $C(R_{21})$, $X_{22}$ is $C(R_{22})$, $X_{23}$ is $C(R_{23})$, $X_{24}$ is $C(R_{24})$, $X_{25}$ is $C(R_{25})$, $X_{26}$ is $C(R_{26})$, $X_{31}$ is $C(R_{31})$, $X_{32}$ is $C(R_{32})$, and $X_{33}$ is $C(R_{33})$, at least two selected from $R_{11}$, $R_{21}$, $R_{31}$, $R_{22}$, and $R_{12}$ may be a group represented by Formula 2-1, or at least one selected from $R_{11}$, $R_{21}$, $R_{31}$, and $R_{22}$, and at least one selected from $R_{12}$ and $R_{13}$, $R_{23}$, $R_{32}$, $R_{24}$, and $R_{14}$ may be a group represented by Formula 2-1, wherein $R_{12}$ and $R_{13}$, or $R_{14}$ and $R_{15}$ may be bound to form a substituted or unsubstituted $C_5$-$C_{60}$ carbocyclic group or a substituted or unsubstituted $C_2$-$C_{60}$ heterocyclic group, and in Formula 2-1, L, n, Y, $R_{19}$, $R_{20}$, b19, and b20 may be the same as those described above.

In an implementation, in Formula 1-1, at least one selected from $X_{11}$ to $X_{16}$ may be N, $X_{21}$ may be $C(R_{21})$, $X_{22}$ may be $C(R_{22})$, $X_{23}$ may be $C(R_{23})$, $X_{24}$ may be $C(R_{24})$, $X_{25}$ may be $C(R_{25})$, $X_{26}$ may be $C(R_{26})$, and at least one selected from $X_{21}$ to $X_{26}$ may be a group represented by Formula 2-1.

In an implementation, in Formula 1-1, at least one selected from $X_{11}$ to $X_{16}$ may be N, $X_{31}$ may be $C(R_{31})$, $X_{32}$ may be $C(R_{32})$, $X_{33}$ may be $C(R_{33})$, and at least one selected from $R_{31}$ to $R_{33}$ may be a group represented by Formula 2-1.

In an implementation, in Formula 1-1, at least one selected from $X_{11}$ to $X_{16}$ may be N, $X_{21}$ may be $C(R_{21})$, $X_{22}$ may be $C(R_{22})$, $X_{23}$ may be $C(R_{23})$, $X_{24}$ may be $C(R_{24})$, $X_{25}$ may be $C(R_{25})$, $X_{26}$ may be $C(R_{26})$, $X_{31}$ may be $C(R_{31})$, $X_{32}$ may be $C(R_{32})$, $X_{33}$ may be $C(R_{33})$, and at least one selected from $R_{21}$ to $R_{26}$ and $R_{31}$ to $R_{33}$ may be a group represented by Formula 2-1.

In an implementation, in Formula 1-1, at least one selected from $X_{21}$ to $X_{26}$ may be N, $X_{31}$ may be $C(R_{31})$, $X_{32}$ may be $C(R_{32})$, $X_{33}$ may be $C(R_{33})$, and at least one selected from $R_{31}$ to $R_{33}$ may be a group represented by Formula 2-1.

In an implementation, at least one selected from $X_{21}$ to $X_{26}$ may be N, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{31}$ may be $C(R_{31})$, $X_{32}$ may be $C(R_{32})$, $X_{33}$ may be $C(R_{33})$, and at least one selected from $R_{11}$ to $R_{16}$ and $R_{31}$ to $R_{33}$ may be a group represented by Formula 2-1.

In an implementation, in Formula 1-1, $X_{22}$ may be N, $X_{21}$ may be $C(R_{21})$, $X_{25}$ may be $C(R_{25})$, $X_{26}$ may be $C(R_{26})$, and at least one selected from $R_{21}$, $R_{25}$, and $R_{26}$ may be a group represented by Formula 2-1.

In an implementation, in Formula 1-1, at least one selected from $X_{31}$ to $X_{33}$ may be N, $X_{21}$ may be $C(R_{21})$, $X_{22}$ may be $C(R_{22})$, $X_{23}$ may be $C(R_{23})$, $X_{24}$ may be $C(R_{24})$, $X_{25}$ may be $C(R_{25})$, $X_{26}$ may be $C(R_{26})$, and at least one selected from $R_{21}$ to $R_{26}$ may be a group represented by Formula 2-1.

In an implementation, in Formula 1-1, at least one selected from $X_{31}$ to $X_{33}$ may be N, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{21}$ may be $C(R_{21})$, $X_{22}$ may be $C(R_{22})$, $X_{23}$ may be $C(R_{23})$, $X_{24}$ may be $C(R_{24})$, $X_{25}$ may be $C(R_{25})$, $X_{26}$ may be $C(R_{26})$, and at least one selected from $R_{11}$ to $R_{16}$ and $R_{21}$ to $R_{26}$ may be a group represented by Formula 2-1.

In an implementation, the heterocyclic compound represented by Formula 1 may be one of the following Compounds 1 to 77.

1

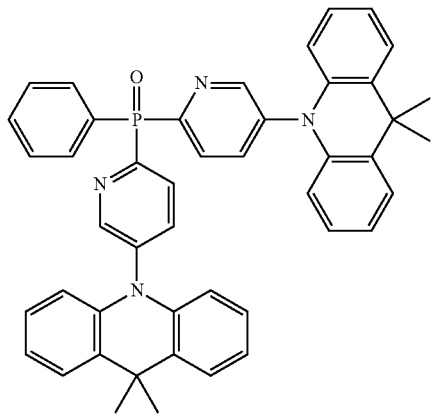

2

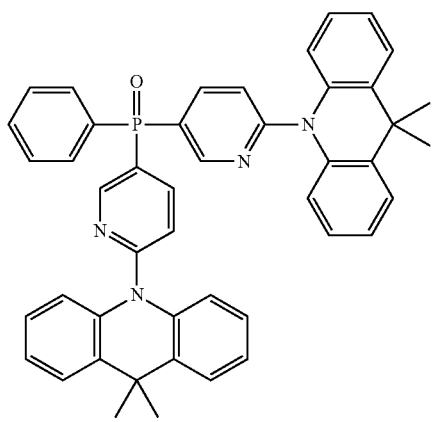

3

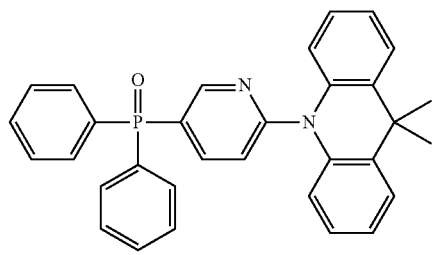

4

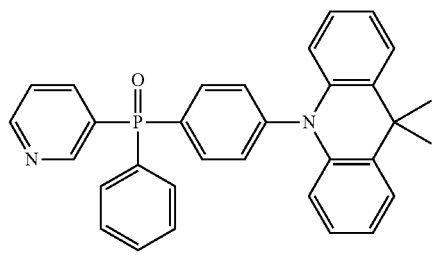

5

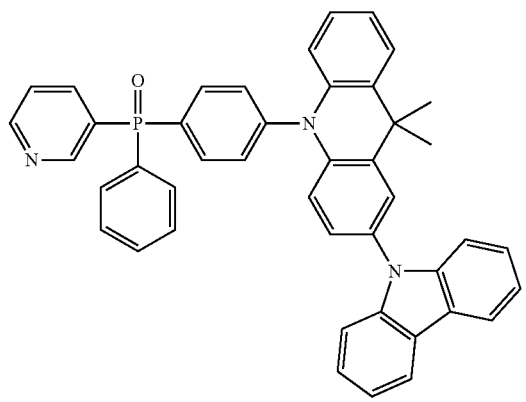

6

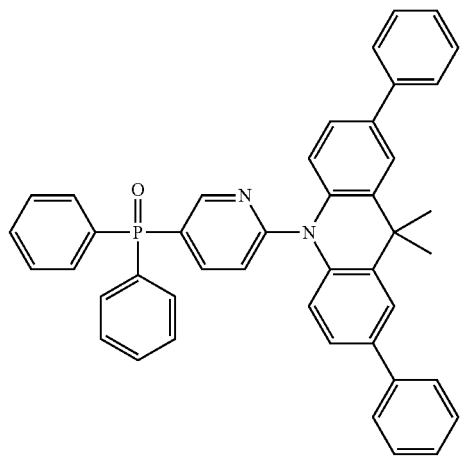

-continued
7
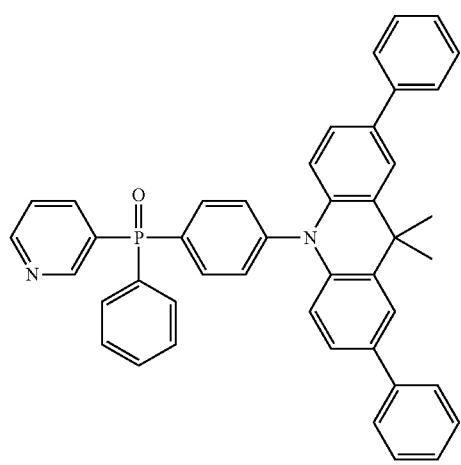
5
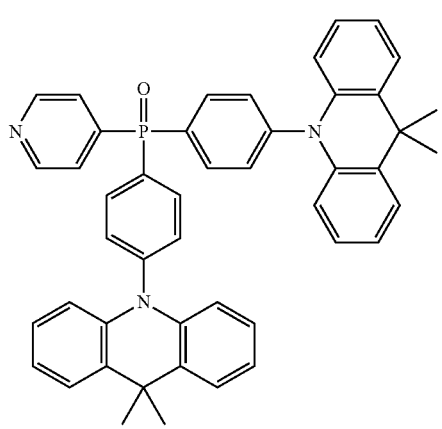
10
8
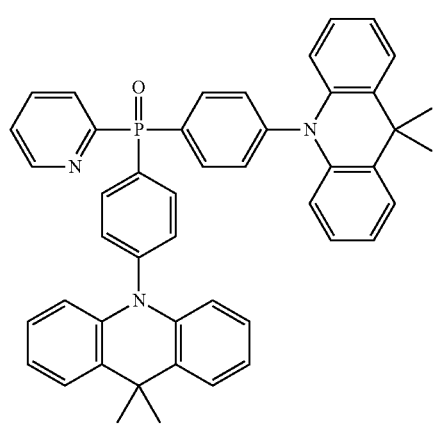
11
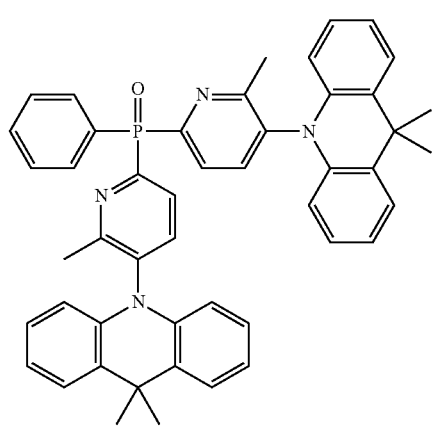
9
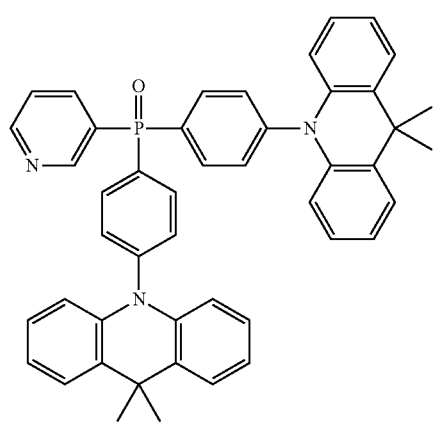
12
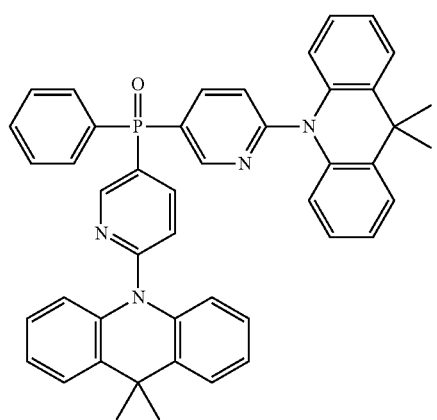

13
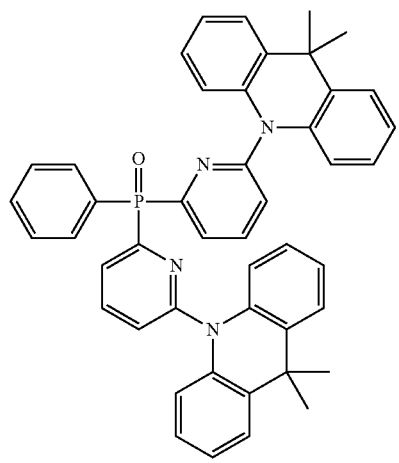
14
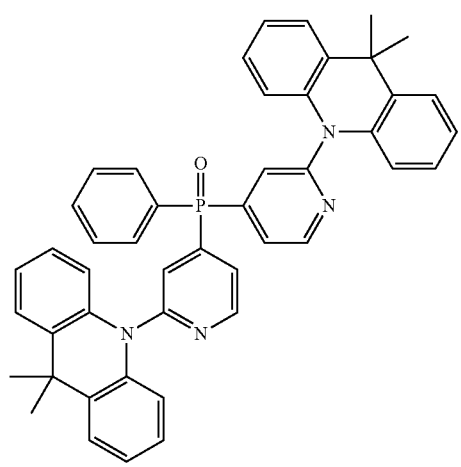
15
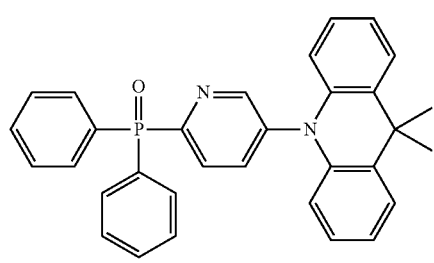
16
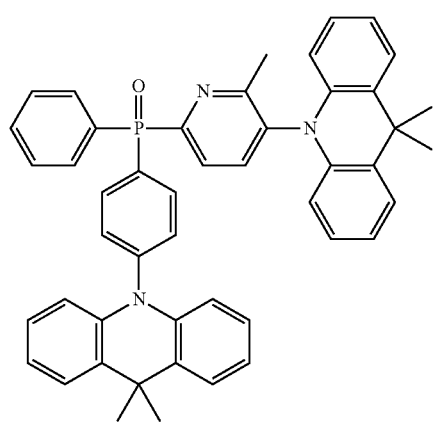
17
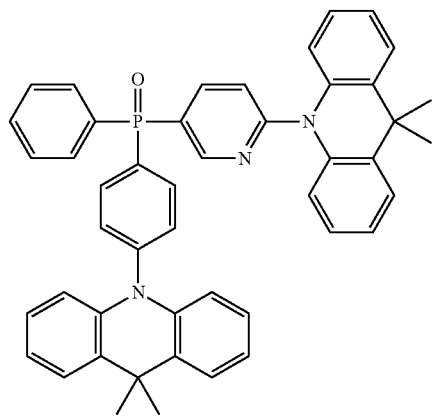
18
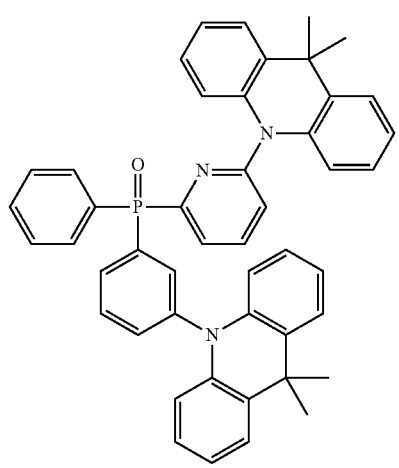
19
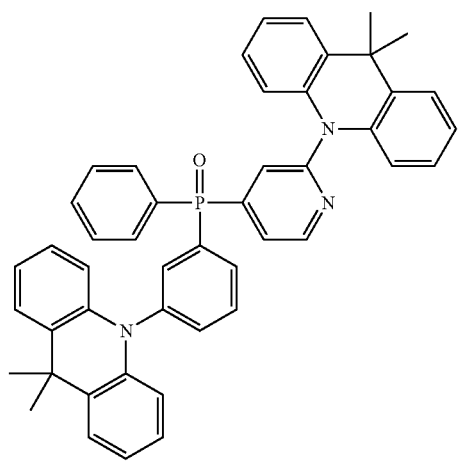
20

21
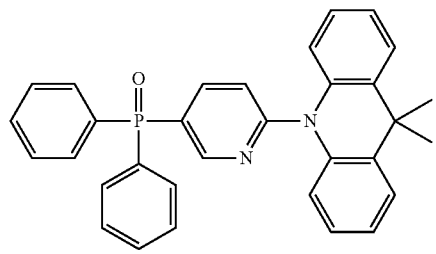
22
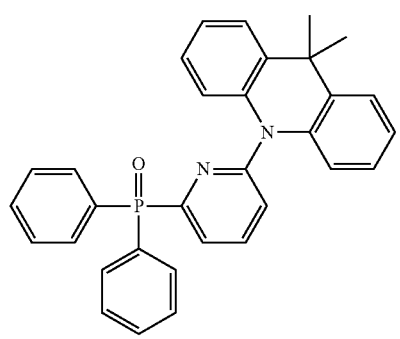
23
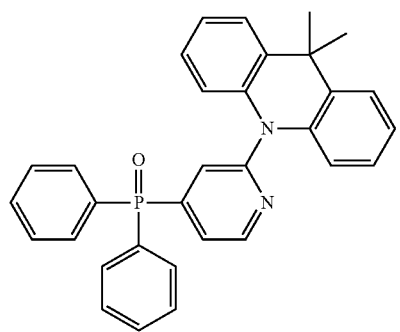
24
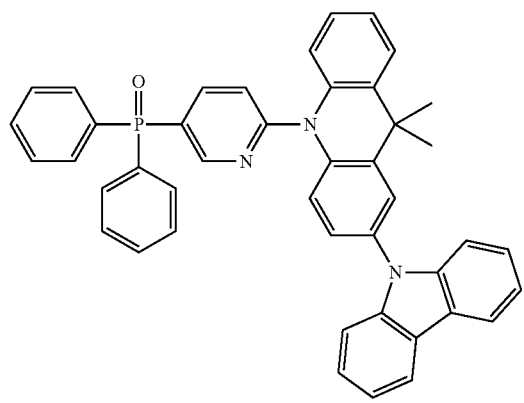
25
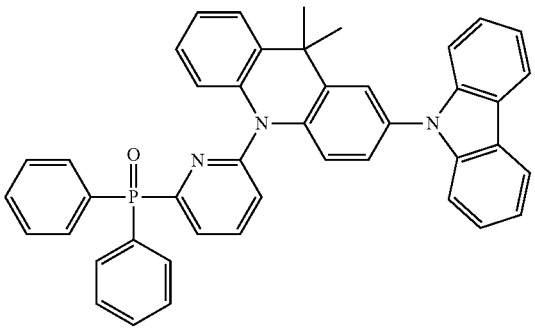
26
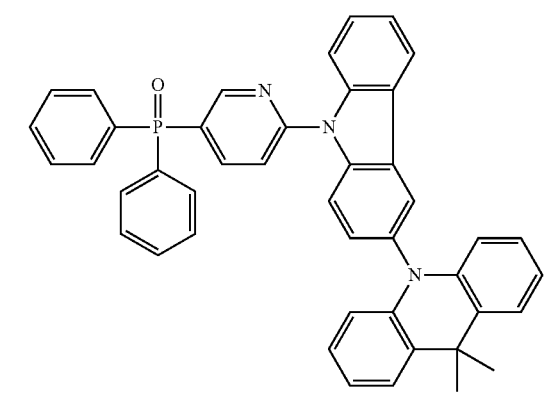
27
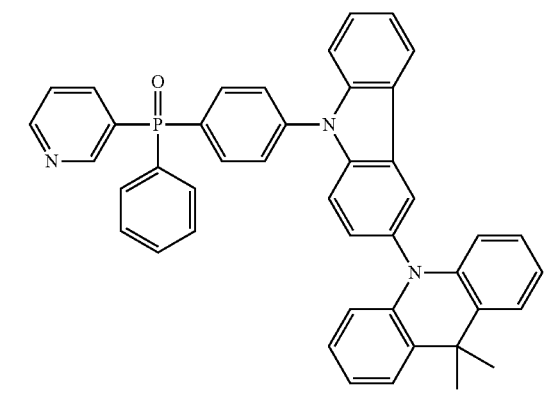
28
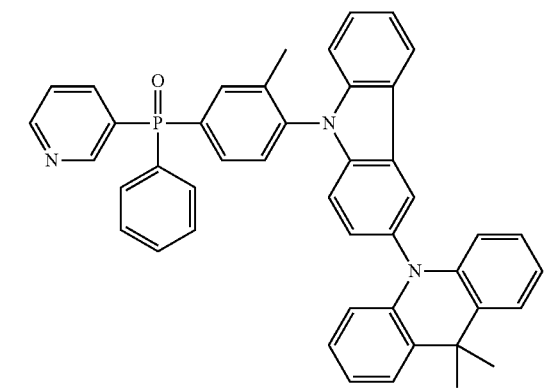

29
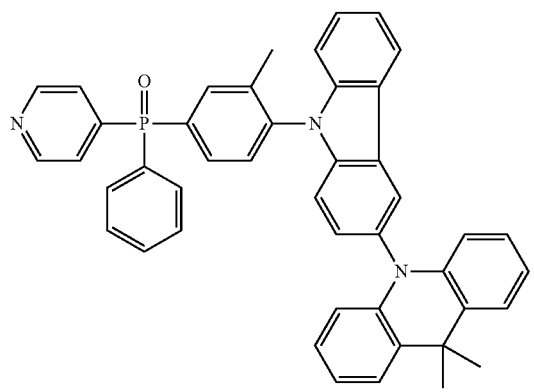
30
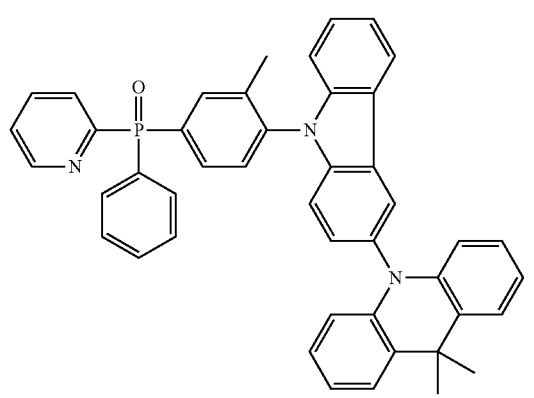
31
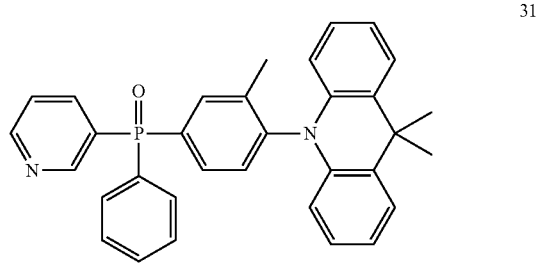
32
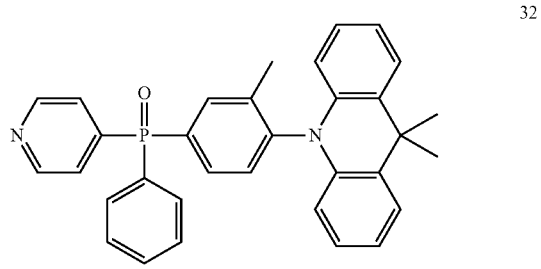
33
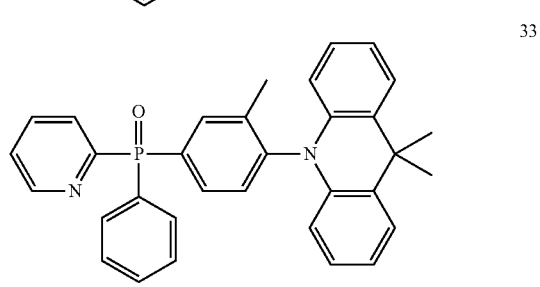
34
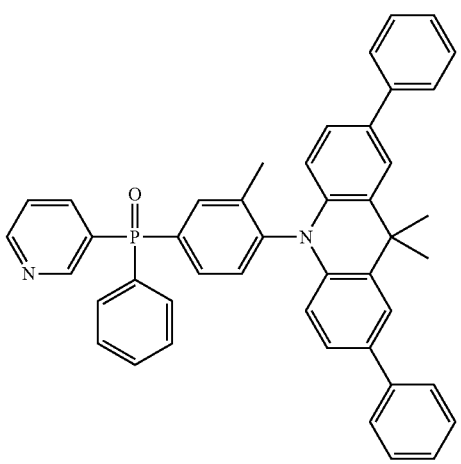
35
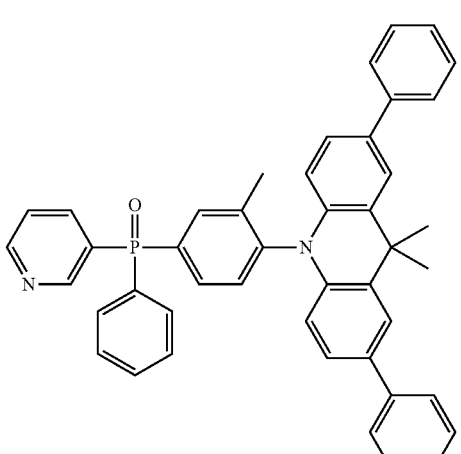
36
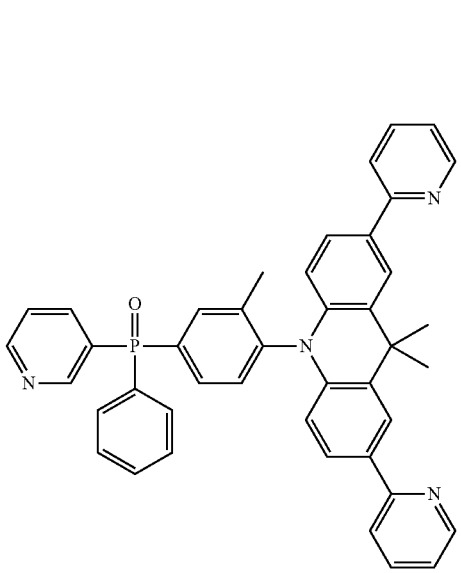

37
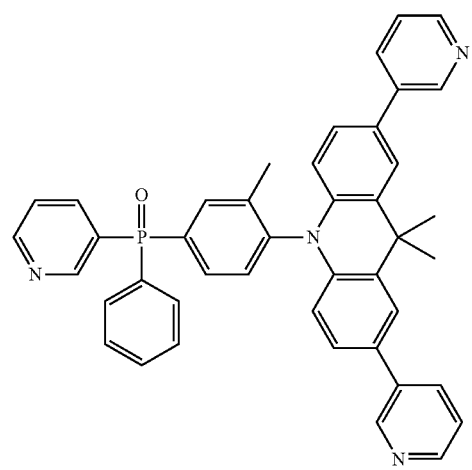
38
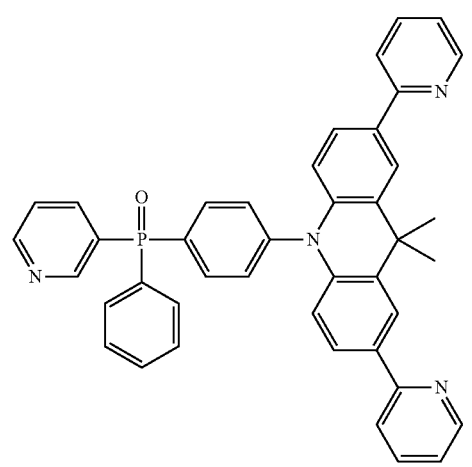
39
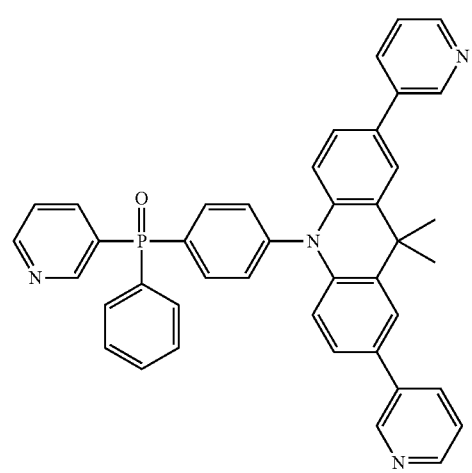
40
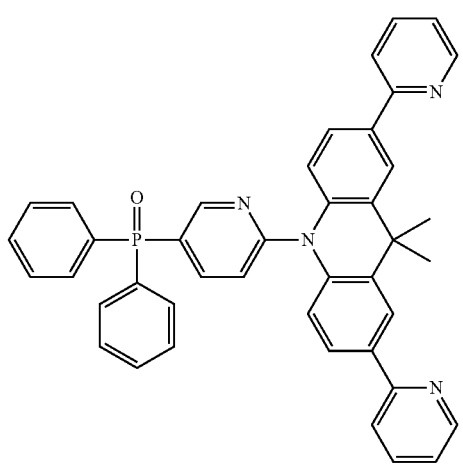
41
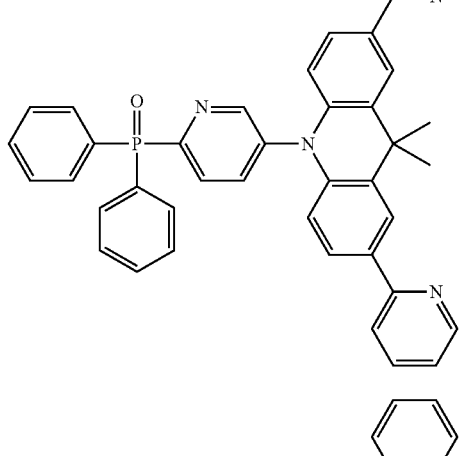
42
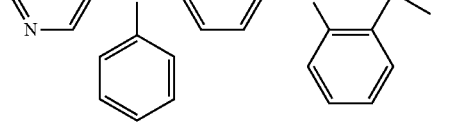
43
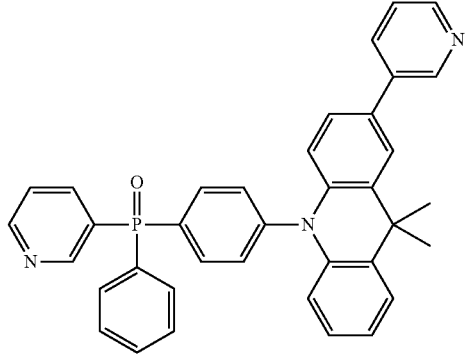

44
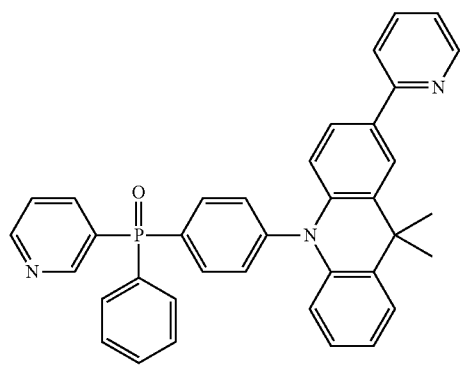
45
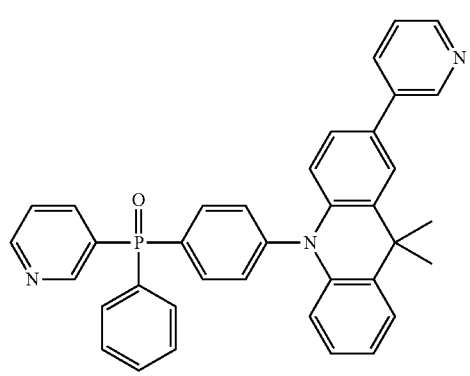
46
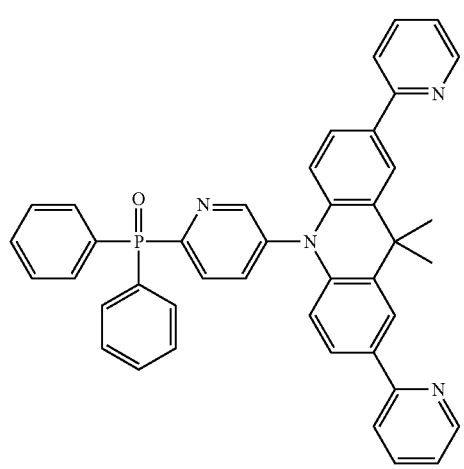
47
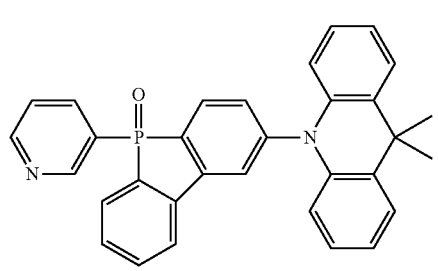
48
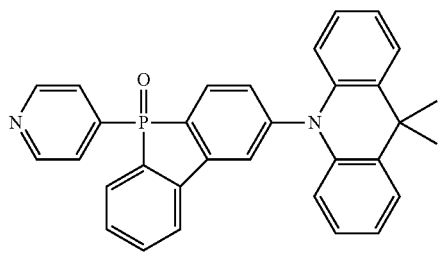
49
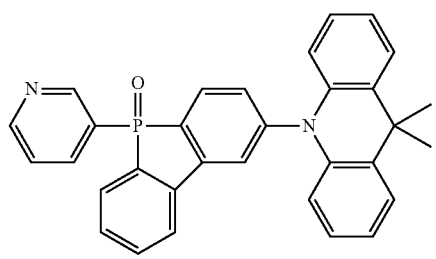
50
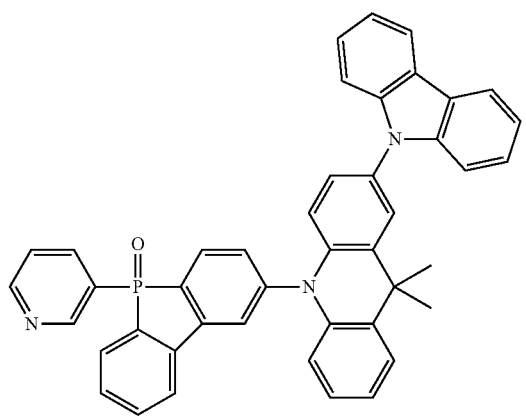
51
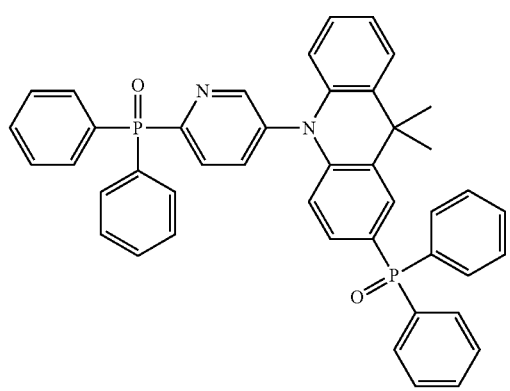

52
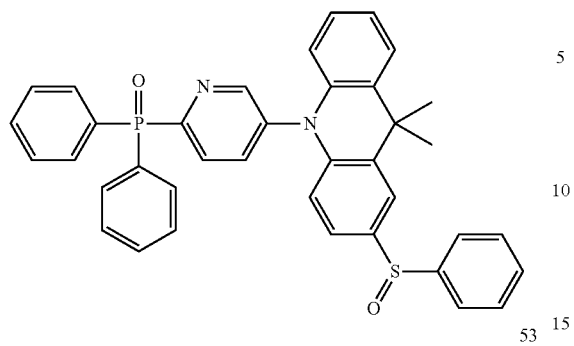
53
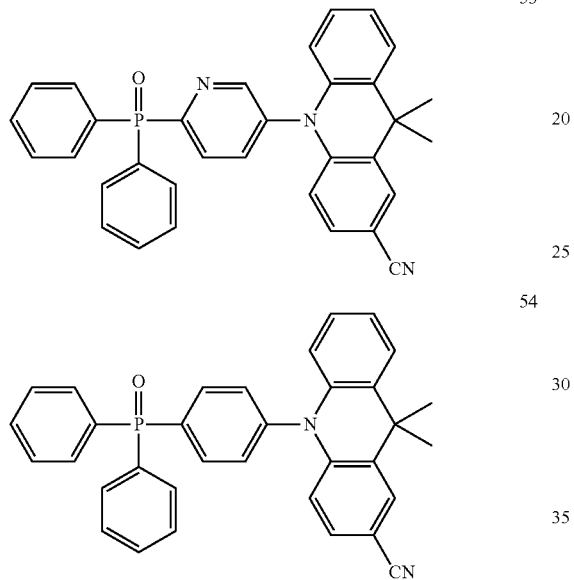
54
55
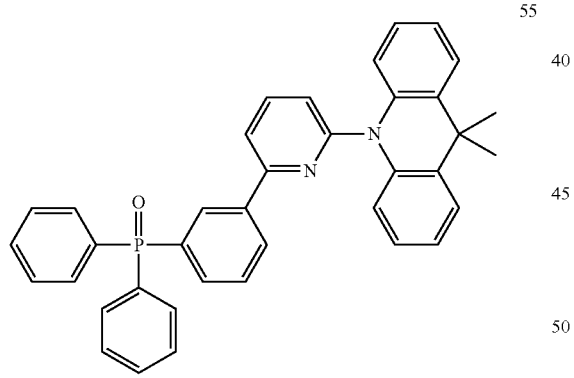
56
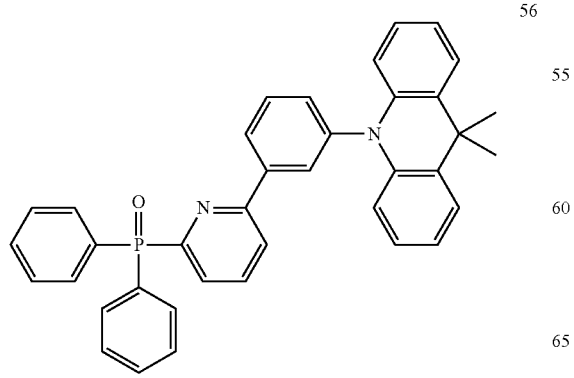
57
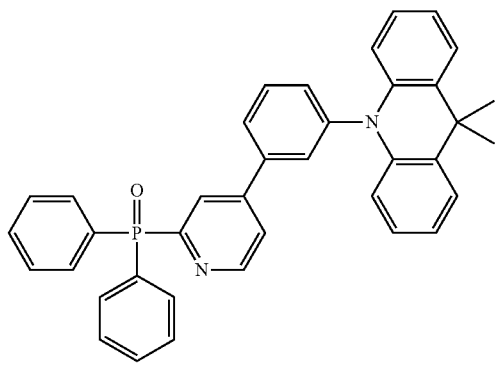
58
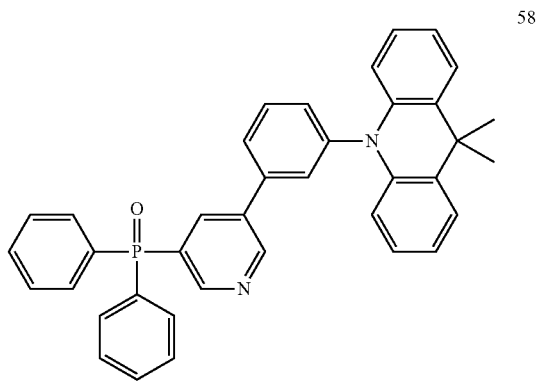
59
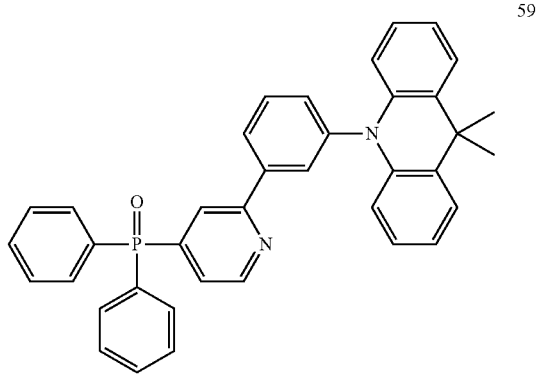
60
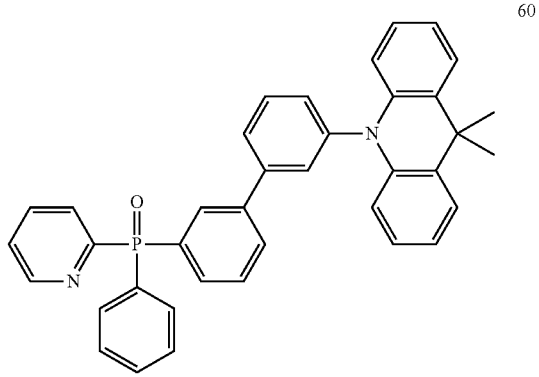

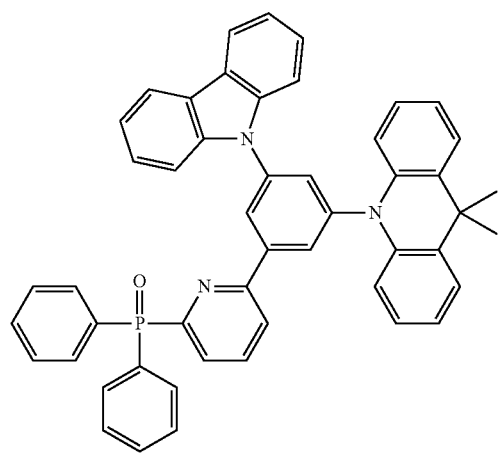
61
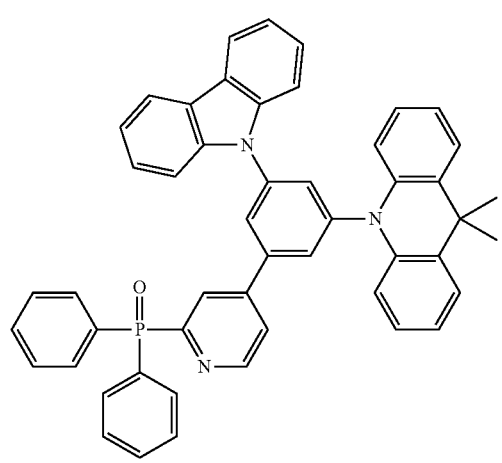
62
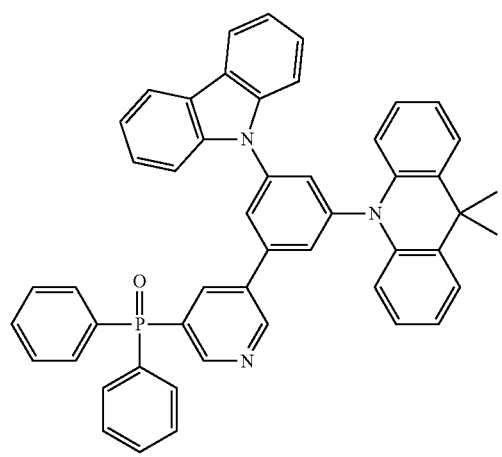
63
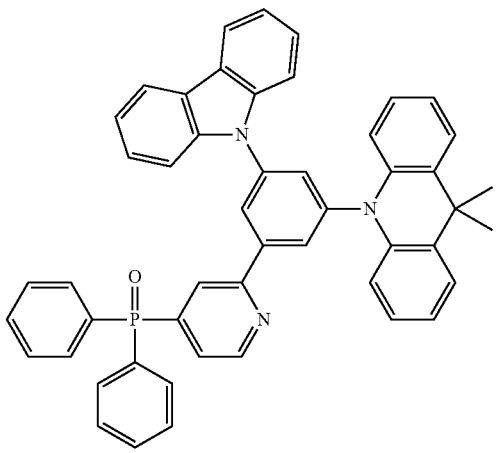
64
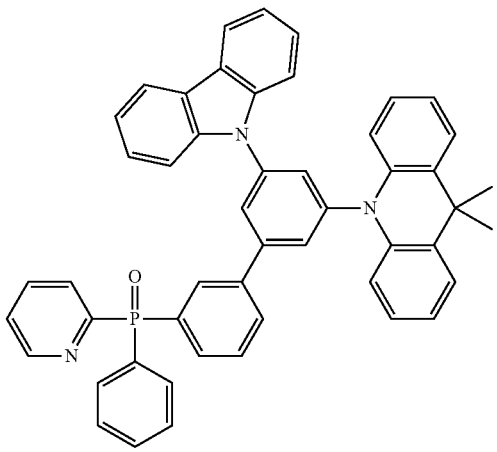
65
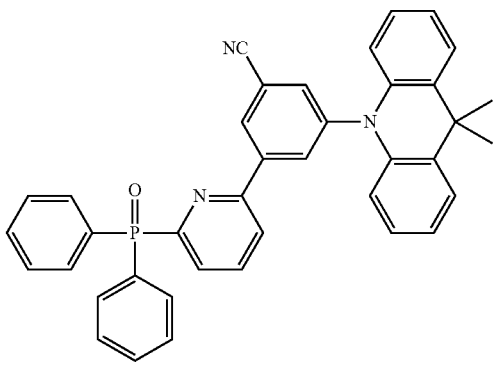
66
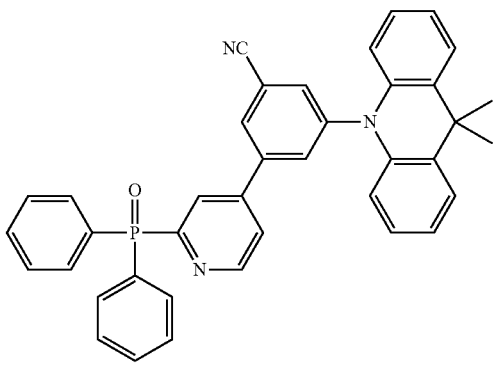
67

68
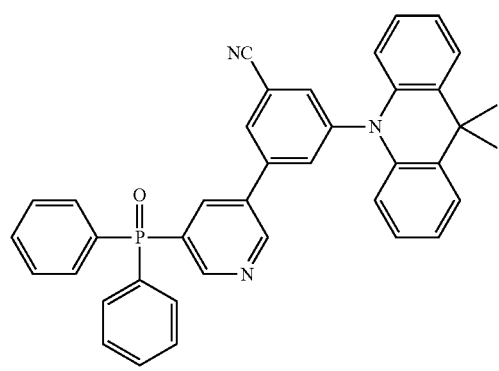
69
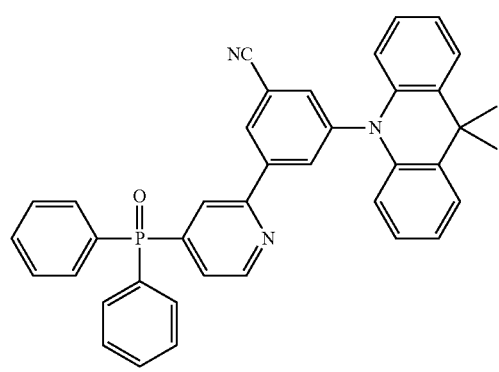
70
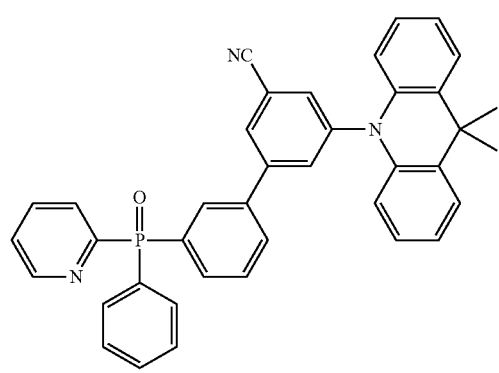
71
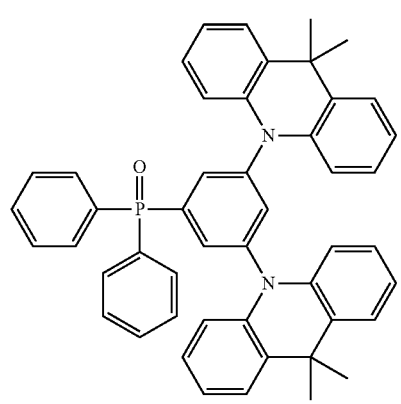
72
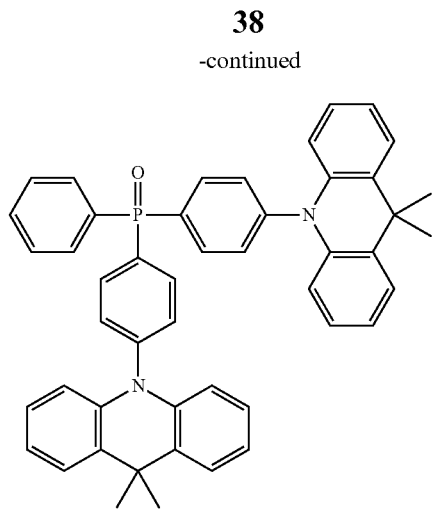
73
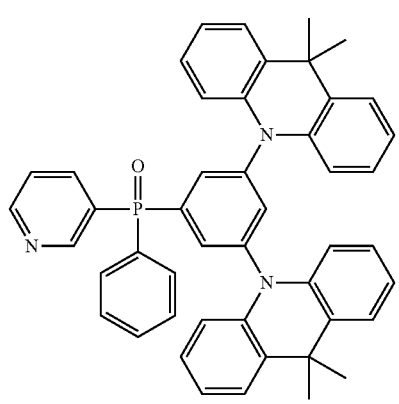
74
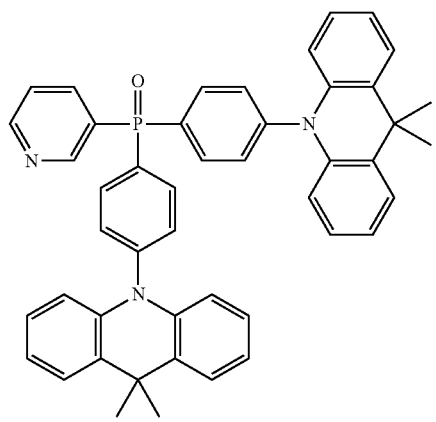
75
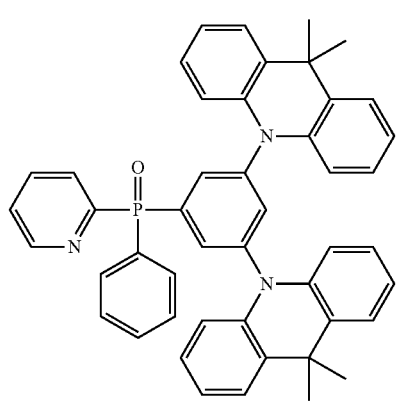

-continued

76

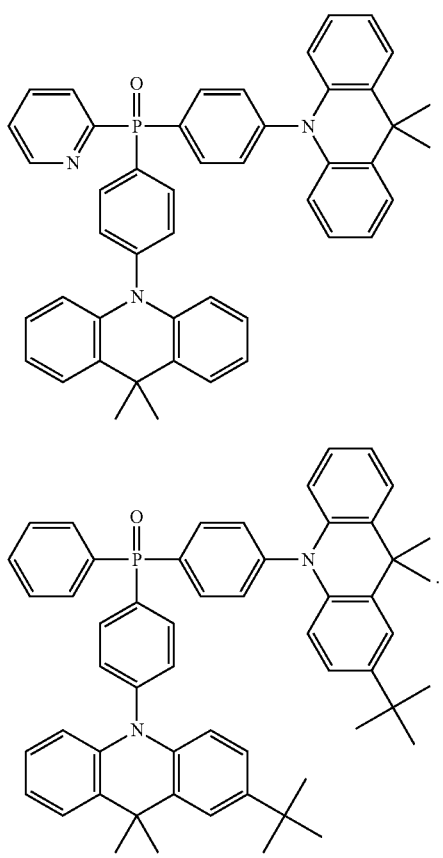

77

The heterocyclic compound represented by Formula 1 may have a heterocyclic structure having a phosphine oxide substituent, and thus may be advantageous in terms of luminous efficiency and energy transfer.

For example, in the heterocyclic compound, at least two substituents represented by Formula 2 may be substituted at a triaryl phosphine oxide, and thus the heterocyclic compound may have improved hole mobility as compared with a case in which the heterocyclic compound has only one substituent. Performance of a device may be varied by adjusting the position of the substituents to control the polarity of molecules.

In an implementation, in the heterocyclic compound, the substituent represented by Formula 2 may be bound to the phosphine oxide group via at least one π electron-depleted nitrogen-containing $C_2$-$C_{60}$ heterocyclic group (e.g., a pyridine group), thus facilitating control of polarity of the heterocyclic compound molecule and enabling suitable control of hole transportability or electron transportability in a device. Consequently, the heterocyclic compound may help improve device characteristics.

For example, the substituent represented by Formula 2 may help prevent an electron conjugation effect, as compared with a case having "O" instead of Y, thus increasing an energy gap of a material. Further, in the heterocyclic compound, when a "N" position in the π electron-depleted nitrogen-containing $C_2$-$C_{60}$ heterocyclic group bound to the phosphine oxide group is at an ortho-, meta-, or para-position with respect to a binding position to the phosphine oxide, the polarity of a molecule may increase in general, or intermolecular force may increase, resulting in an increase in electron transportability of a material. Consequently, the heterocyclic compound may help improve device characteristics.

In an implementation, in the heterocyclic compound, when the substituent represented by Formula 2 bound to the π electron-depleted nitrogen-containing $C_2$-$C_{60}$ heterocyclic group is at a meta- or para-position with respect to a binding position to the phosphine oxide, an energy level of a material may be easily controlled by adjusting electron donating characteristics, and device characteristics may improve by appropriately controlling electron and hole transportability of the material.

At least one heterocyclic compound represented by Formula 1 may be included between a pair of electrodes in an organic light-emitting device. In an implementation, the heterocyclic compound may be included in an emission layer and/or an electron transport region. In an implementation, the heterocyclic compound represented by Formula 1 may be used as a material for forming a capping layer, which is disposed on outer sides of a pair of electrodes in an organic light-emitting device.

Accordingly, there is provided an organic light-emitting device including a first electrode; a second electrode facing the first electrode; and an organic layer between the first electrode and the second electrode, wherein the organic layer includes an emission layer. The organic layer may include at least one heterocyclic compound represented by Formula 1.

As used herein, "(for example, the organic layer) including at least one heterocyclic compound" means that "(the organic layer) including a heterocyclic compound represented by Formula 1, or at least two different heterocyclic compounds represented by Formula 1".

For example, the organic layer may include Compound 1 only as the heterocylic compound. In this case, Compound 1 may be included in the emission layer of the organic light-emitting device. In an implementation, the organic layer may include Compounds 1 and 2 as the heterocyclic compounds. In this regard, Compounds 1 and 2 may be present in the same layer (e.g., Compounds 1 and 2 may be both present in an emission layer), or in different layers (e.g., Compound 1 may be present in an emission layer and Compound 2 may be present in a hole transport layer).

The organic layer may include i) a hole transport region between the first electrode (anode) and the emission layer that includes at least one selected from a hole injection layer, a hole transport layer, a buffer layer, and an electron blocking layer, and ii) an electron transport region between the emission layer and the second electrode (cathode) that includes at least one selected from a hole blocking layer, an electron transport layer, and an electron injection layer. At least one selected from the hole transport region and the emission layer may include at least one heterocyclic compound represented by Formula 1. In an implementation, the organic light-emitting device may include an emission layer, and the emission layer may include at least one heterocyclic compound represented by Formula 1. The emission layer may include a host and a dopant, and at least one selected from the host and the dopant may include at least one heterocyclic compound represented by Formula 1. In an implementation, the heterocyclic compound represented by Formula 1 included in the emission layer may serve as a host, and in this case, the emission layer may further include a dopant described herein. In an implementation, the heterocyclic compound represented by Formula 1 included in the emission layer may serve as a dopant, and in this case, the emission layer may further include a host described herein.

The organic light-emitting device may further include at least one selected from a first capping layer disposed in a path of light extracted or emitted from the emission layer, allowing the light to pass through to the outside after passing the first electrode; and a second capping layer disposed in a path of light extracted or emitted from the emission layer, allowing the light to pass through to the outside after passing the second electrode, wherein at least one selected from the first capping layer and the second capping layer may include at least one heterocyclic compound.

In an implementation, the organic light-emitting device may have a structure of i) first electrode, organic layer, second electrode, and second capping layer, ii) first capping layer, first electrode, organic layer, and second electrode, or iii) first capping layer, first electrode, organic layer, second electrode, and second capping layer, wherein layers of each structure are sequentially stacked in the stated order. At least one selected from the first capping layer and the second capping layer may include the heterocyclic compound.

The term "organic layer" as used herein refers to a single and/or a plurality of layers between the first electrode and the second electrode in an organic light-emitting device. A material included in the "organic layer" is not limited to an organic material.

Figure 1:
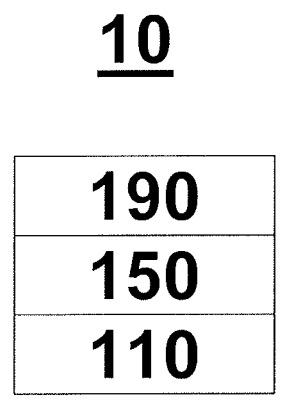

FIG. 1 illustrates a schematic view of an organic light-emitting device 10 according to an embodiment. The organic light-emitting device 10 may include the first electrode 110, the organic layer 150, and the second electrode 190.

Hereinafter, the structure of the organic light-emitting device 10 according to an embodiment and a method of manufacturing an organic light-emitting device according to an embodiment will be described in connection with FIG. 1.

In an implementation, a substrate may be additionally disposed under the first electrode 110 or above the second electrode 190. The substrate may be a glass substrate or a plastic substrate, each having excellent mechanical strength, thermal stability, transparency, surface smoothness, ease of handling, and water resistance.

The first electrode 110 may be formed by depositing or sputtering a material for forming the first electrode 110 over the substrate. When the first electrode 110 is an anode, the material for forming the first electrode 110 may be selected from materials with a high work function that facilitate hole injection.

The first electrode 110 may be a reflective electrode, a semi-transmissive electrode, or a transmissive electrode. When the first electrode 110 is a transmissive electrode, a material for forming the first electrode 110 may be selected from indium tin oxide (ITO), indium zinc oxide (IZO), tin oxide ($SnO_2$), zinc oxide (ZnO), and any combination thereof. When the first electrode 110 is a semi-transmissive electrode or a reflective electrode, as a material for forming the first electrode 110, at least one selected from magnesium (Mg), aluminum (Al), aluminum-lithium (Al—Li), calcium (Ca), magnesium-indium (Mg—In), magnesium-silver (Mg—Ag), and any combination thereof may be used.

The first electrode 110 may have a single-layered structure, or a multi-layered structure including two or more layers. In some embodiments, the first electrode 110 may have a triple-layer structure of ITO/Ag/ITO.

The organic layer 150 may be on the first electrode 110. The organic layer 150 may include an emission layer.

The organic layer 150 may further include a hole transport region between the first electrode 110 and the emission layer and an electron transport region between the emission layer and the second electrode 190.

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one selected from a hole injection layer, an emission auxiliary layer, and an electron blocking layer.

For example, the hole transport region may have a single-layered structure including a single layer including a plurality of different materials or a multi-layered structure, e.g., a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/ electron blocking layer structure, wherein layers of each structure are sequentially stacked on the first electrode 110 in each stated order.

The hole transport region may include at least one selected from m-MTDATA, TDATA, 2-TNATA, NPB (NPD), β-NPB, TPD, a spiro-TPD, a spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly (4-styrenesulfonate) (PEDOT/PSS), polyaniline/camphor sulfonic acid (PANI/CSA), (polyaniline)/poly(4-styrenesulfonate) (PANI/PSS), a compound represented by Formula 201, and a compound represented by Formula 202:

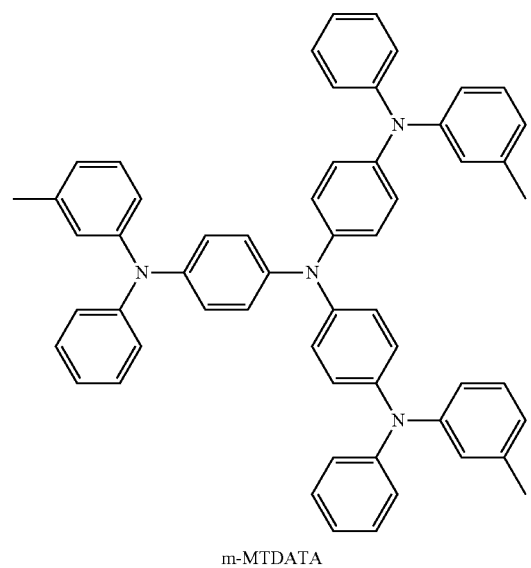

m-MTDATA

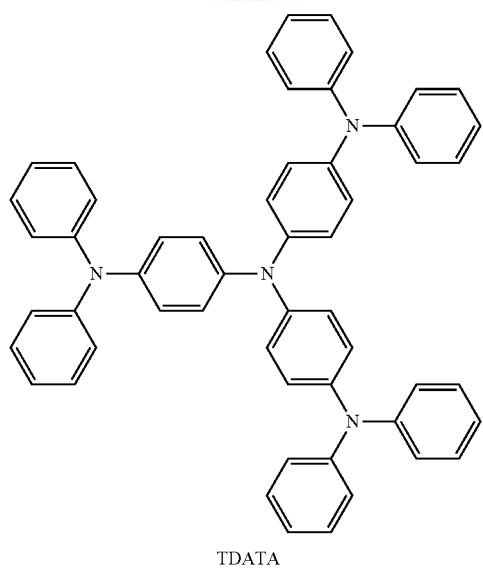
TDATA
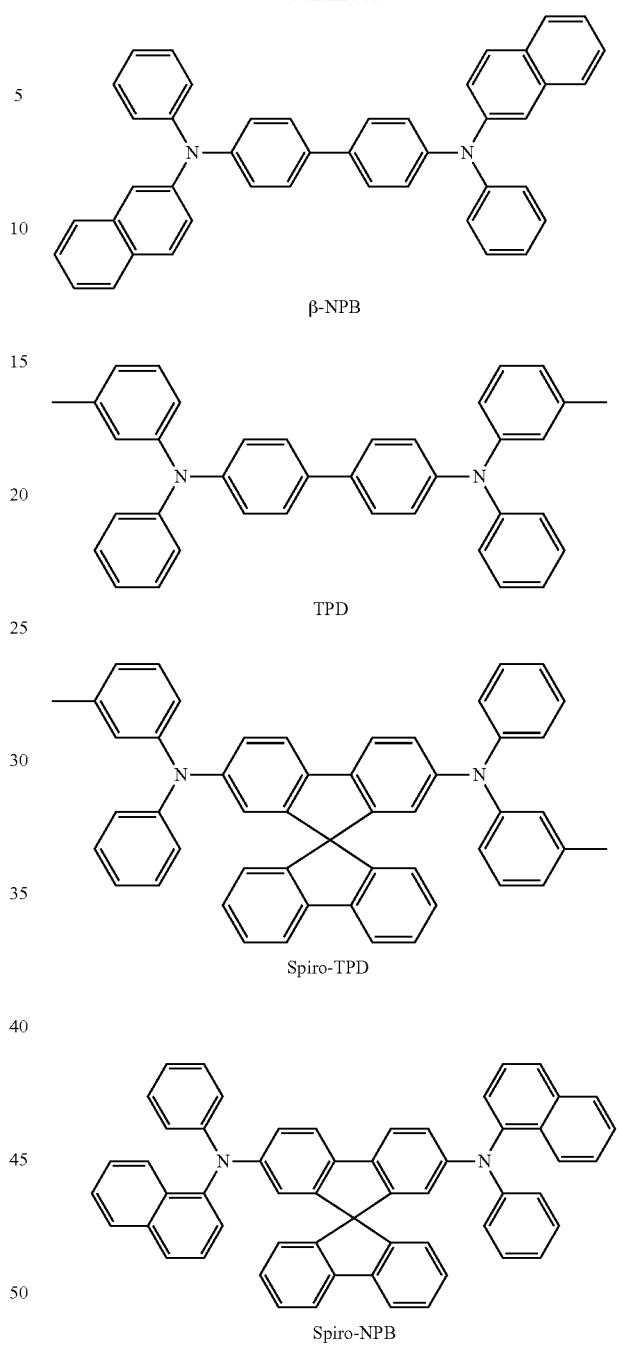
β-NPB
TPD
Spiro-TPD
Spiro-NPB
2-TNATA
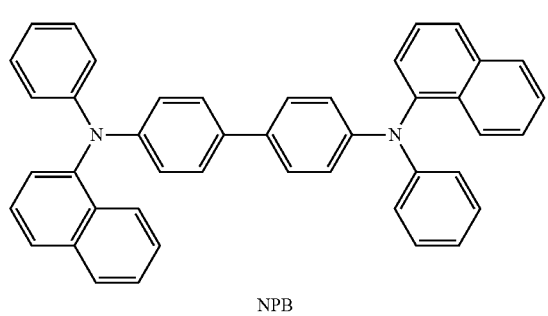
NPB
methylated NPB

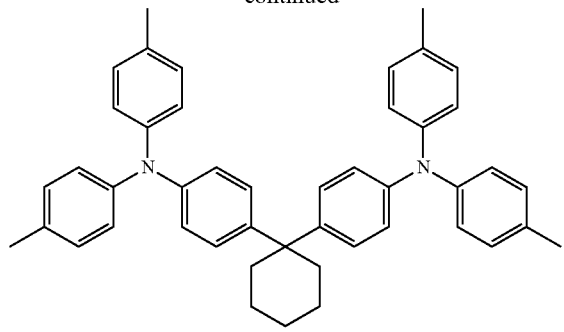

TAPC

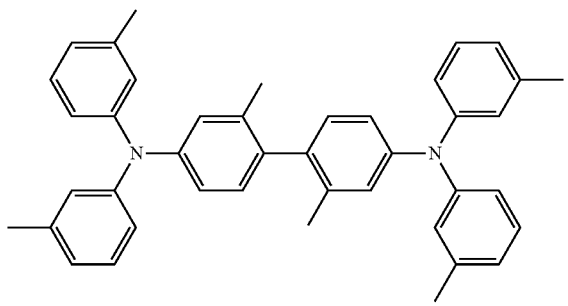

HMTPD

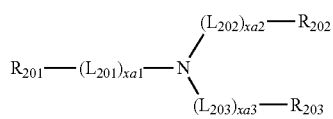

Formula 201

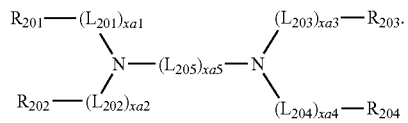

Formula 202

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formula 202, $R_{201}$ and $R_{202}$ may optionally be bound via a single bond, a dimethyl-methylene group, or a diphenyl-methylene group, and $R_{203}$ and $R_{204}$ may optionally be bound via a single bond, a dimethyl-methylene group, or a diphenyl-methylene group.

In some embodiments, in Formulae 201 and 202, $L_{201}$ to $L_{205}$ may each independently be selected from a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, $-Si(Q_{31})(Q_{32})(Q_{33})$, and $-N(Q_{31})(Q_{32})$, wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

According to another embodiment, xa5 may be 1, 2, 3, or 4.

According to some embodiments, $R_{201}$ to $R_{204}$ and $Q_{201}$ may each independently be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, $-Si(Q_{31})(Q_{32})(Q_{33})$, and $-N(Q_{31})(Q_{32})$.

wherein $Q_{31}$ to $Q_{33}$ may be the same as those described herein.

According to some embodiments, at least one selected from $R_{201}$ to $R_{203}$ in Formula 201 may be selected from a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group.

According to some embodiments, in Formula 202, i) $R_{201}$ and $R_{202}$ may be bound via a single bond, and/or ii) $R_{203}$ and $R_{204}$ may be bound via a single bond.

According to some embodiments, at least one selected from $R_{201}$ to $R_{204}$ in Formula 202 may be selected from a carbazolyl group; and a carbazolyl group substituted with at least one selected from deuterium. —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group.

The compound represented by Formula 201 may be represented by Formula 201A:

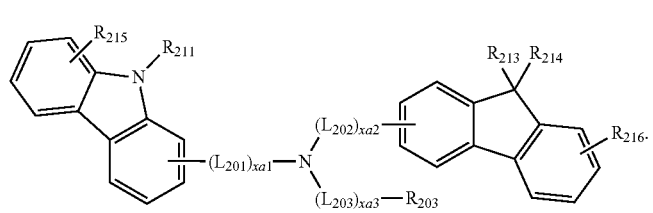

Formula 201A

In some embodiments, the compound represented by Formula 201 may be represented by Formula 201A(1).

In some embodiments, the compound represented by Formula 201 may be represented by Formula 201A-1:

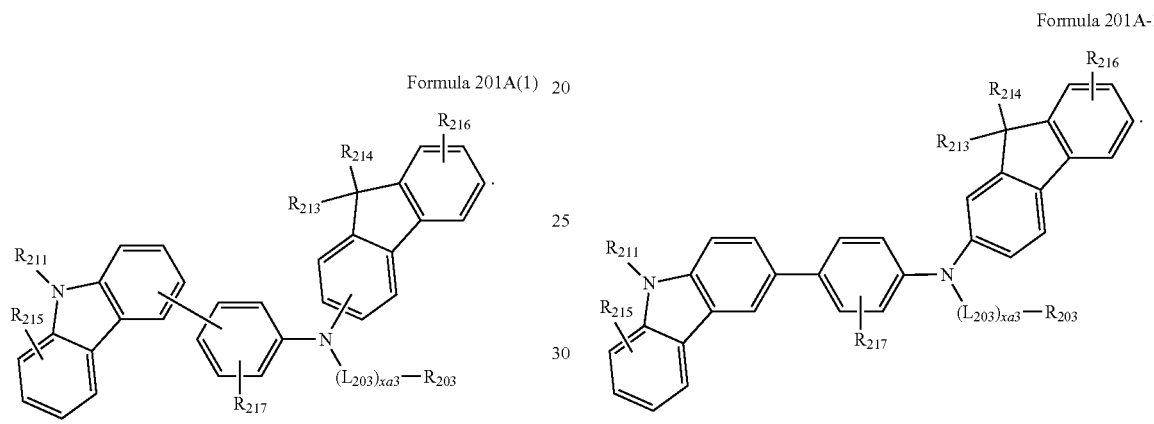

Formula 201A(1)

Formula 201A-1

In some embodiments, the compound represented by Formula 202 may be represented by Formula 202A:

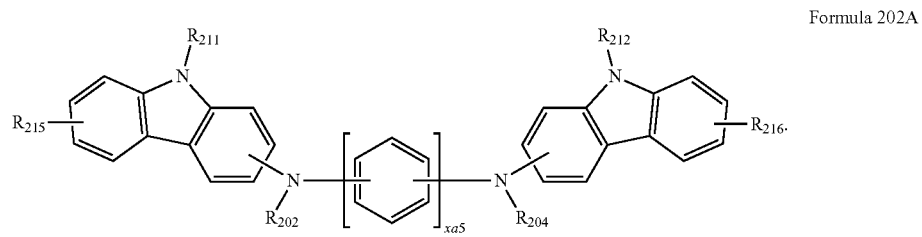

Formula 202A

In some embodiments, the compound represented by Formula 202 may be represented by Formula 202A-1:

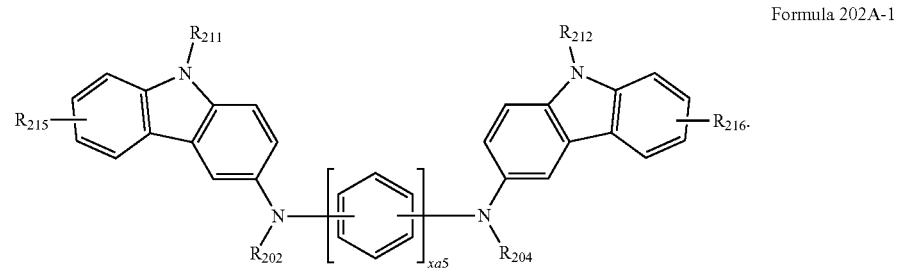

Formula 202A-1

In Formulae 201A, 201A(1), 201A-1, 202A, and 202A-1, $L_{201}$ to $L_{203}$, xa1 to xa3, xa5, and $R_{202}$ to $R_{204}$ may each independently be the same as those described herein, $R_{211}$ and $R_{212}$ may each independently be substantially the same as the those described herein with reference to $R_{203}$, and $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39:

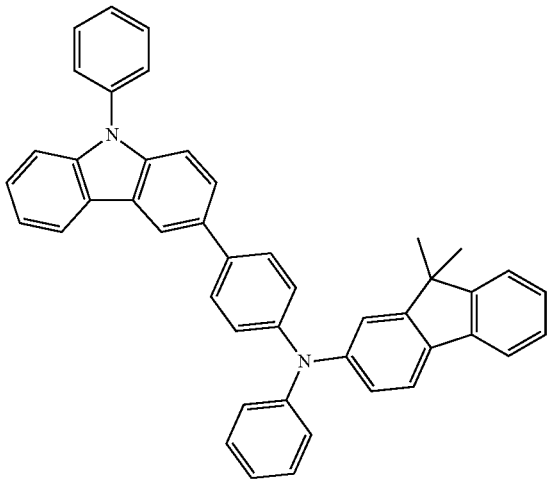

HT1

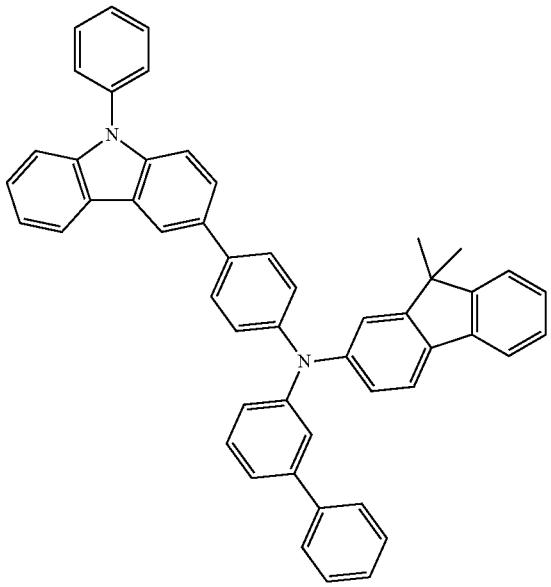

HT2

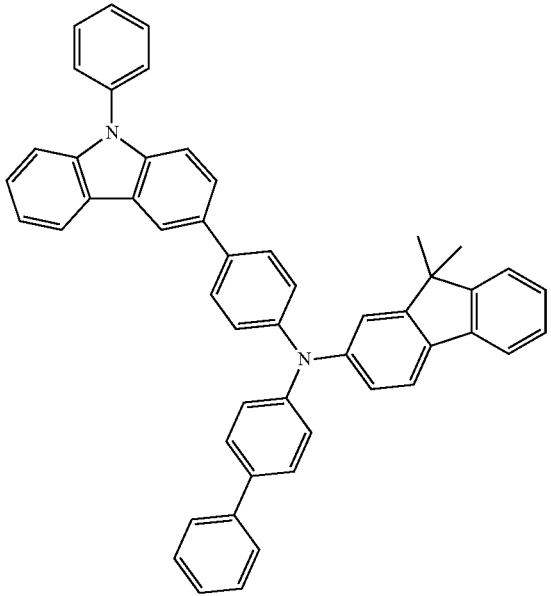

HT3

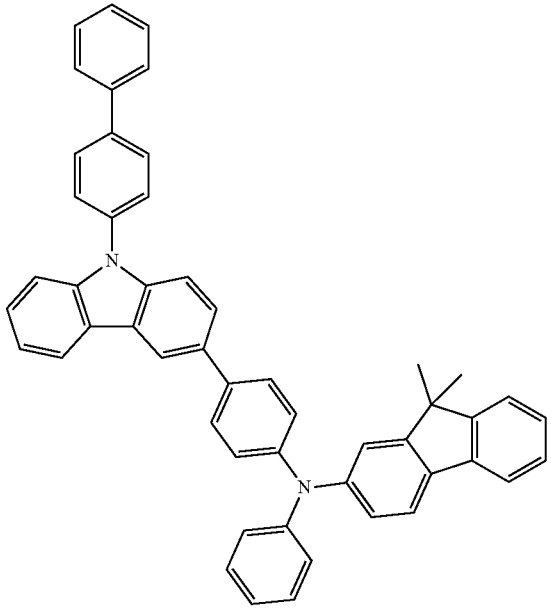

HT4

-continued
HT5
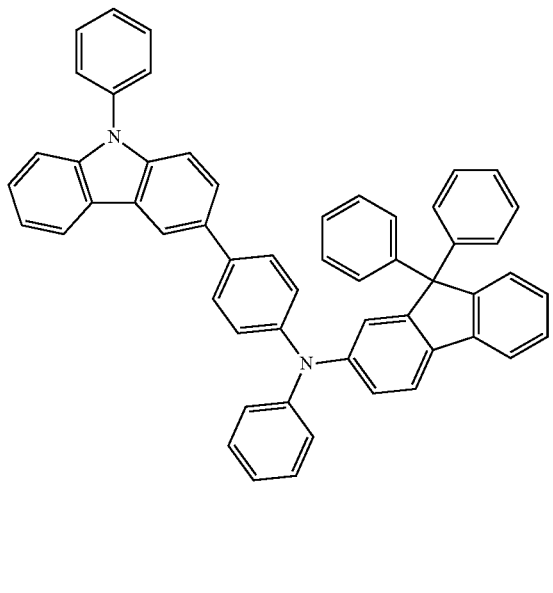
HT6
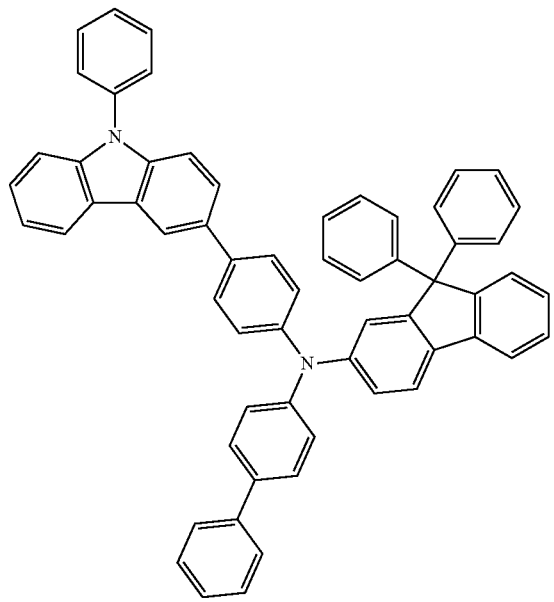
HT7
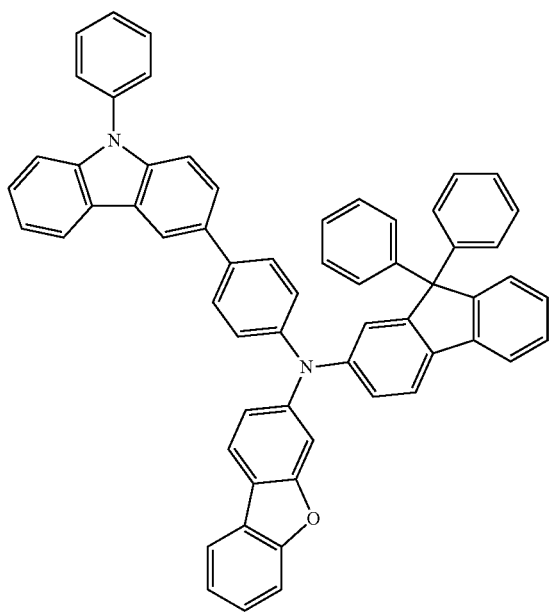
HT8
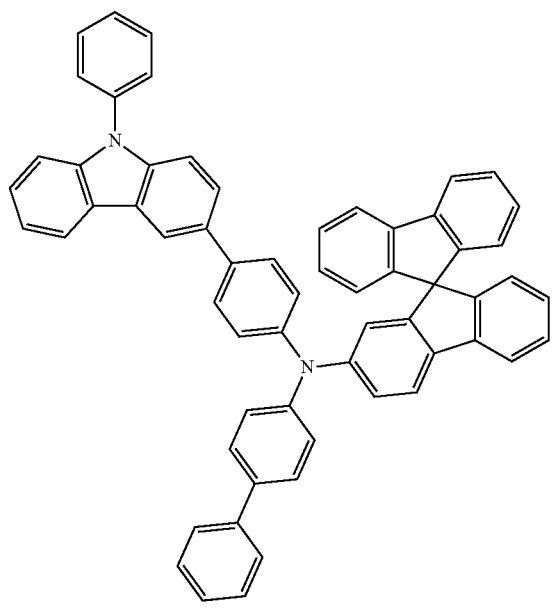

HT9
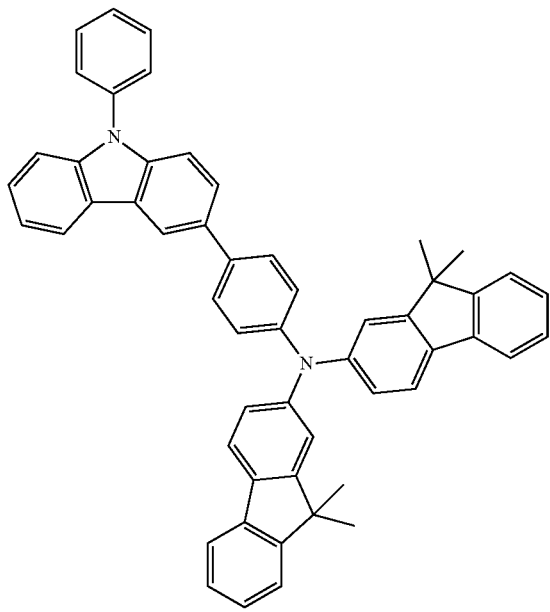
HT10
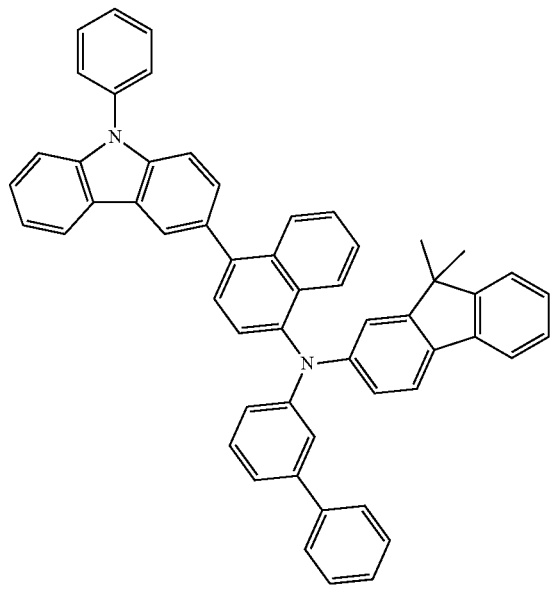
HT11
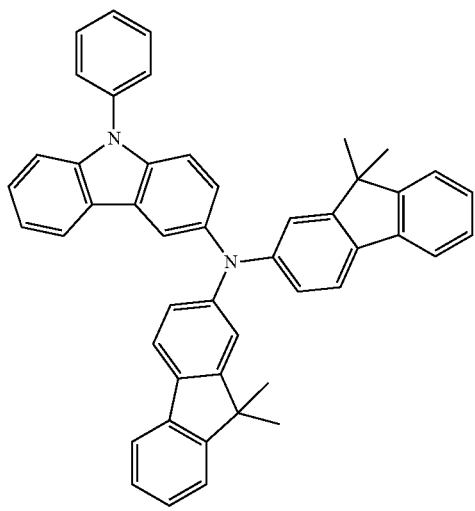
HT12
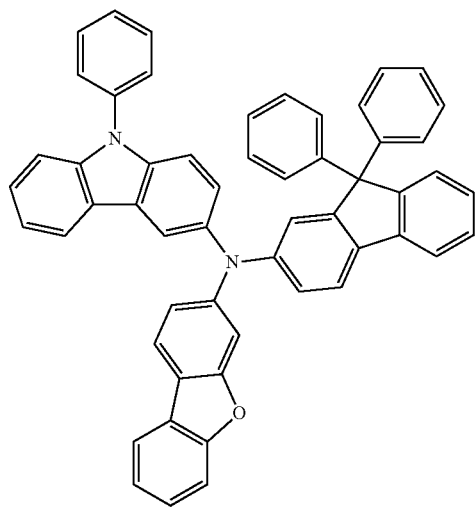

-continued
HT13
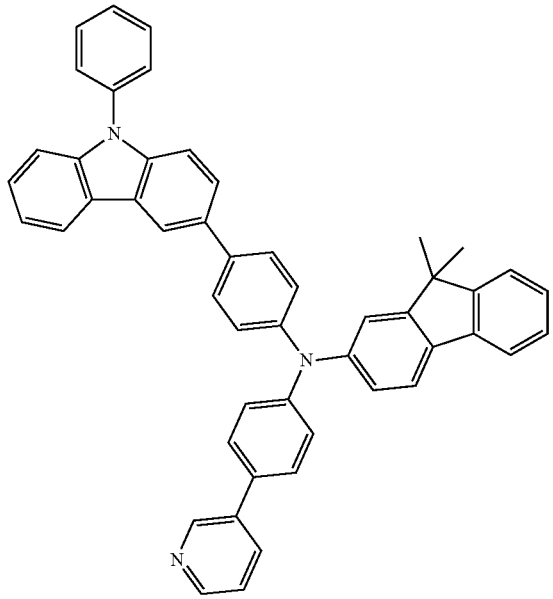
HT14
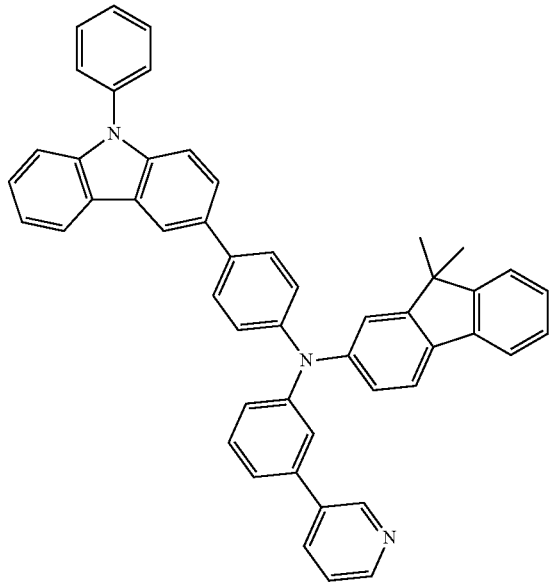
HT15
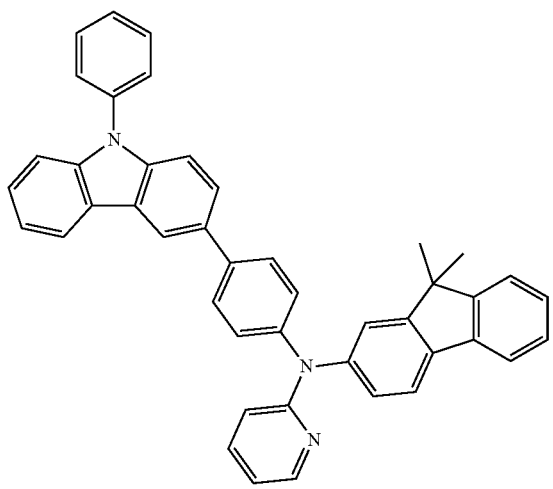
HT16
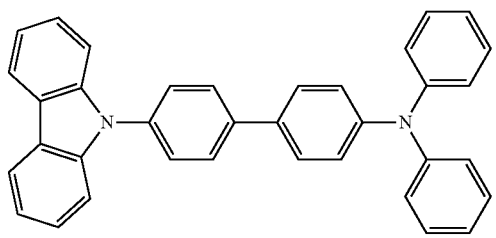
HT17
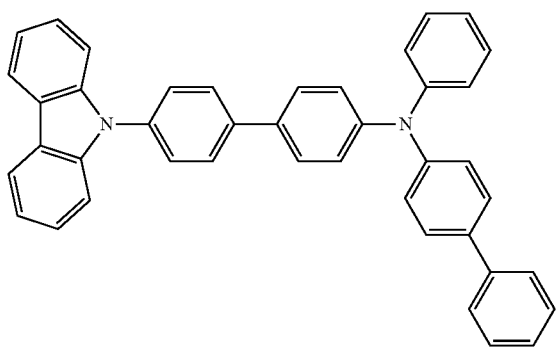
HT18
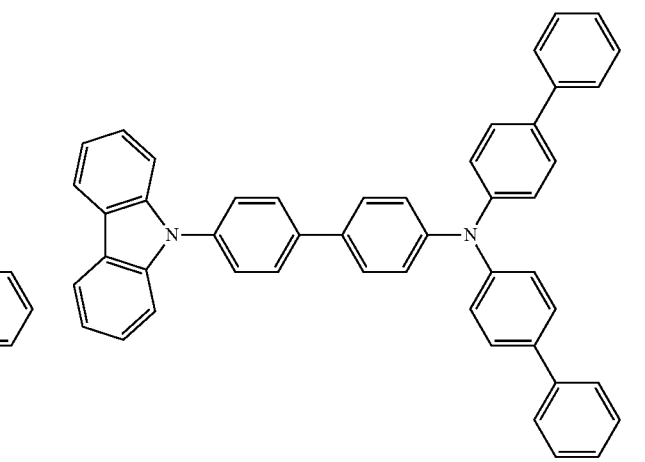

-continued
HT19
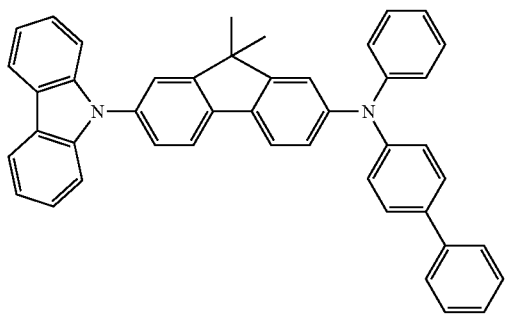
HT20
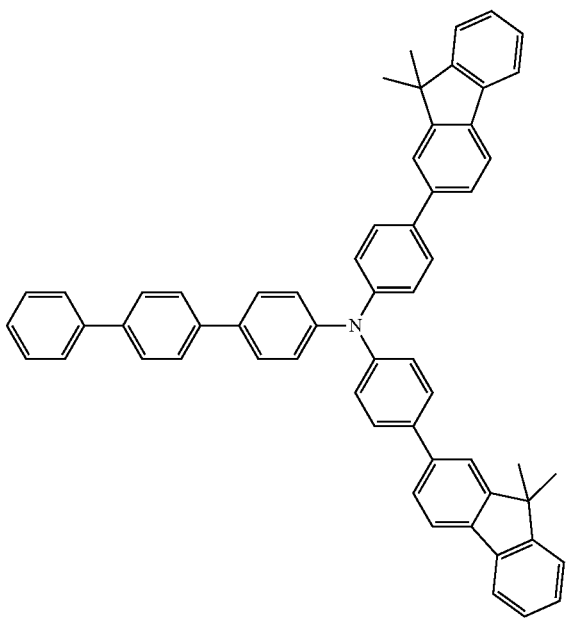
HT21
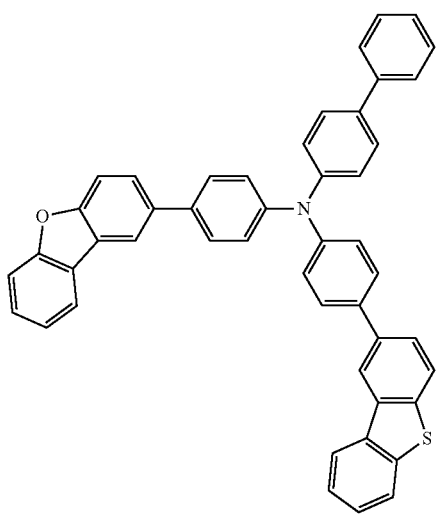
HT22
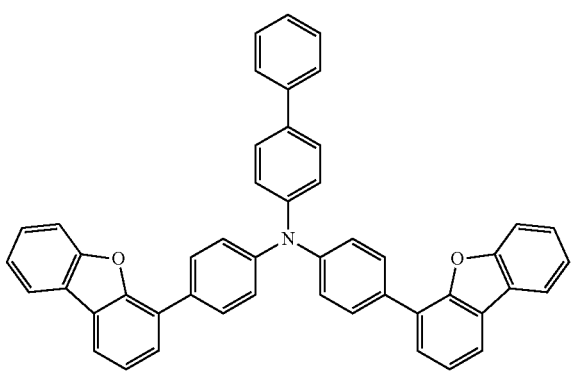
HT23
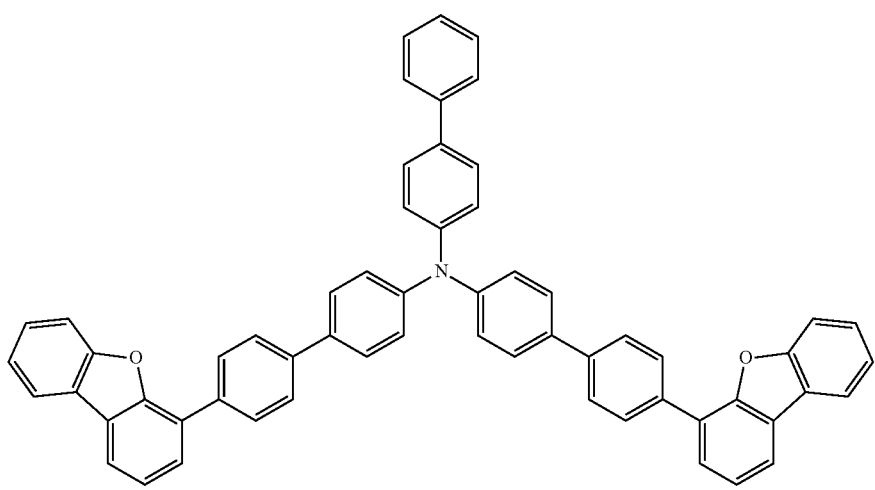

HT24
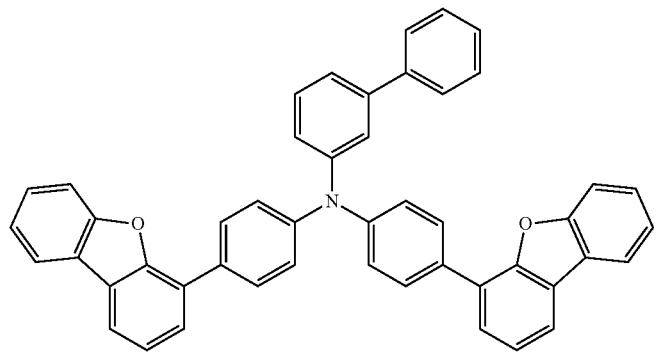
HT25
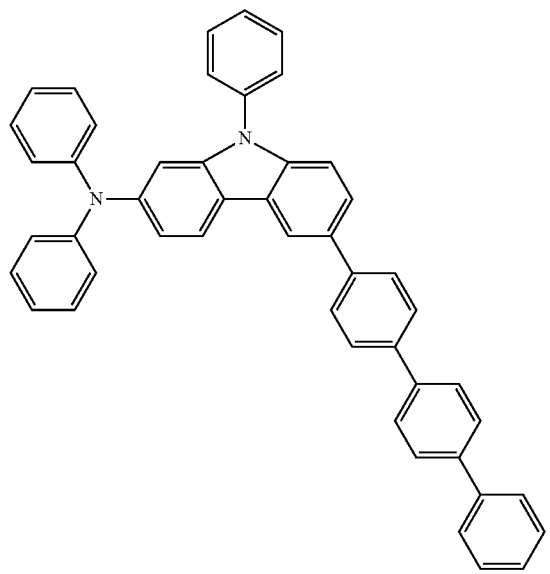
HT26
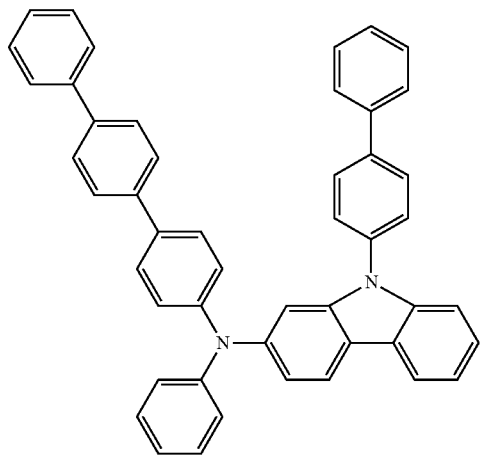
HT27
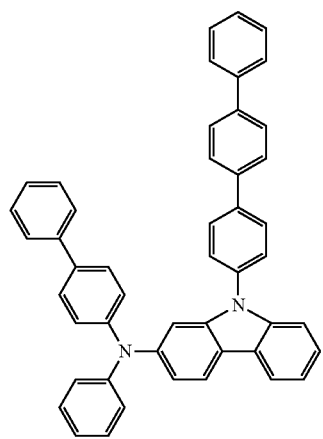
HT28
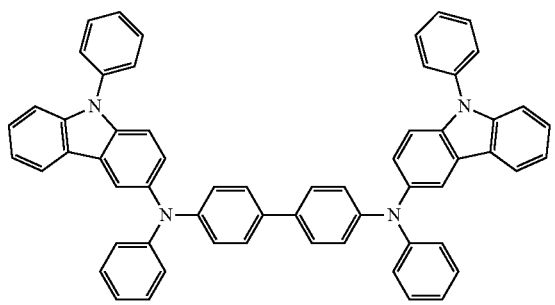

-continued
HT29
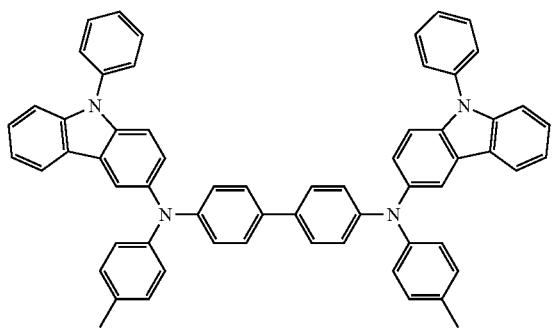
HT30
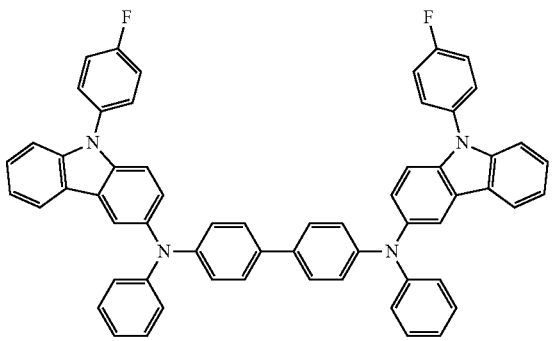
HT31
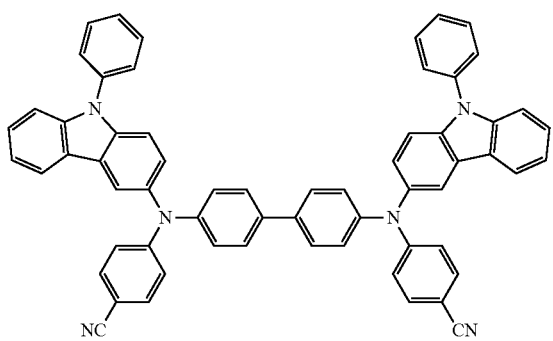
HT32
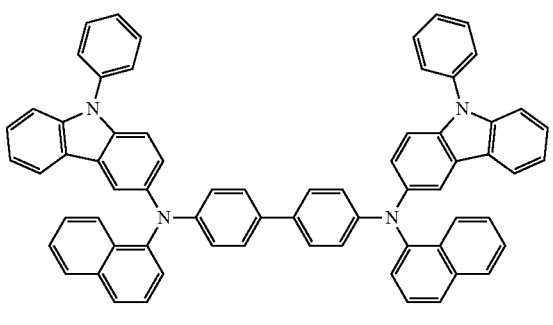
HT33
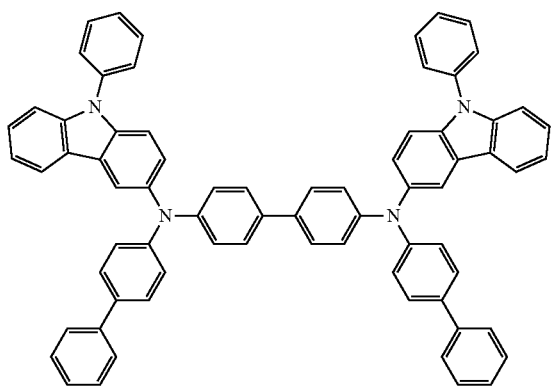
HT34
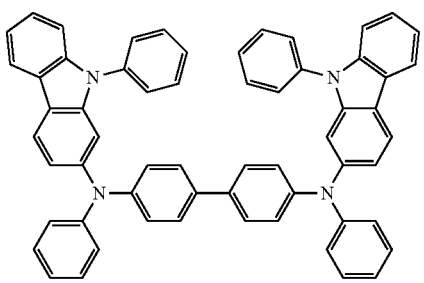
HT35
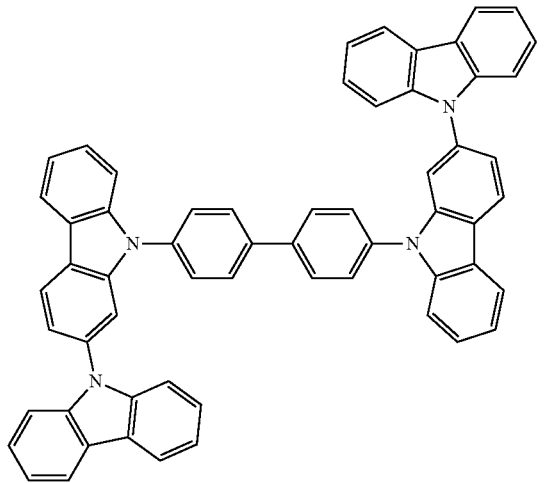
HT36
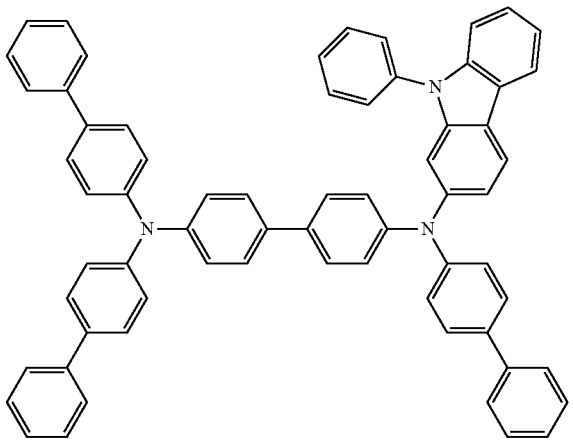

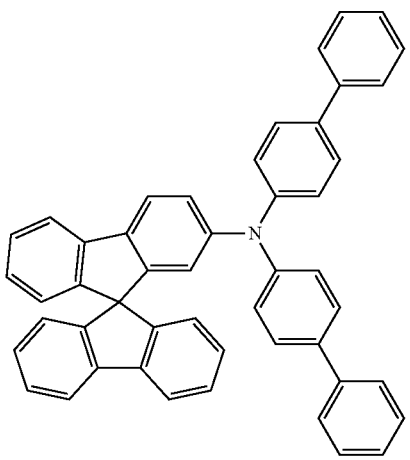

HT37

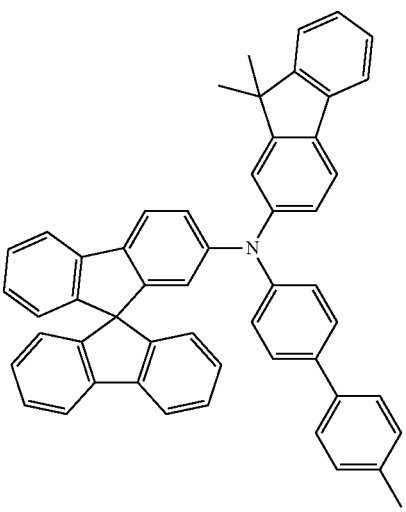

HT38

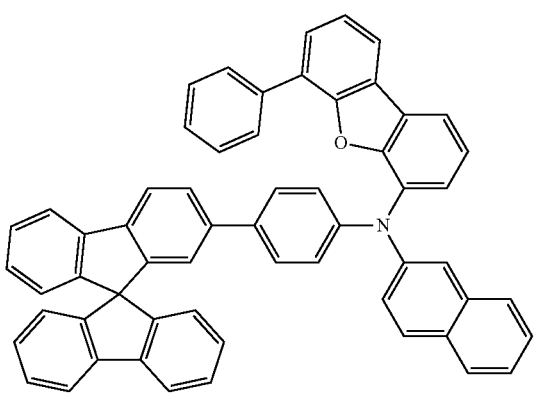

HT39

The thickness of the hole transport region may be in a range of about 100 (Angstroms) Å to about 10,000 Å, e.g., about 100 Å to about 1,000 Å. When the hole transport region includes at least one selected from a hole injection layer and a hole transport layer, the thickness of the hole injection layer may be in a range of about 100 Å to about 9,000 Å, e.g., about 100 Å to about 1,000 Å, and the thickness of the hole transport layer may be in a range of about 50 Å to about 2,000 Å, e.g., about 100 Å to about 1,500 Å. When the thicknesses of the hole transport region, the hole injection layer, and the hole transport layer are within any of these ranges, excellent hole transport characteristics may be obtained without a substantial increase in driving voltage.

The emission auxiliary layer may increase light emission efficiency by compensating for an optical resonance distance according to the wavelength of light emitted by an emission layer. The electron blocking layer may reduce or eliminate the flow of electrons from an electron transport region. The emission auxiliary layer and the electron blocking layer may include materials as described herein.

The hole transport region may include a charge generating material as well as the aforementioned materials, to improve conductive properties of the hole transport region. The charge generating material may be substantially homogeneously or non-homogeneously dispersed in the hole transport region.

The charge generating material may include, e.g., a p-dopant.

According to an embodiment, a lowest unoccupied molecular orbital (LUMO) of the p-dopant may be about −3.5 electron Volts (eV) or less.

The p-dopant may include at least one selected from a quinone derivative, a metal oxide, and a compound including a cyano group.

In some embodiments, the p-dopant may include at least one selected from a quinone derivative, such as tetracyanoquinodimethane (TCNQ) or 2,3,5,6-tetrafluoro-7,7,8,8-tetracyanoquinodimethane (F4-TCNQ);

a metal oxide, such as tungsten oxide or molybdenum oxide;

1,4,5,8,9,11-hexaazatriphenylene-hexacarbonitrile (HAT-CN); and a compound represented by Formula 221:

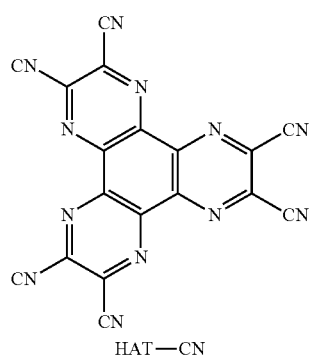

HAT—CN

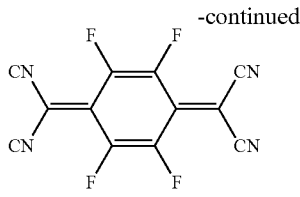

F4-TCNQ

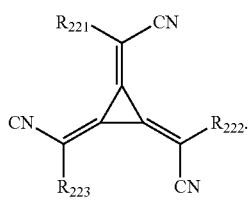

Formula 221

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that at least one selected from $R_{221}$ to $R_{223}$ may include at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

When the organic light-emitting device 10 is a full color organic light-emitting device, the emission layer may be patterned into a red emission layer, a green emission layer, or a blue emission layer, according to a sub-pixel. In one or more embodiments, the emission layer may have a stacked structure. The stacked structure may include two or more layers selected from a red emission layer, a green emission layer, and a blue emission layer. The two or more layers may be in direct contact with each other. Alternatively, the two or more layers may be separated from each other. In one or more embodiments, the emission layer may include two or more materials. The two or more materials may include a red light-emitting material, a green light-emitting material, or a blue light-emitting material. The two or more materials may be mixed with each other in a single layer. The two or more materials mixed with each other in the single layer may emit white light.

The emission layer may include a host and a dopant. The dopant may include at least one of a fluorescent dopant and a phosphorescent dopant.

The amount of the dopant in the emission layer may be, in general, in a range of about 0.01 parts to about 15 parts by weight based on 100 parts by weight of the host.

The thickness of the emission layer may be in a range of about 100 Å to about 1,000 Å, and in some embodiments, about 200 Å to about 600 Å. When the thickness of the emission layer is within any of these ranges, increased luminous characteristics may be obtained without a substantial increase in driving voltage.

The host may further include, in addition to the heterocyclic compound represented by Formula 1, a compound represented by Formula 301:

$[Ar_{301}]_{xb11}$-$[(L_{301})_{xb1}$-$R_{301}]_{xb21}$.   Formula 301

In Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), and xb21 may be an integer from 1 to 5, wherein $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group.

In some embodiments, $Ar_{301}$ in Formula 301 may be selected from a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xb11 in Formula 301 is 2 or greater, at least two $Ar_{301}$(s) may be bound via a single bond.

In one or more embodiments, the compound represented by Formula 301 may be represented by Formula 301-1 or 301-2:

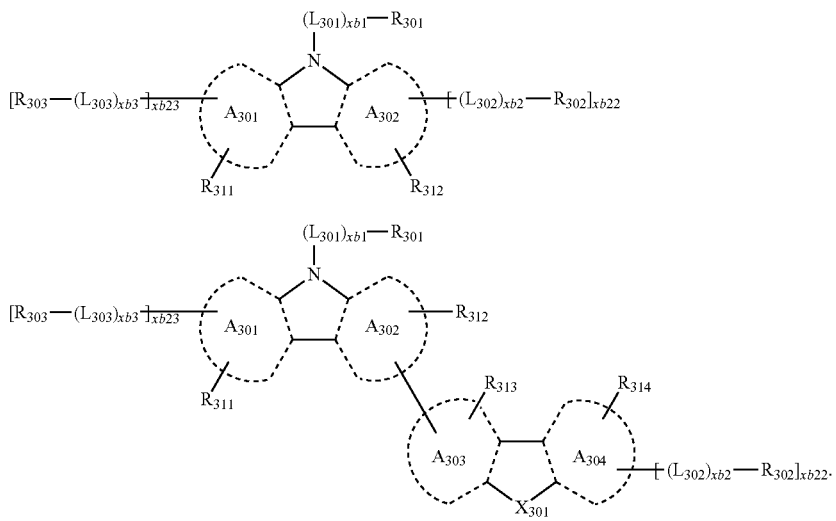

Formula 301-1

Formula 301-2

In Formulae 301-1 to 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonapthothiophene group, and a dinaphthothiophene group, $X_{301}$ may be O, S, or N-[$(L_{304})_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2, $L_{301}$, xb1, $R_{301}$, and $Q_{31}$ to $Q_{33}$ may each independently be the same as those described herein, $L_{302}$ to $L_{304}$ may each independently be substantially the same as those described with reference to $L_{301}$, xb2 to xb4 may each independently be substantially the same as those described with reference to xb1, and $R_{302}$ to $R_{304}$ may each independently be substantially the same as those described herein with reference to $R_{301}$.

In some embodiments, in Formulae 301, 301-1, and 301-2, $L_{301}$ to $L_{304}$ may each independently be selected from a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$)

wherein $Q_{31}$ to $Q_{33}$ may each independently be the same as those described herein.

In some embodiments, in Formulae 301, 301-1, and 301-2, $R_{301}$ to $R_{304}$ may each independently be selected from a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be the same as those described herein.

In some embodiments, the host may include an alkaline earth metal complex. For example, the host may include a beryllium (Be) complex, for example, Compound H55, a magnesium (Mg) complex, or a zinc (Zn) complex.

The host may include at least, in addition to the heterocyclic compound of represented by Formula 1, one selected from 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55:

H1
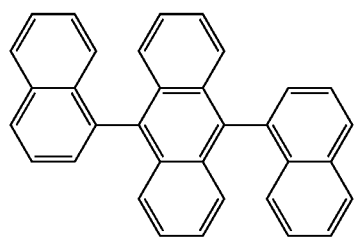

H2
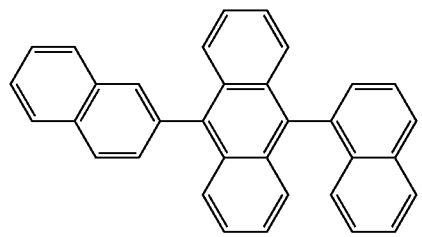

H3
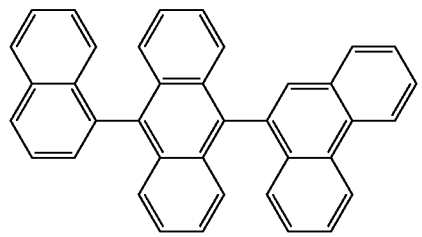

H4
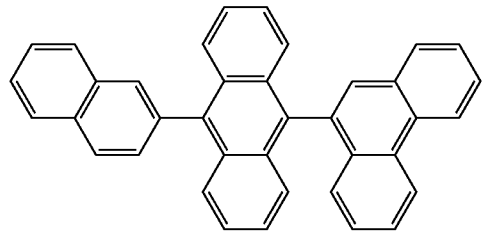

H5
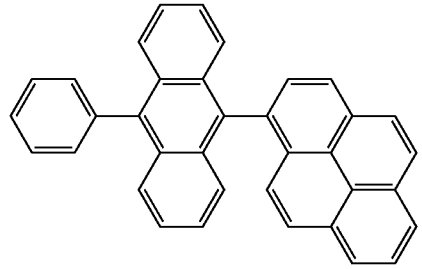

-continued

H6
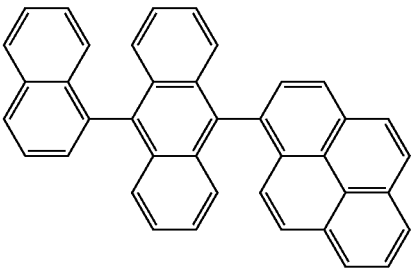

H7
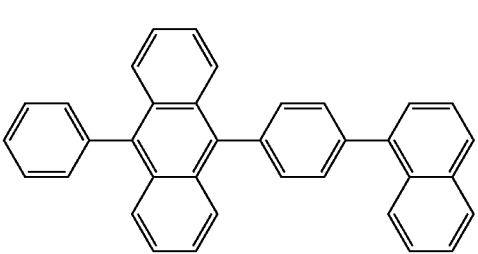

H8
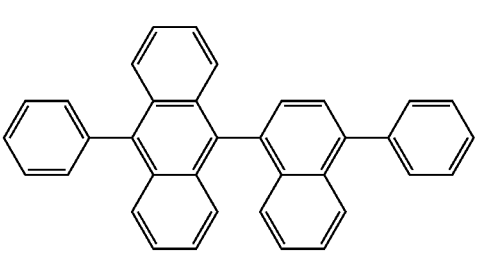

H9
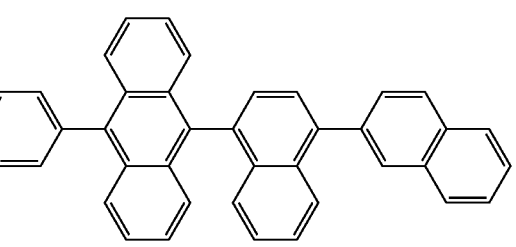

H10
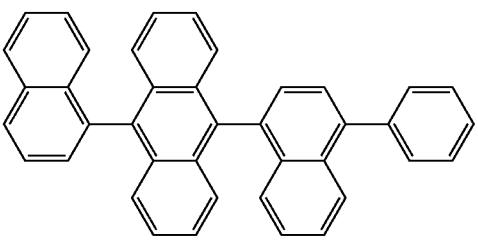

H11
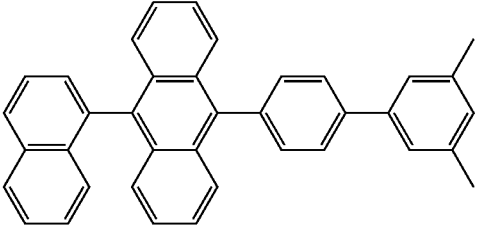

H12
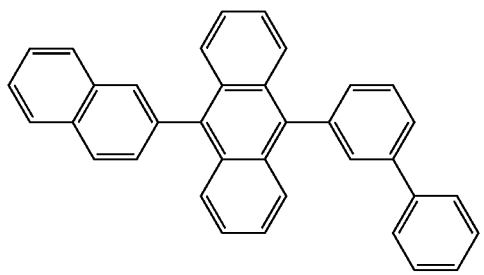
H13
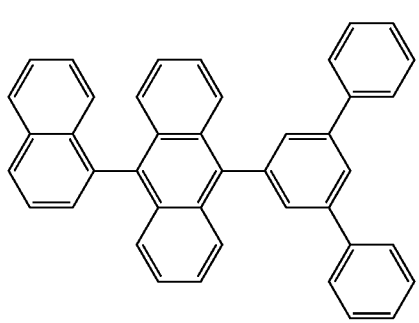
H14
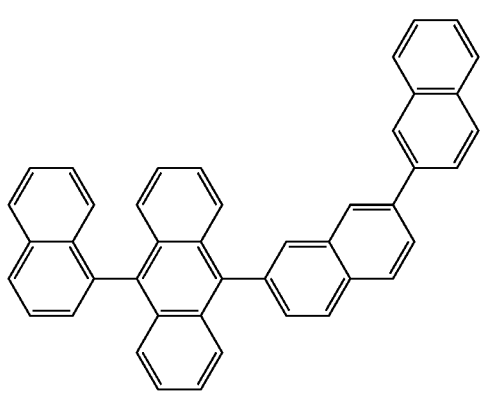
H15
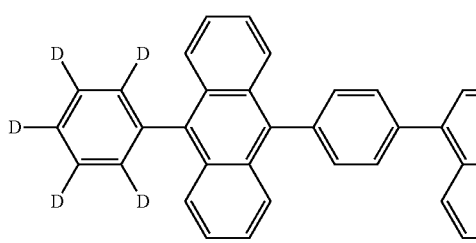
H16
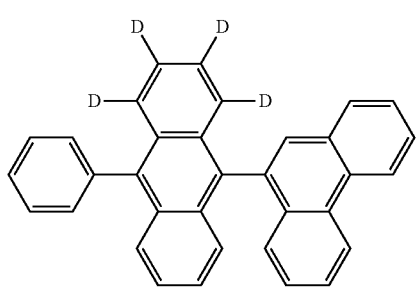
H17
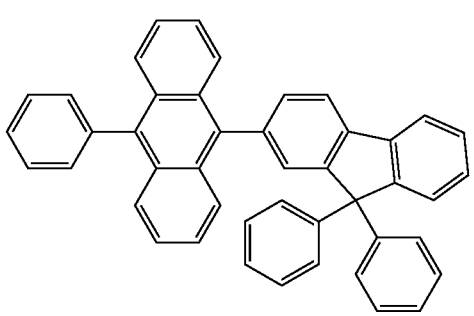
H18
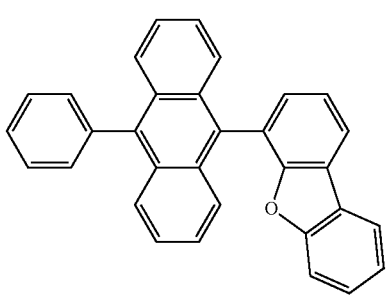
H19
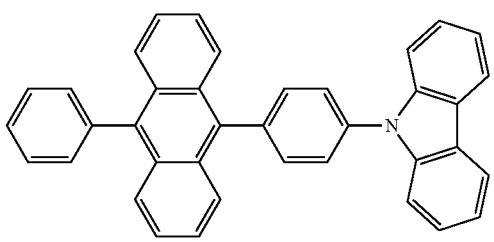
H20
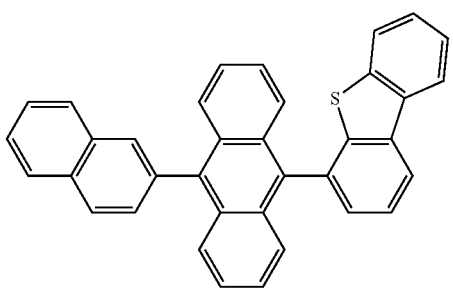
H21
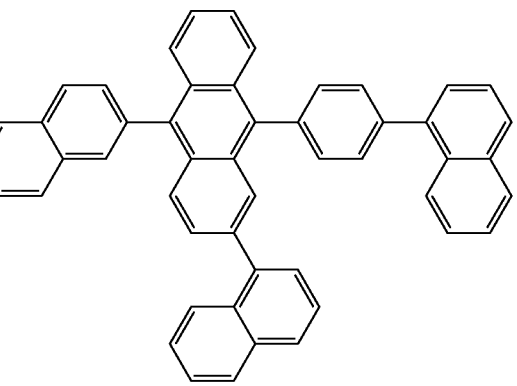

H22
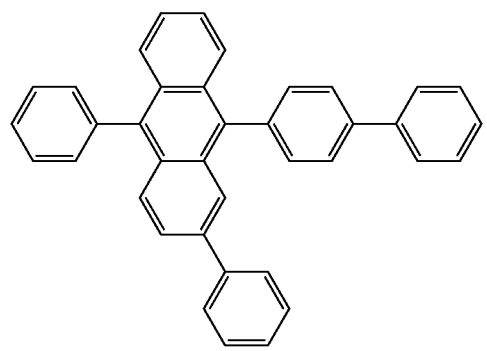
H23
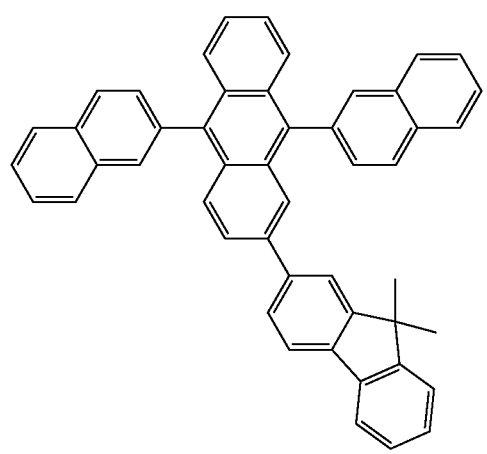
H24
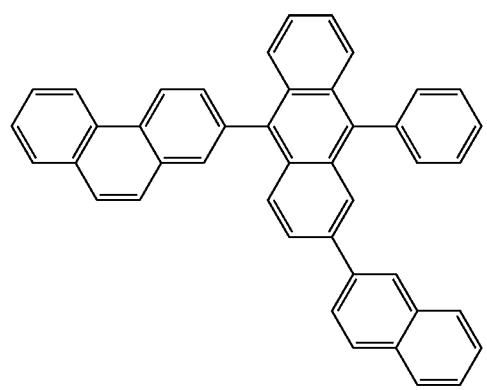
H25
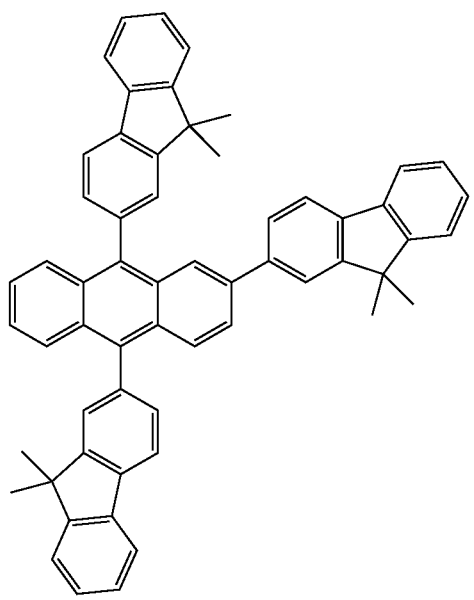
H26
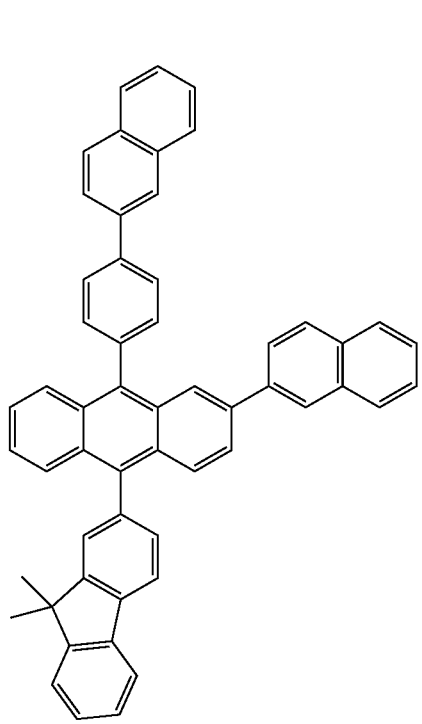

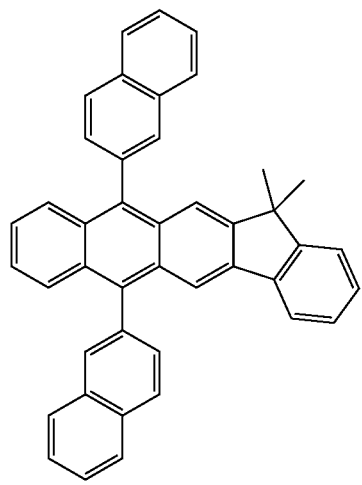
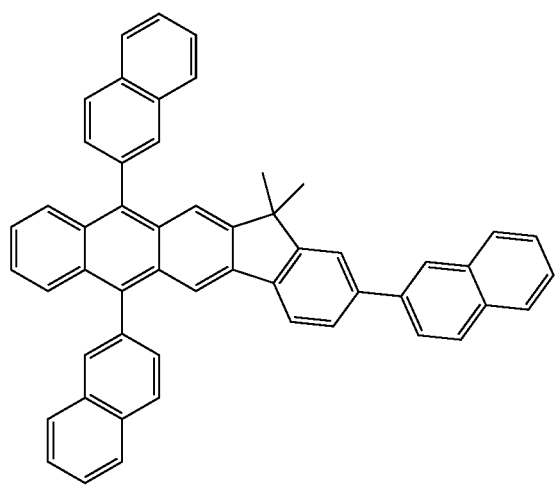
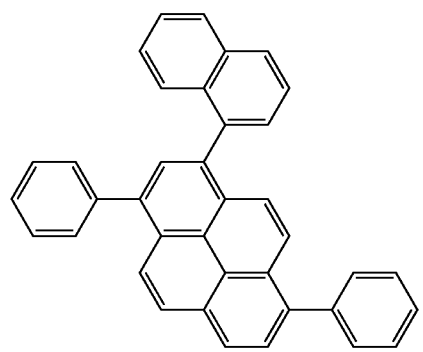
H27
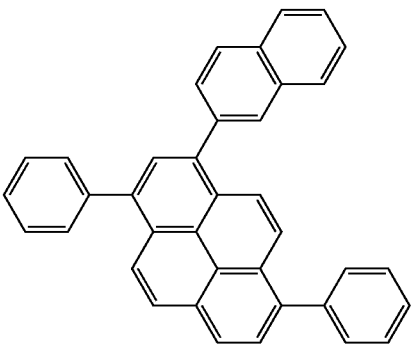
H28
H29
H30
H31
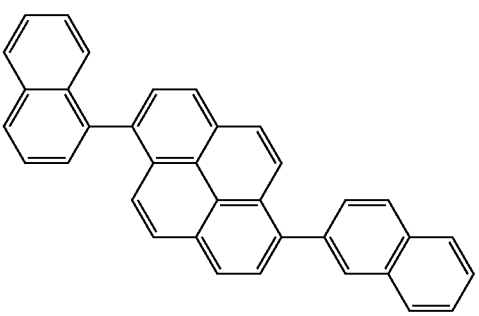
H32
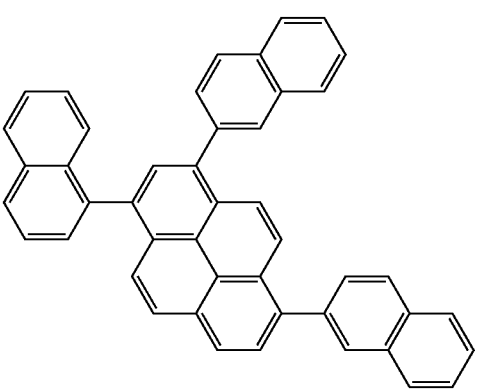
H33
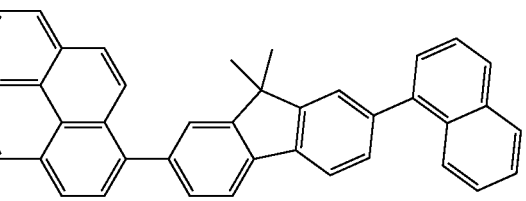
H34
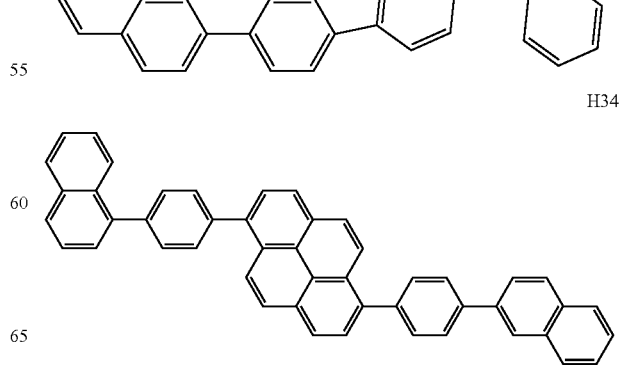

H35
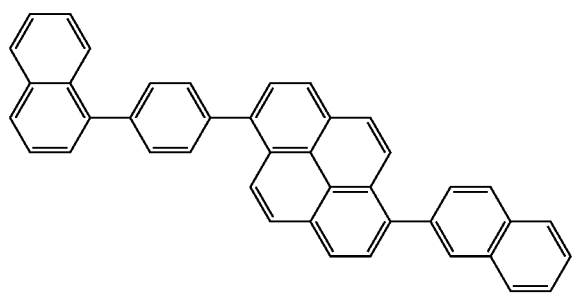
H36
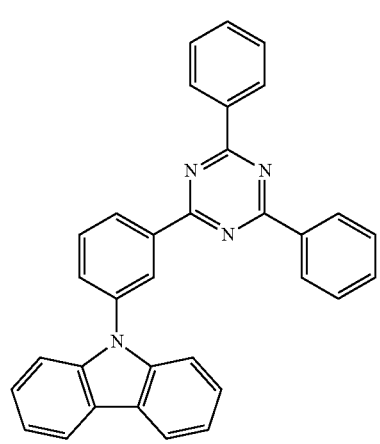
H37
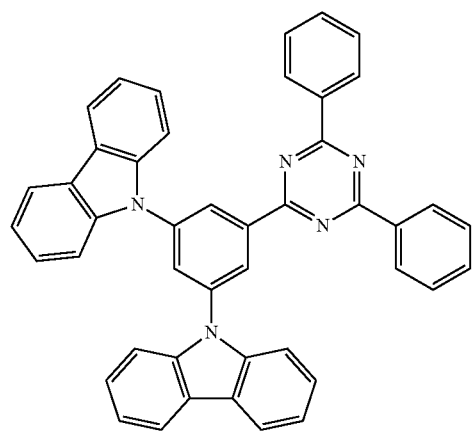
H38
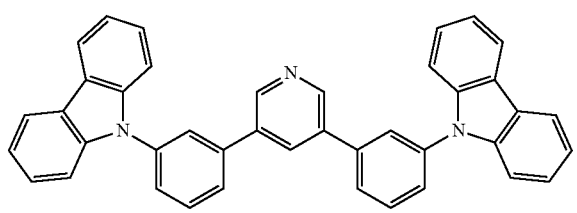
H39
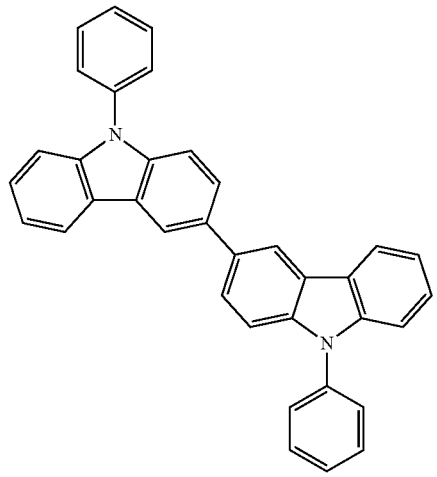
H40
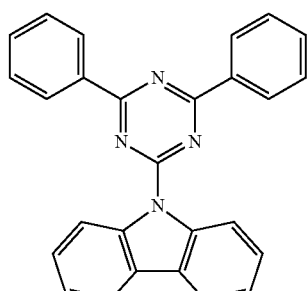
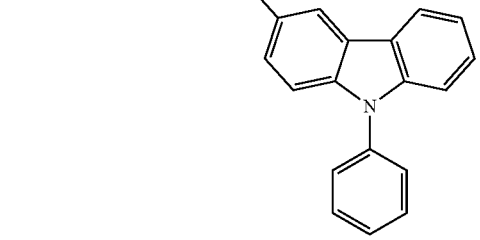
H41
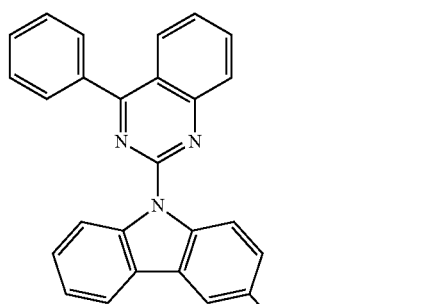
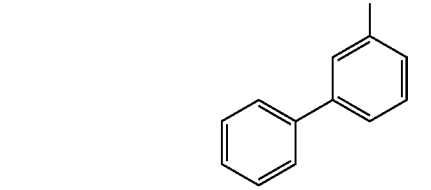

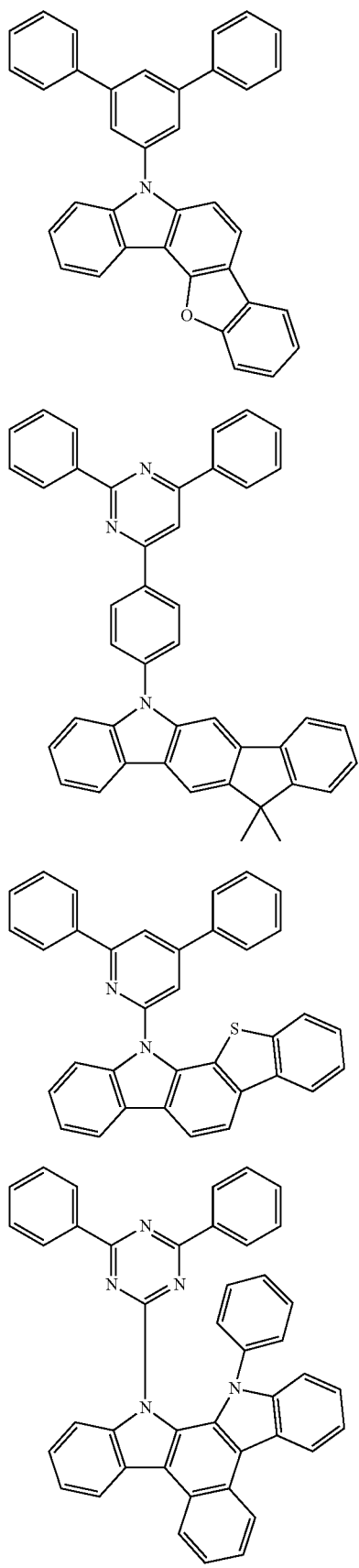

-continued

H52

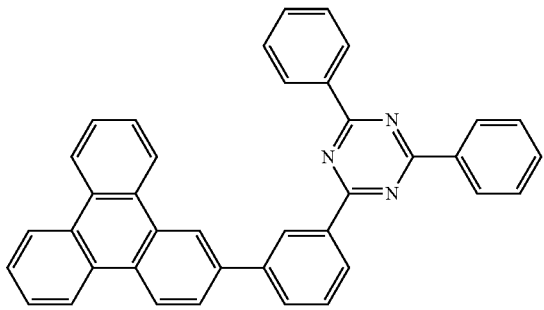

H53

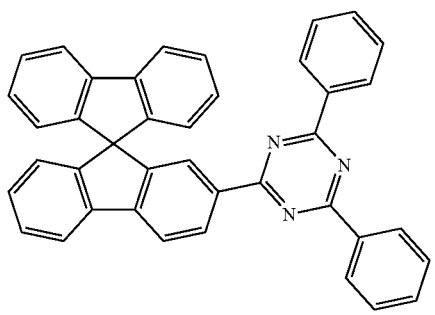

H54

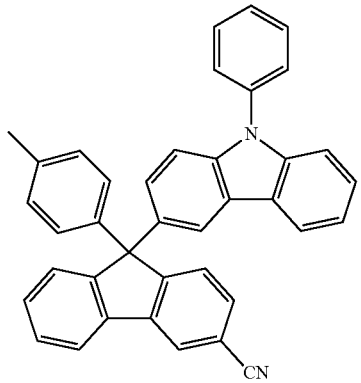

H55

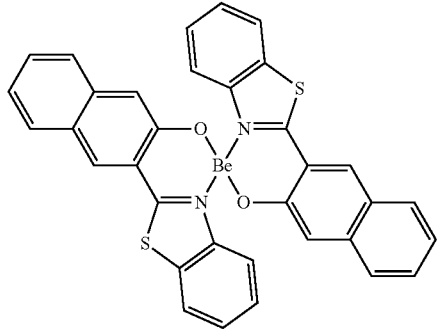

The dopant may further include, in addition to the heterocyclic compound represented by Formula 1, a phosphorescent dopant or a fluorescent dopant.

The phosphorescent dopant may include an organometallic complex represented by Formula 401:

$$M(L_{401})_{xc1}(L_{402})_{xc2}$$ Formula 401

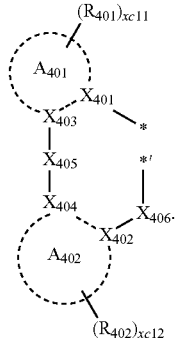

Formula 402

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402. xc1 may be an integer selected from 1, 2, and 3; when xc1 is 2 or greater, at least two $L_{401}$(s) may be identical to or different from each other, $L_{402}$ may be an organic ligand. xc2 may be an integer from 0 to 4; when xc2 is 2 or greater, at least two $L_{402}$(s) may be identical to or different from each other, $X_{401}$ to $X_{404}$ may each independently be nitrogen (N) or carbon (C), $X_{401}$ and $X_{403}$ may be linked via a single bond or a double bond, $X_{402}$ and $X_{404}$ may be linked via a single bond or a double bond, $A_{401}$ and $A_{402}$ may each independently be a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)—*', *—C($Q_{411}$)($Q_{412}$)—*', *—C($Q_{411}$)=C($Q_{412}$)—*', *—C($Q_{411}$)=*', or *=C($Q_{411}$)—*', wherein $Q_{411}$ and $Q_{412}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S.

$R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10, and

* and *' in Formula 402 each indicate a binding site to M in Formula 401.

In an embodiment, in Formula 402, $A_{401}$ and $A_{402}$ may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may each be nitrogen.

According to some embodiments, $R_{401}$ and $R_{402}$ in Formula 402 may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantyl group, a norbornanyl group, and a norbornenyl group;

a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group.

In one or more embodiments, when xc1 in Formula 401 is 2 or greater, two $A_{401}$(s) in at least two $L_{401}$(s) may optionally be linked via $X_{407}$ as a linking group, and two $A_{402}$(s) may optionally be linked via $X_{408}$ as a linking group (see e.g., Compounds PD1 to PD4 and PD7). $X_{407}$ and $X_{408}$ may each independently be selected from a single bond, *—O—*', *—S—*', *—C(=O)—*', *—N($Q_{413}$)-*', *—C($Q_{413}$)($Q_{414}$)-*', and *—C($Q_{413}$)=C($Q_{414}$)-*', wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group.

$L_{402}$ in Formula 401 may be any suitable monovalent, divalent, or trivalent organic ligand. In some embodiments, $L_{402}$ may be selected from halogen, diketone (e.g., acetylacetonate), a carboxylic acid (e.g., picolinate), —C(=O), isonitrile, —CN, and phosphorus (e.g., phosphine or phosphite).

In some embodiments, the phosphorescent dopant may include, for example, at least one selected from Compounds PD1 to PD25:

PD1

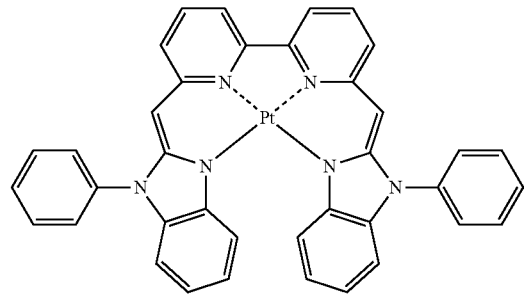

PD2

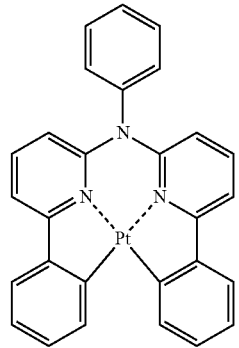

PD3

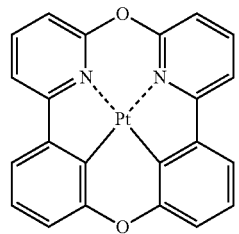

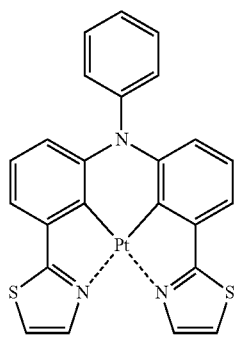
PD4
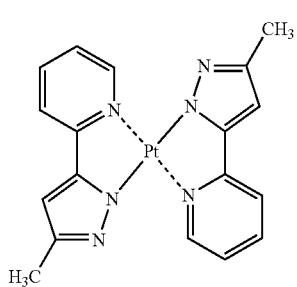
PD5
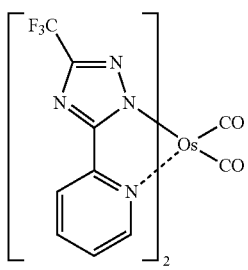
PD6
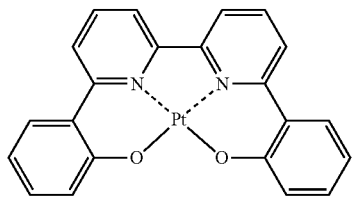
PD7
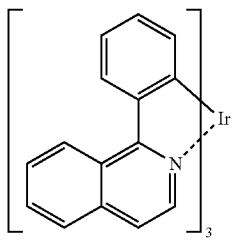
PD8
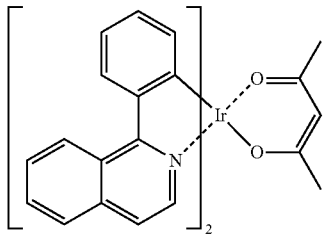
PD9
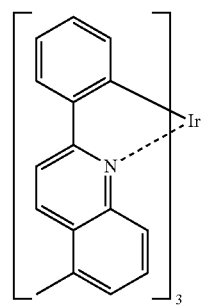
PD10
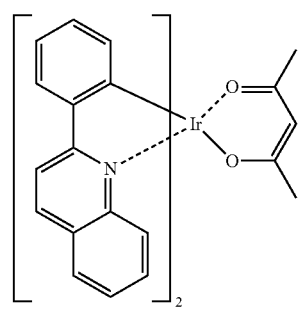
PD11
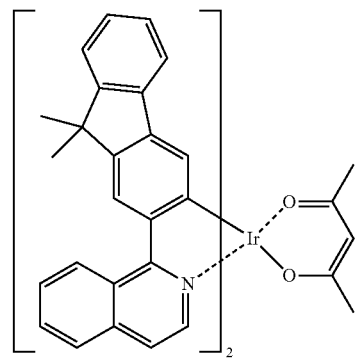
PD12
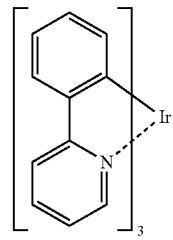
PD13
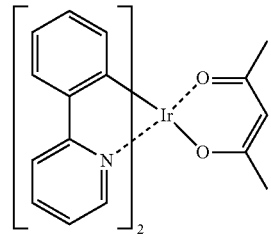
PD14

-continued
PD15
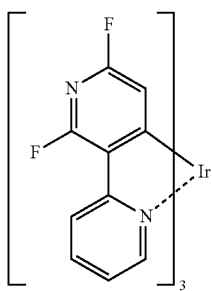
PD16
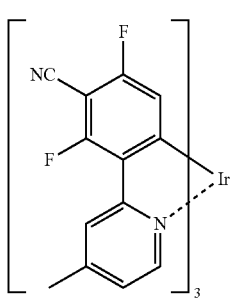
PD17
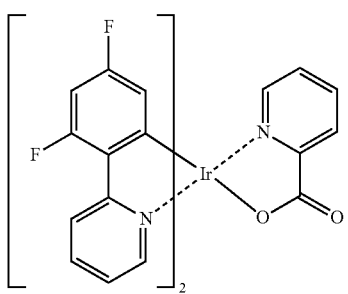
PD18
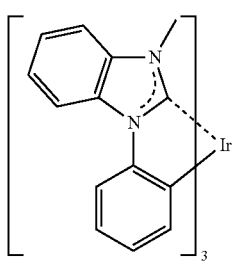
PD19
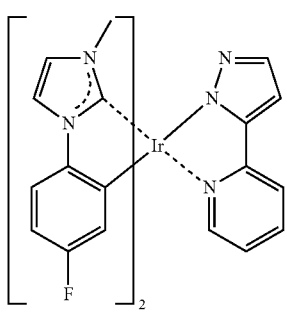
-continued
PD20
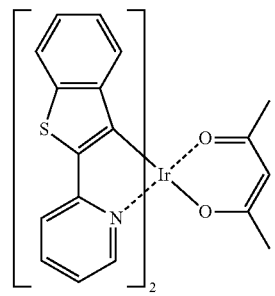
PD21
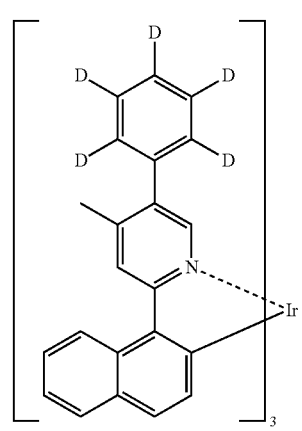
PD22
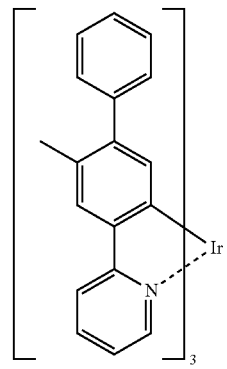
PD23
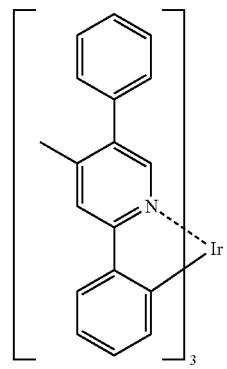

-continued

PD24

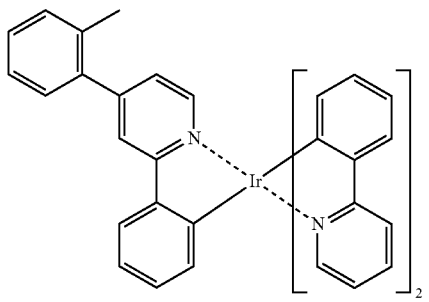

PD25

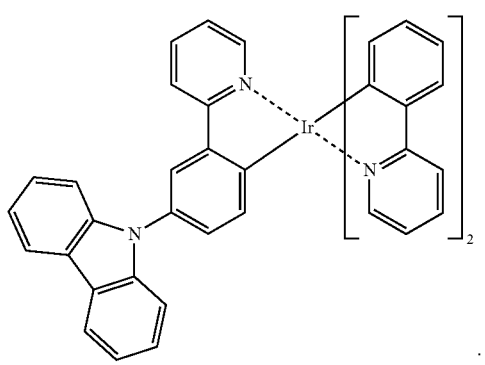

The fluorescent dopant may include an arylamine compound or a styrylamine compound.

In some embodiments, the fluorescent dopant may include a compound represented by Formula 501:

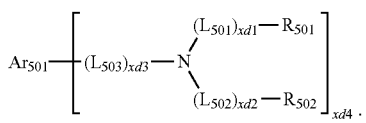

Formula 501

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer from 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer from 1 to 6.

In some embodiments, $Ar_{501}$ in Formula 501 may be selected from a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, $L_{501}$ to $L_{503}$ in Formula 501 may each independently be selected from a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

According to some embodiments, $R_{501}$ and $R_{502}$ in Formula 501 may each independently be selected from a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2.

In some embodiments, the fluorescent dopant may be selected from Compounds FD1 to FD22:

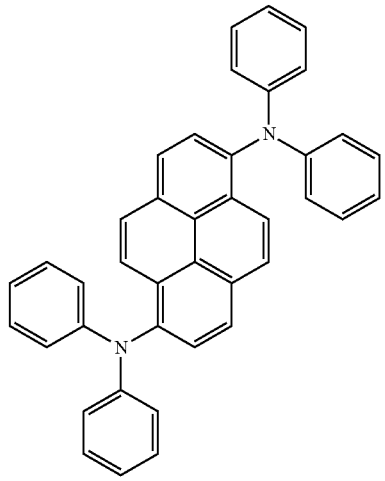
FD1

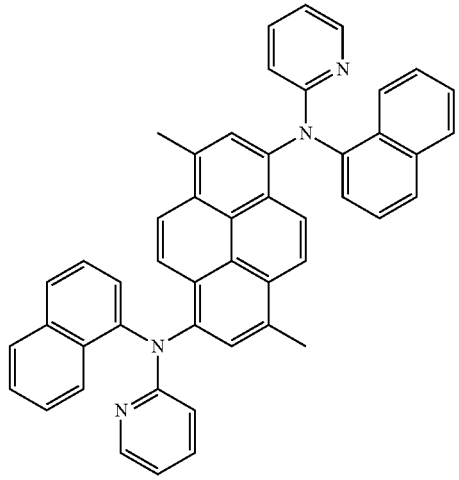
FD2

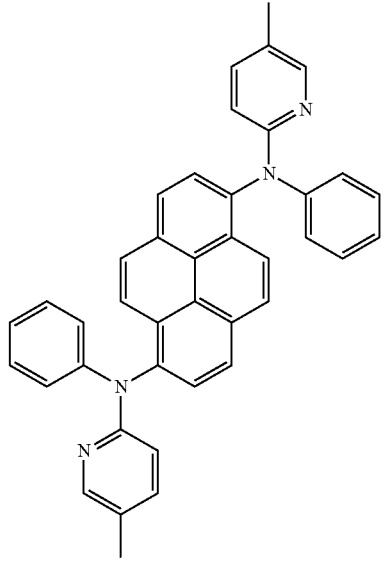
FD3

FD4
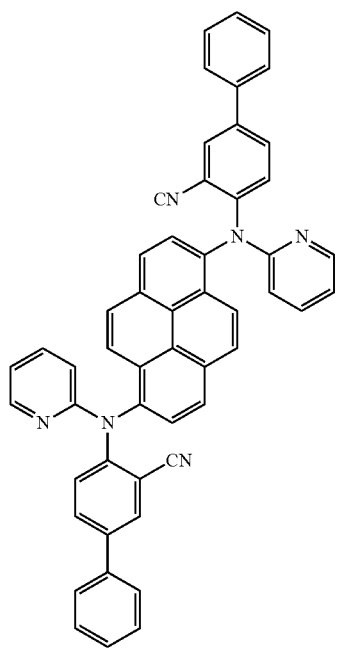
FD7
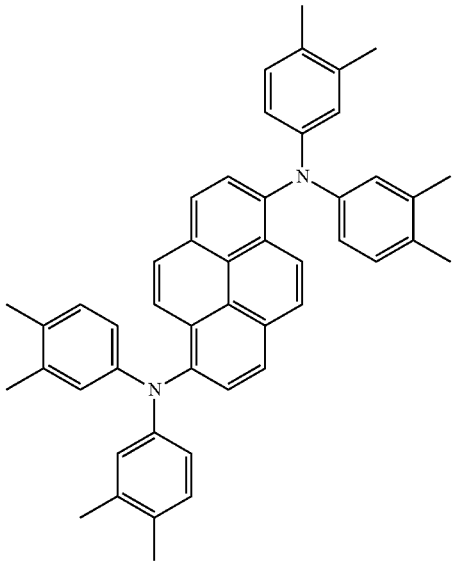
FD5
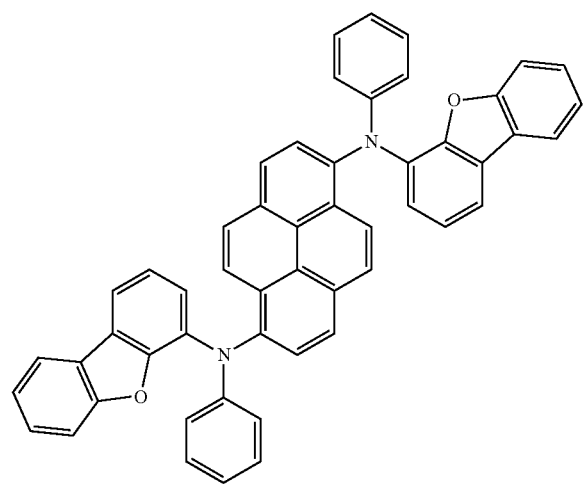
FD8
FD6
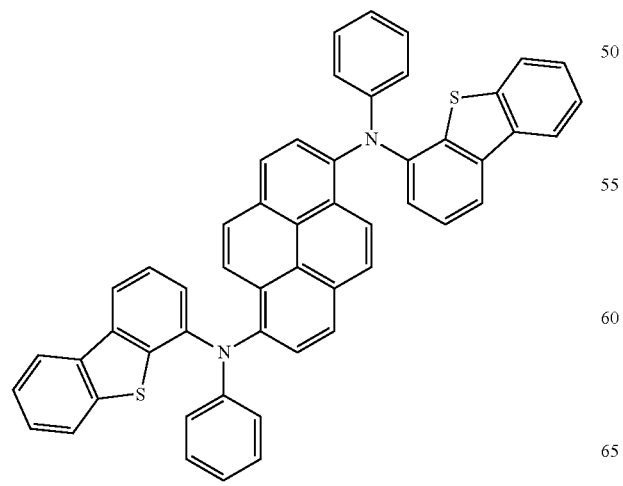
FD9
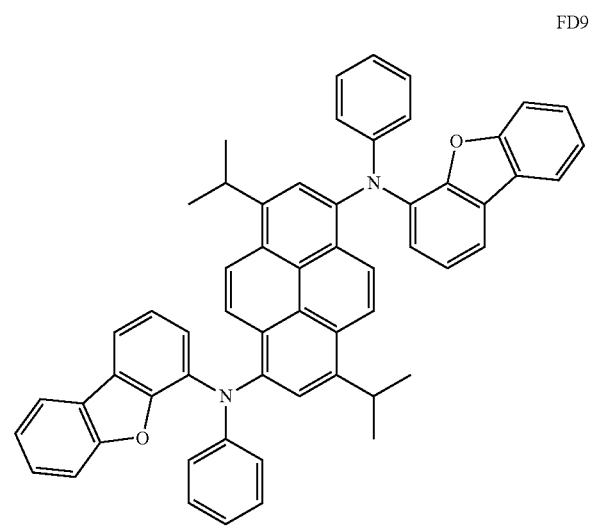

-continued
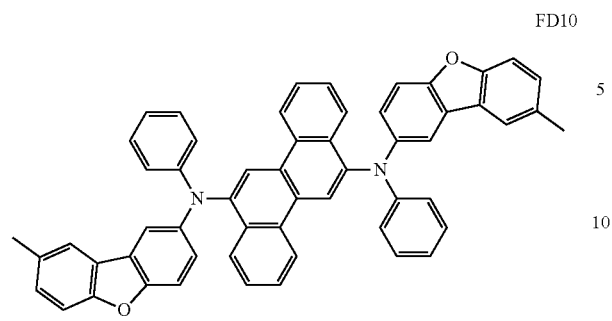
FD10
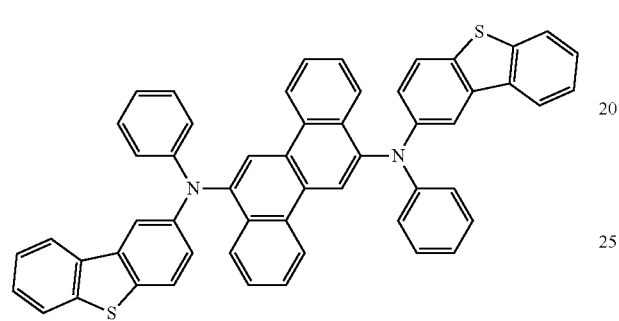
FD11
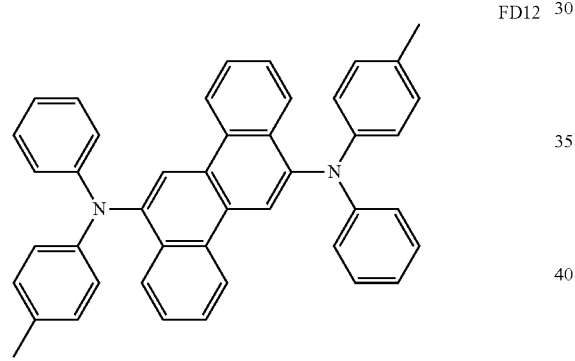
FD12
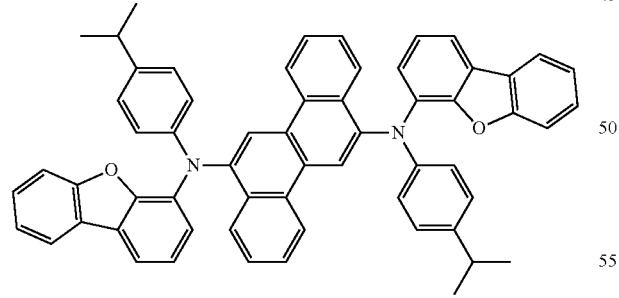
FD13
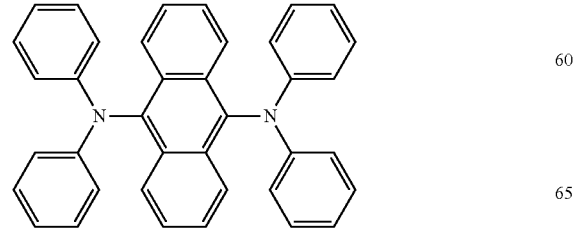
FD14
-continued
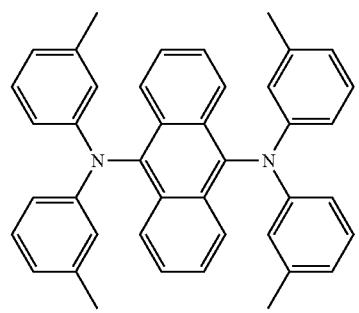
FD15
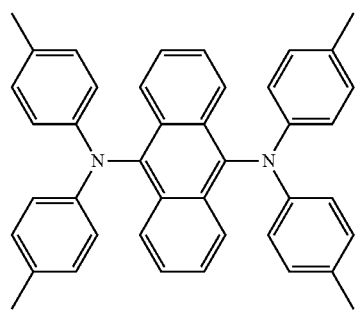
FD16
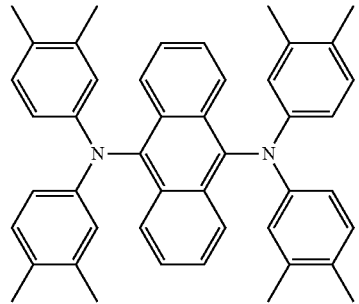
FD17
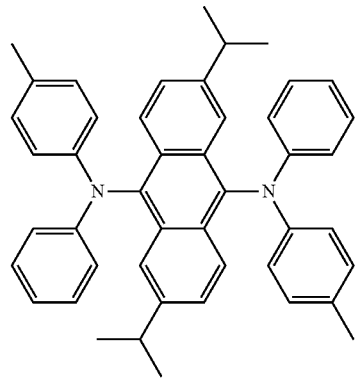
FD18

-continued
FD19
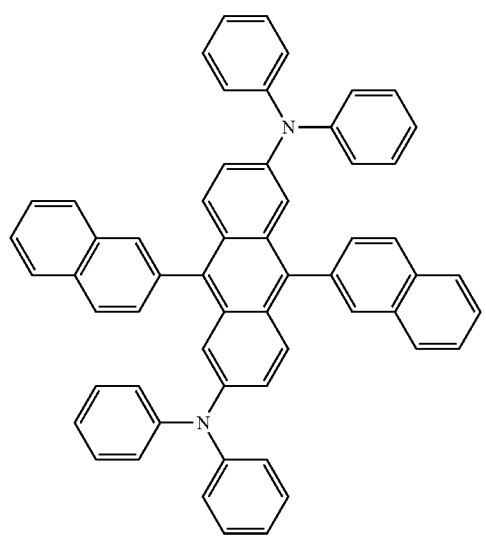
FD20
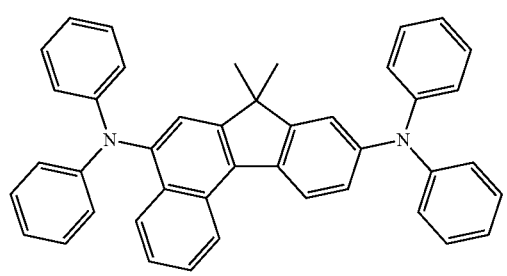
-continued
FD21
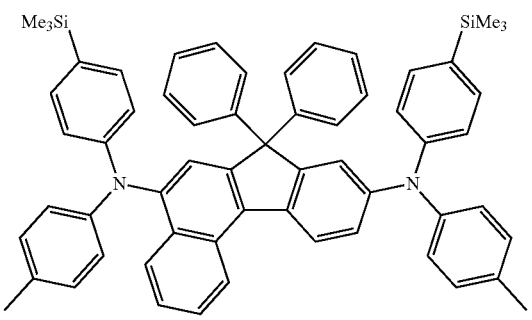
FD22
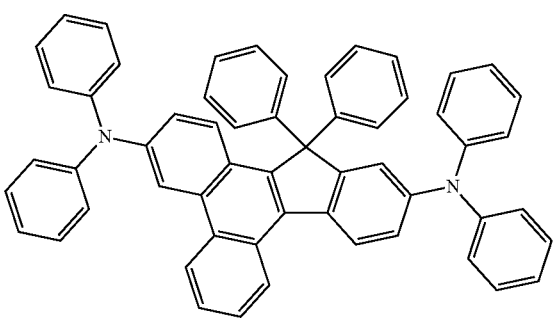
In some embodiments, the fluorescent dopant may be selected from the following compounds:
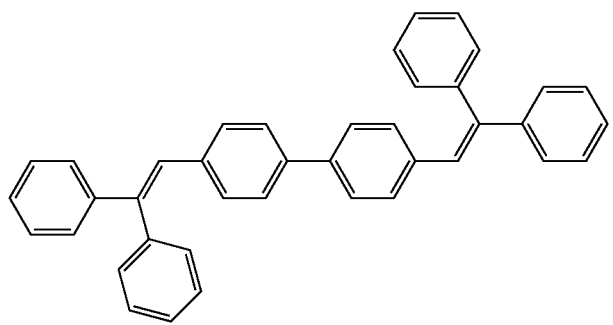
DPVBi
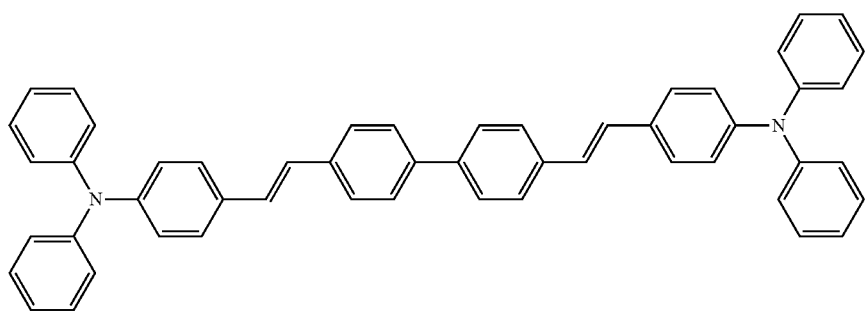
DPAVBi

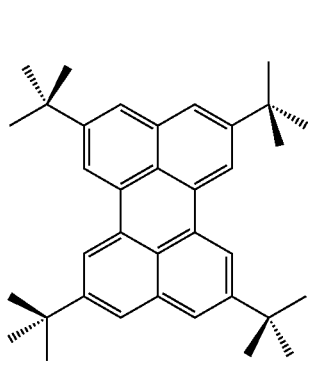
TBPe

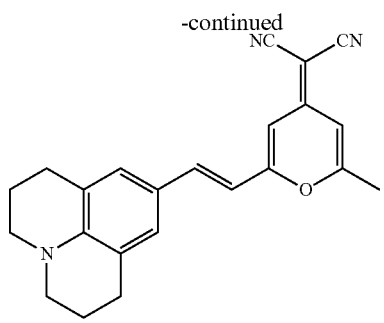
DCM

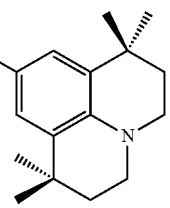
DCJTB

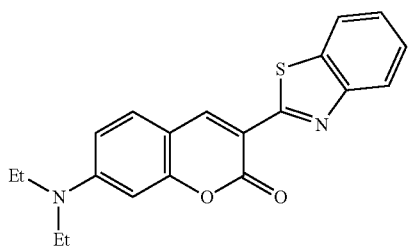
Coumarin 6

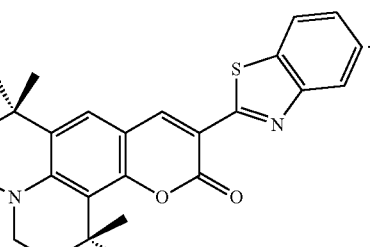
C545T

The electron transport region may have i) a single-layered structure including a single layer including a single material, ii) a single-layered structure including a single layer including a plurality of different materials, or iii) a multi-layered structure each having a plurality of layers, each having a plurality of different materials.

The electron transport region may include at least one selected from a buffer layer, a hole blocking layer, an electron control layer, an electron transport layer, and an electron injection layer.

In some embodiments, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein layers of each structure are sequentially stacked on the emission layer in each stated order.

The electron transport region, e.g., a buffer layer, a hole blocking layer, an electron control layer, or an electron transport layer in the electron transport region, may include a metal-free compound. The metal-free compound may include at least one π electron-depleted nitrogen-containing ring.

The "π electron-depleted nitrogen-containing ring" may indicate a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups, each having at least one *—N=*' moiety are condensed, or iii) a heteropolycyclic group in which at least one of 5-membered to 7-membered heteromonocyclic group, each having at least one *—N=*' moiety, is condensed with at least one $C_5$-$C_{60}$ carbocyclic group.

Examples of the π electron-depleted nitrogen-containing ring may include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an iso-benzothiazole, a benzoxazole, an isobenzoxazole, a triazole, a tetrazole, an oxadiazole, a triazine, a thiadiazole, an imidazopyridine, an imidazopyrimidine, and an azacarbazole.

For example, the electron transport region may include, in addition to the heterocyclic compound represented by Formula 1, a compound represented by Formula 601:

$$[Ar_{601}]_{xe11}\text{-}[(L_{601})_{xe1}\text{-}R_{601}]_{xe21}.$$ Formula 601

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), wherein $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In some embodiments, at least one selected from the xe11 $Ar_{601}$(s) and the xe21 $R_{601}$(s) may include a π electron-depleted nitrogen-containing ring.

In some embodiments, in Formula 601, $Ar_{601}$ may be selected from a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is 2 or greater, at least two $Ar_{601}$(s) may be bound via a single bond.

In one embodiment, in Formula 601, $Ar_{601}$ may be an anthracene group.

In some embodiments, the compound represented by Formula 601 may be represented by Formula 601-1:

Formula 601-1

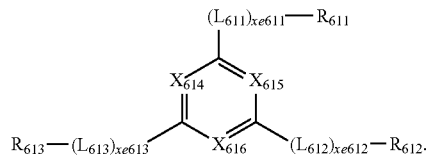

In Formula 601-1, $X_{614}$ may be N or C($R_{614}$), $X_{615}$ may be N or C($R_{615}$), $X_{616}$ may be N or C($R_{616}$), and at least one selected from $X_{614}$ to $X_{616}$ may be N, $L_{611}$ to $L_{613}$ may each independently be substantially the same as those described herein with reference to $L_{601}$, xe611 to xe613 may each independently be substantially the same as those described herein with reference to xe1, $R_{611}$ to $R_{613}$ may each independently be substantially the same as those described herein with reference to $R_{601}$, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, in Formulae 601 and 601-1, $L_{601}$ and $L_{601}$ to $L_{613}$ may each be independently selected from a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group.

In one or more embodiments, xe1 and xe611 to xe613 in Formulae 601 and 601-1 may each independently be 0, 1, or 2.

In some embodiments, $R_{601}$ to $R_{611}$ and $R_{613}$ in Formulae 601 and 601-1 may each independently be selected from a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), wherein Q$_{601}$ and Q$_{602}$ may each independently be substantially the same as those described herein.

The electron transport region may include at least one compound selected from Compounds ET1 to ET36:

ET1

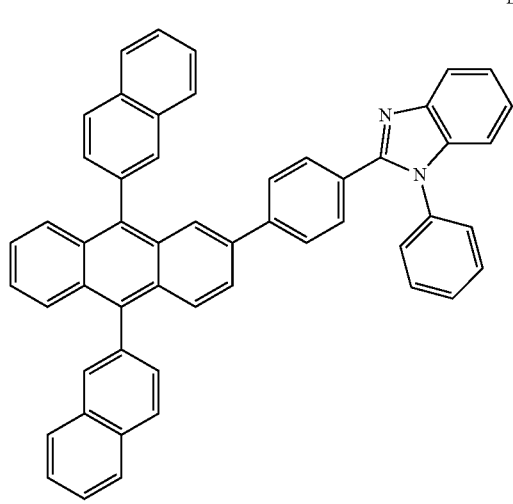

ET2

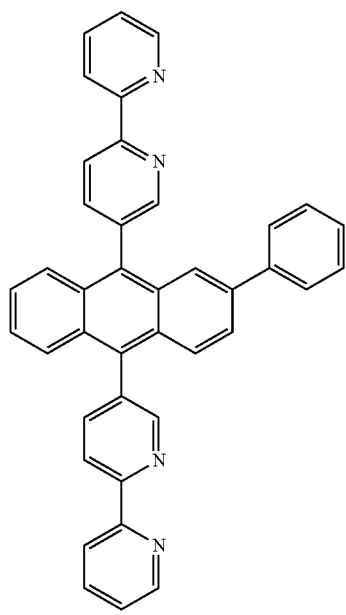

ET3

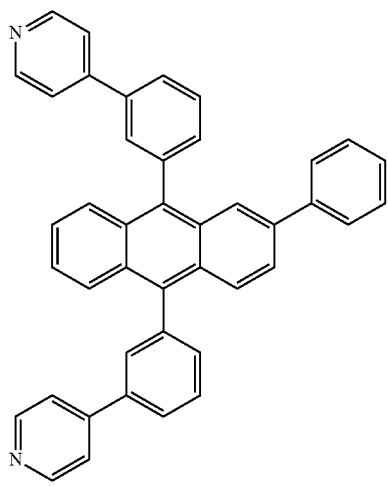

ET4

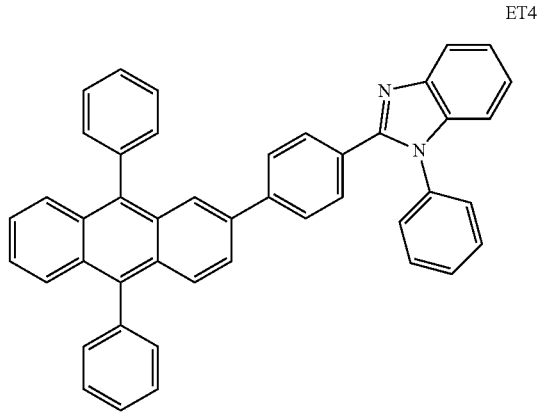

ET5

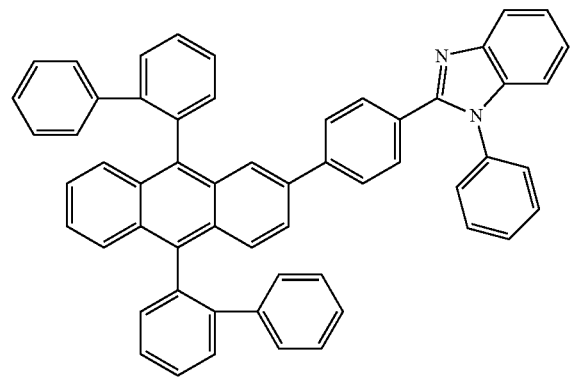

111
-continued
ET6
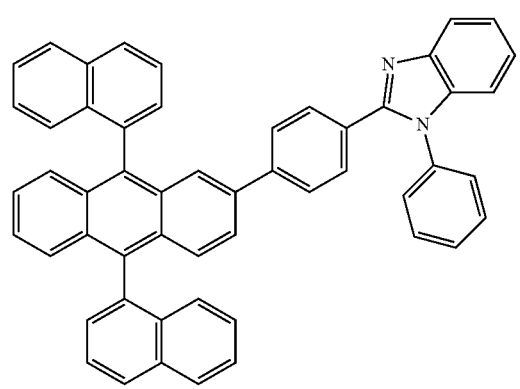
ET7
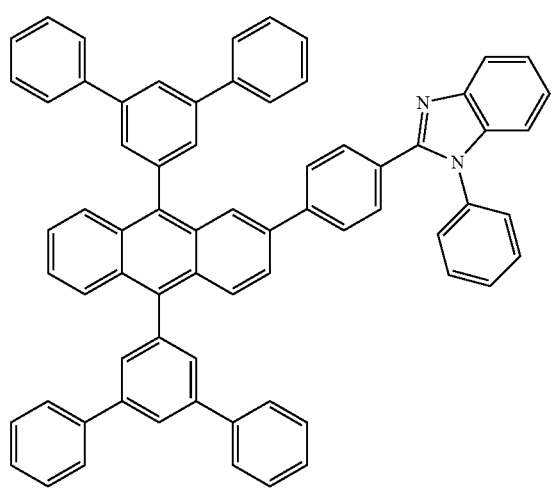
ET8
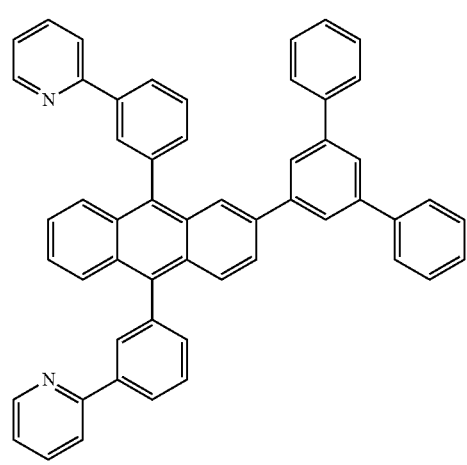
112
-continued
ET9
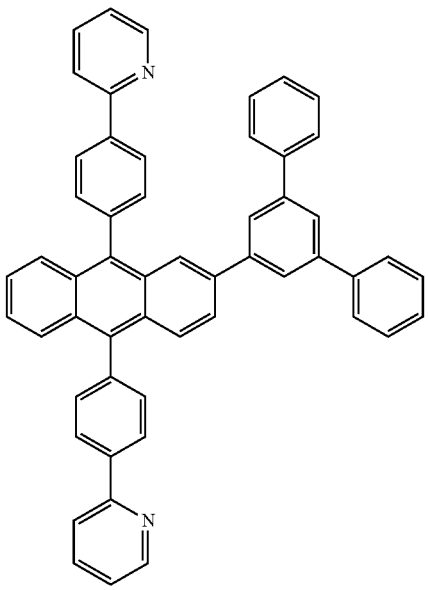
ET10
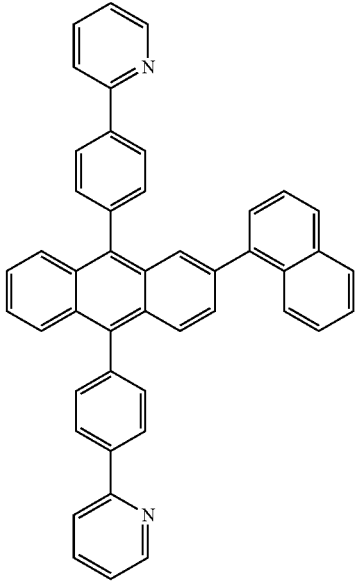
ET11

ET12
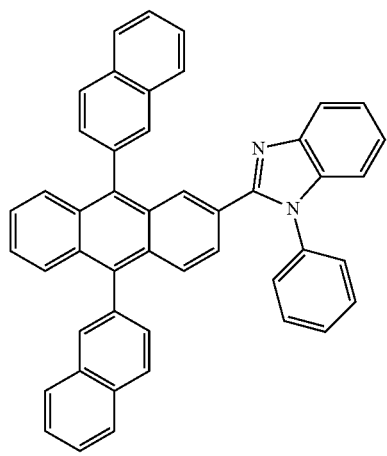
ET13
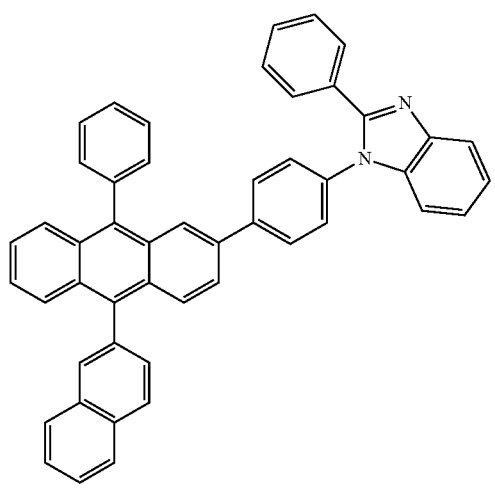
ET14
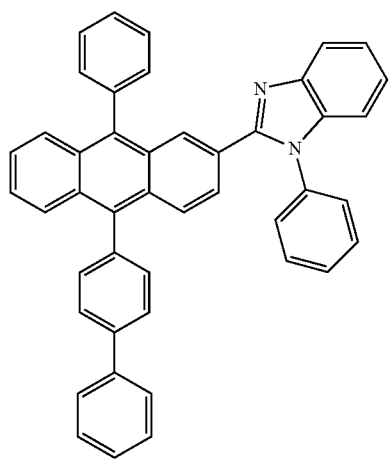
ET15
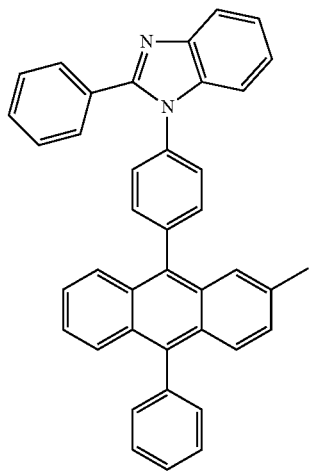
ET16
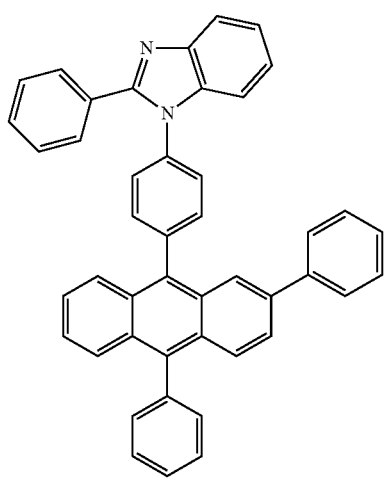
ET17
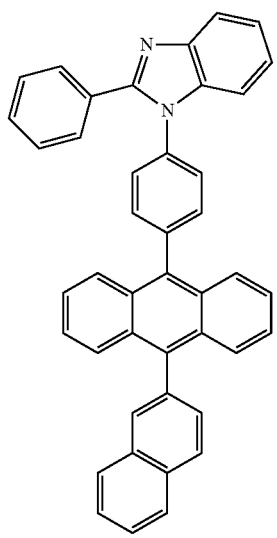

ET18
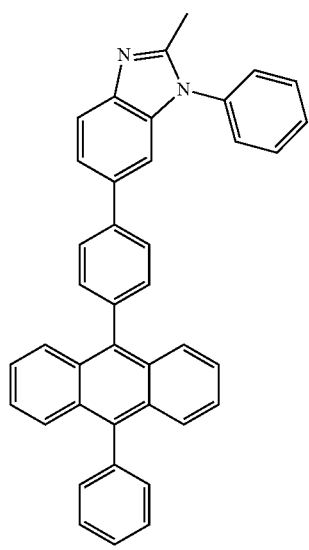
ET21
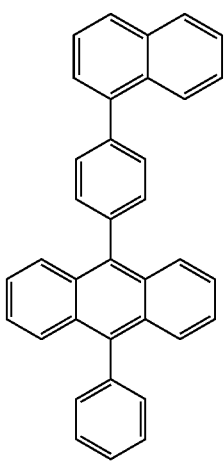
ET19
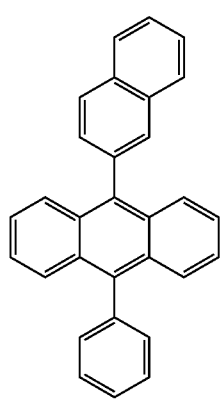
ET22
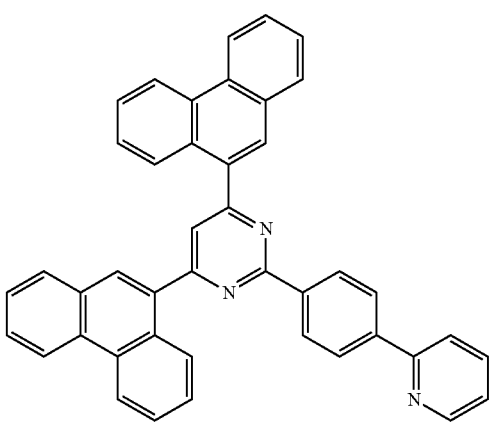
ET20
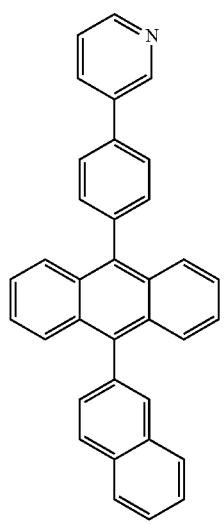
ET23
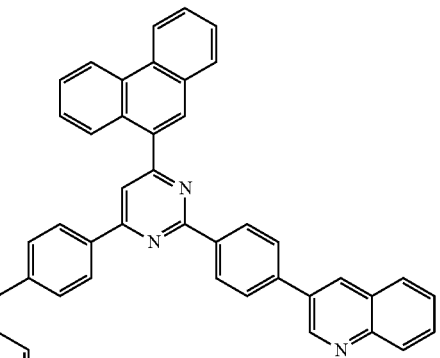

ET24
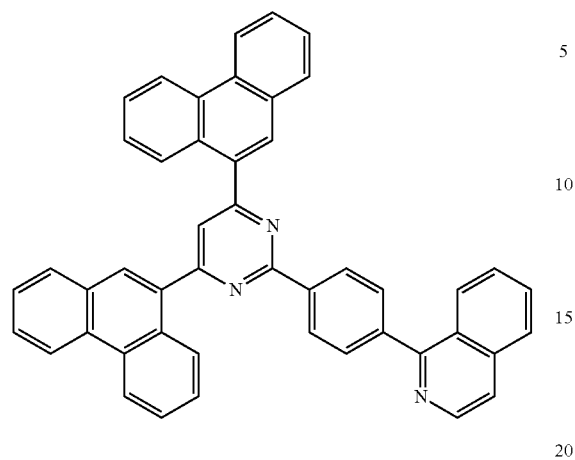
ET27
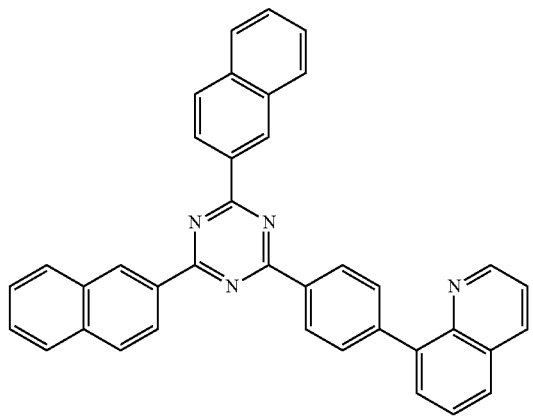
ET25
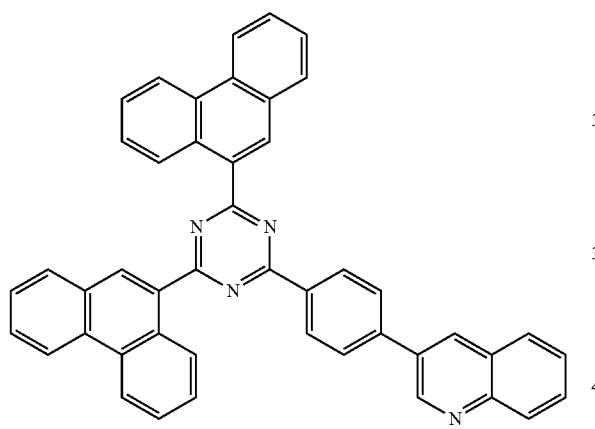
ET28
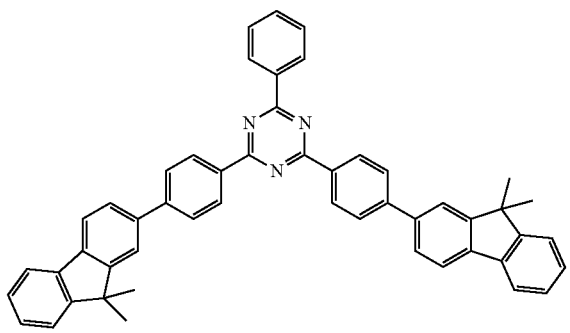
ET26
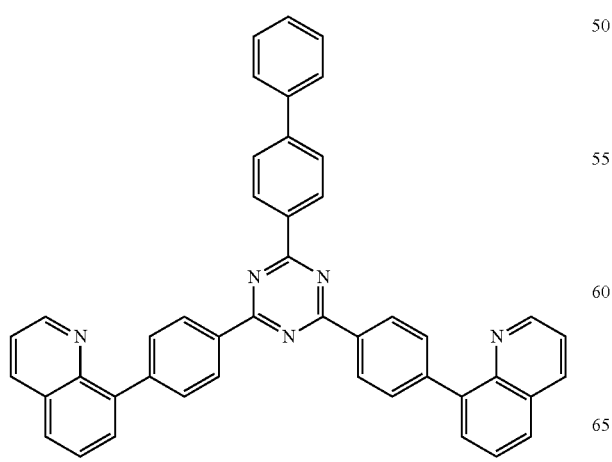
ET29
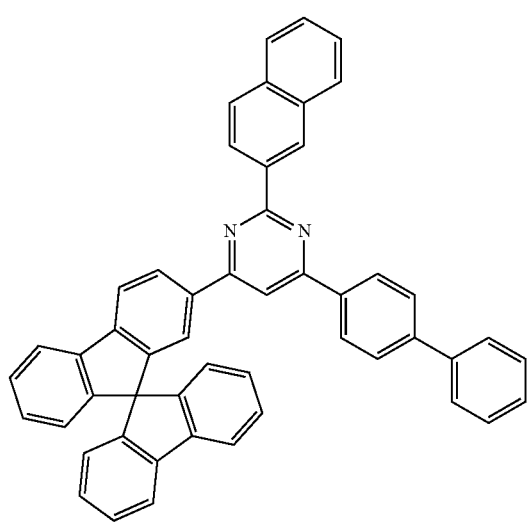

ET30
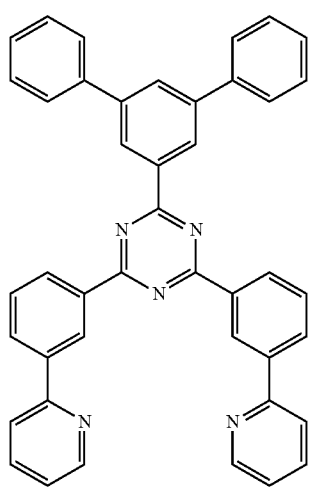
ET31
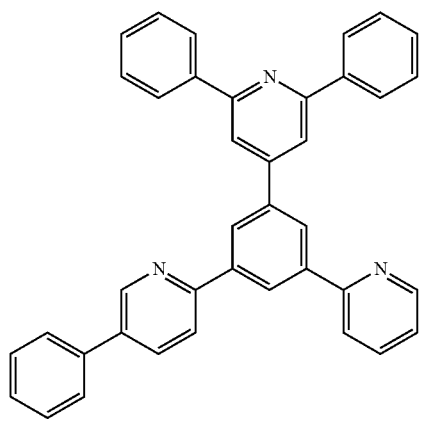
ET32
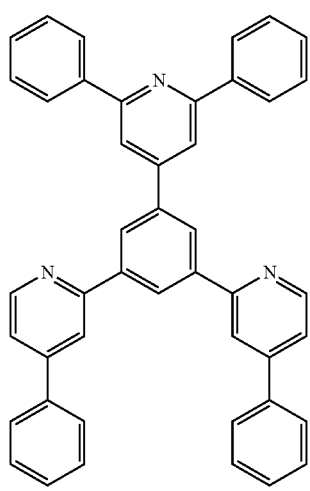
ET33
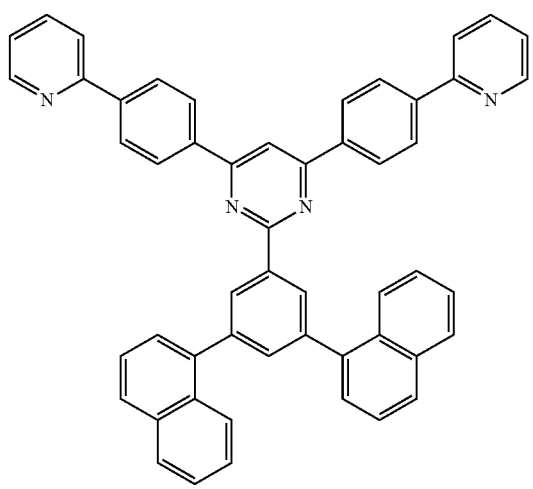
ET34
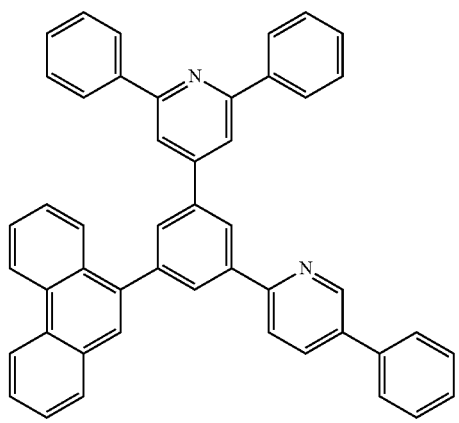
ET35
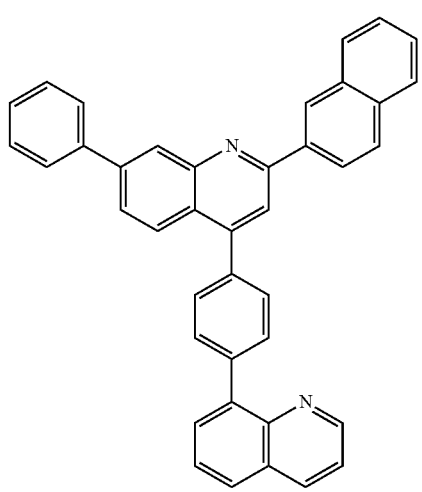

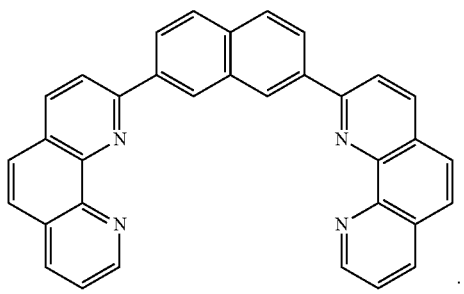

ET36

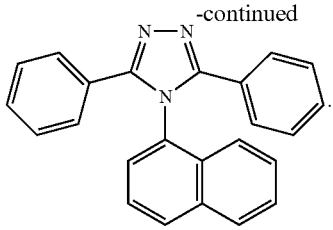

NTAZ

In one or more embodiments, the electron transport region may include at least one selected from 2,9-dimethyl-4,7-diphenyl-1,10-phenanthroline (BCP), 4,7-dphenyl-1,10-phenanthroline (Bphen), Alq₃, BAlq, 3-(biphenyl-4-yl)-5-(4-tert-butylphenyl)-4-phenyl-4H-1,2,4-triazole (TAZ), and NTAZ:

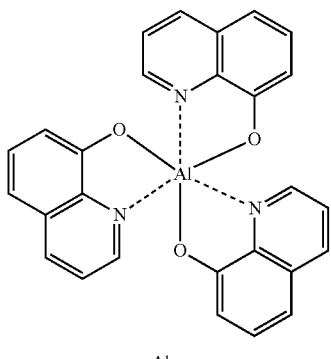

Alq₃

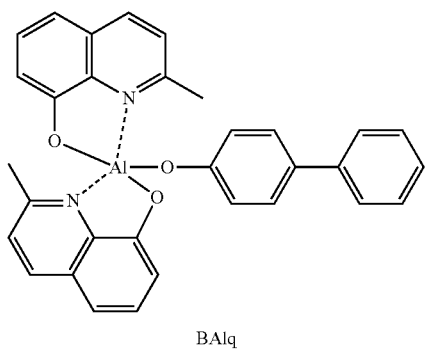

BAlq

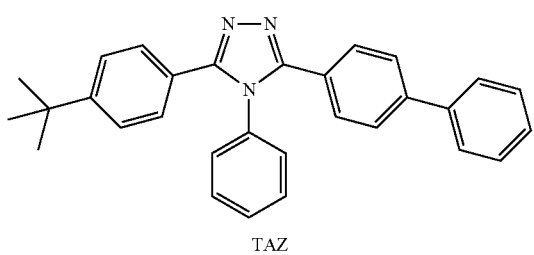

TAZ

The thickness of the buffer layer, the hole blocking layer, or the electron control layer may each independently be in a range of about 20 Å to about 1,000 Å, e.g., about 30 Å to about 300 Å. When the thicknesses of the buffer layer, the hole blocking layer or the electron control layer are within any of these ranges, excellent hole blocking characteristics or excellent electron controlling characteristics may be obtained without a substantial increase in driving voltage.

The thickness of the electron transport layer may be in a range of about 100 Å to about 1,000 Å, e.g., about 150 Å to about 500 Å. When the thickness of the electron transport layer is within any of these ranges, excellent electron transport characteristics may be obtained without a substantial increase in driving voltage.

The electron transport region (e.g., the electron transport layer in the electron transport region) may further include, in addition to the materials described above, a material including metal.

The material including metal may include at least one selected from an alkali metal complex and an alkaline earth metal complex. The alkali metal complex may include a metal ion selected from a lithium (Li) ion, a sodium (Na) ion, a potassium (K) ion, a rubidium (Rb) ion, and a cesium (Cs) ion. The alkaline earth metal complex may include a metal ion selected from a beryllium (Be) ion, a magnesium (Mg) ion, a calcium (Ca) ion, an strontium (Sr) ion, and a barium (Ba) ion. Each ligand coordinated with the metal ion of the alkali metal complex and the alkaline earth metal complex may independently be selected from a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxydiphenyl oxadiazole, a hydroxydiphenyl thiadiazole, a hydroxyphenyl pyridine, a hydroxyphenyl benzimidazole, a hydroxyphenyl benzothiazole, a bipyridine, a phenanthroline, and a cyclopentadiene.

For example, the material including metal may include a Li complex. The Li complex may include, e.g., Compound ET-D1 (lithium quinolate, LiQ) or ET-D2:

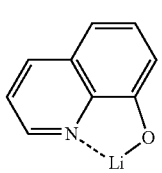

ET-D1

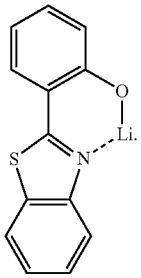

ET-D2

The electron transport region may include an electron injection layer that facilitates injection of electrons from the second electrode 190. The electron injection layer may be in direct contact with the second electrode 190.

The electron injection layer may have i) a single-layered structure including a single layer including a single material, ii) a single-layered structure including a single layer including a plurality of different materials, or iii) a multi-layered structure having a plurality of layers, each including a plurality of different materials.

The electron injection layer may include an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof.

The alkali metal may be selected from Li, Na, K, Rb, and Cs. In one embodiment, the alkali metal may be Li, Na, or Cs. In one or more embodiments, the alkali metal may be Li or Cs.

The alkaline earth metal may be selected from Mg, Ca, Sr, and Ba.

The rare earth metal may be selected from Sc, Y, Ce, Yb, Gd, and Tb.

The alkali metal compound, the alkaline earth metal compound, and the rare earth metal compound may each independently be selected from oxides and halides (e.g., fluorides, chlorides, bromides, or iodines) of the alkali metal, the alkaline earth metal, and the rare earth metal, respectively.

The alkali metal compound may be selected from alkali metal oxides, such as $Li_2O$, $Cs_2O$, or $K_2O$, and alkali metal halides, such as LiF, NaF, CsF, KF, LiI, NaI, CsI, KI, or RbI. In one embodiment, the alkali metal compound may be selected from LiF, $Li_2O$, NaF, LiI, NaI, CsI, and KI.

The alkaline earth metal compound may be selected from alkaline earth metal compounds, such as BaO, SrO, CaO, $Ba_xSr_{1-x}O$ (wherein 0<x<1), and $Ba_xCa_{1-x}O$ (wherein 0<x<1). In one embodiment, the alkaline earth metal compound may be selected from BaO, SrO, and CaO.

The rare earth metal compound may be selected from $YbF_3$, $ScF_3$, $ScO_3$, $Y_2O_3$, $Ce_2O_3$, $GdF_3$, and $TbF_3$. In one embodiment, the rare earth metal compound may be selected from $YbF_3$, $ScF_3$, $TbF_3$, $YbI_3$, $ScI_3$, and $TbI_3$.

The alkali metal complex, the alkaline earth metal complex, and the rare earth metal complex may each include ions of the above-described alkali metal, alkaline earth metal, and rare earth metal. Each ligand coordinated with the metal ion of the alkali metal complex, the alkaline earth metal complex, and the rare earth metal complex may independently be selected from a hydroxyquinoline, a hydroxyisoquinoline, a hydroxybenzoquinoline, a hydroxyacridine, a hydroxyphenanthridine, a hydroxyphenyl oxazole, a hydroxyphenyl thiazole, a hydroxydiphenyl oxadiazole, a hydroxydiphenyl thiadiazole, a hydroxyphenyl pyridine, a hydroxyphenyl benzimidazole, a hydroxyphenyl benzothiazole, a bipyridine, a phenanthroline, and a cyclopentadiene.

The electron injection layer may consist of an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof, as described above. In some embodiments, the electron injection layer may further include an organic material. When the electron injection layer further includes an organic material; the alkali metal, the alkaline earth metal, the rare earth metal, the alkali metal compound, the alkaline earth metal compound, the rare earth metal compound, the alkali metal complex, the alkaline earth metal complex, the rare earth metal complex, or a combination thereof may be homogeneously or non-homogeneously dispersed in a matrix including the organic material.

The thickness of the electron injection layer may be in a range of about 1 Å to about 100 Å, e.g., about 3 Å to about 90 Å. When the thickness of the electron injection layer is within any of these ranges, excellent electron injection characteristics may be obtained without a substantial increase in driving voltage.

The second electrode 190 may be disposed on the organic layer 150. The second electrode 190 may be a cathode that is an electron injection electrode. A material for forming the second electrode 190 may be a material with a low work function, for example, a metal, an alloy, an electrically conductive compound, or a mixture thereof.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO. The second electrode 190 may be a transmissive electrode, a semi-transmissive electrode, or a reflective electrode.

The second electrode 190 may have a single-layered structure, or a multi-layered structure including two or more layers.

Figure 2:
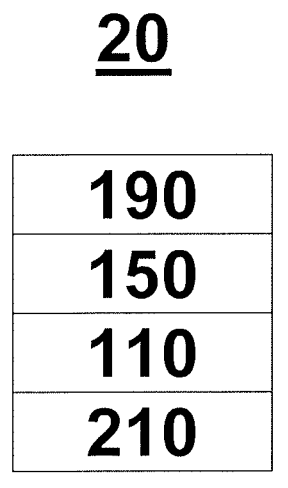
Figure 3:
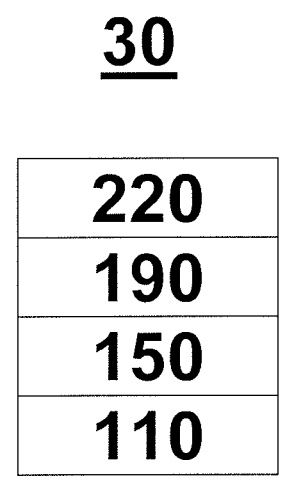
Figure 4:
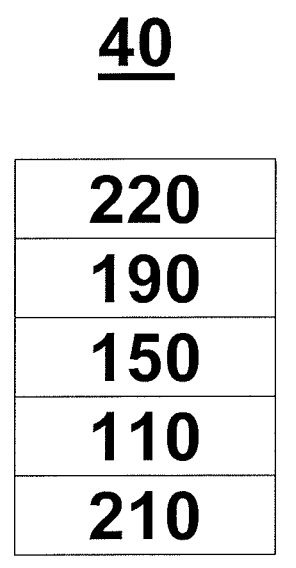

Referring to FIG. 2, an organic light-emitting device 20 has a first capping layer 210, the first electrode 110, the organic layer 150, and the second electrode 190 structure, wherein the layers are sequentially stacked in this stated order. Referring to FIG. 3, an organic light-emitting device 30 has the first electrode 110, the organic layer 150, the second electrode 190, and a second capping layer 220 structure, wherein the layers are sequentially stacked in this stated order. Referring to FIG. 4, an organic light-emitting device 40 has the first capping layer 210, the first electrode 110, the organic layer 150, the second electrode 190, and the second capping layer 220 structure, wherein the layers are stacked in this stated order.

The first electrode 110, the organic layer 150, and the second electrode 190 illustrated in FIGS. 2 to 4 may be substantially the same as those illustrated in FIG. 1.

In the organic light-emitting devices 20 and 40, light emitted from the emission layer in the organic layer 150 may pass through the first electrode 110 (which may be a semi-transmissive electrode or a transmissive electrode) and through the first capping layer 210 to the outside. In the organic light-emitting devices 30 and 40, light emitted from the emission layer in the organic layer 150 may pass through the second electrode 190 (which may be a semi-transmissive electrode or a transmissive electrode) and through the second capping layer 220 to the outside.

The first capping layer 210 and the second capping layer 220 may improve the external luminous efficiency based on the principle of constructive interference.

The first capping layer 210 and the second capping layer 220 may each independently be a capping layer including an organic material, an inorganic capping layer including an inorganic material, or a composite capping layer including an organic material and an inorganic material.

At least one selected from the first capping layer 210 and the second capping layer 220 may each independently include at least one material selected from carbocyclic compounds, heterocyclic compounds, amine-based compounds, porphine derivatives, phthalocyanine derivatives, naphthalocyanine derivatives, alkali metal complexes, and alkaline earth metal complexes. The carbocyclic compound, the heterocyclic compound, and the amine-based compound may optionally be substituted with a substituent containing at least one element selected from O, N, S, Se, Si, F, Cl, Br, and I. In one embodiment, at least one of the first capping layer 210 and the second capping layer 220 may each independently include an amine-based compound.

In one or more embodiments, at least one of the first capping layer 210 and the second capping layer 220 may each independently include a compound represented by Formula 201 or 202.

In one or more embodiments, at least one selected from the first capping layer 210 and the second capping layer 220 may each independently include a compound selected from Compounds HT28 to HT33 and Compound CP1 to CP5:

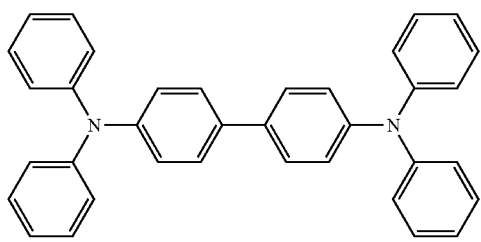
CP1

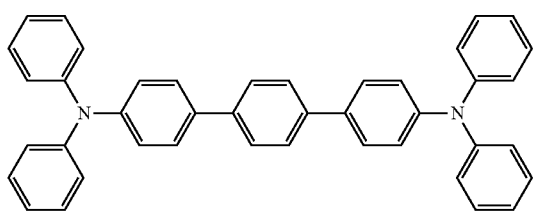
CP2

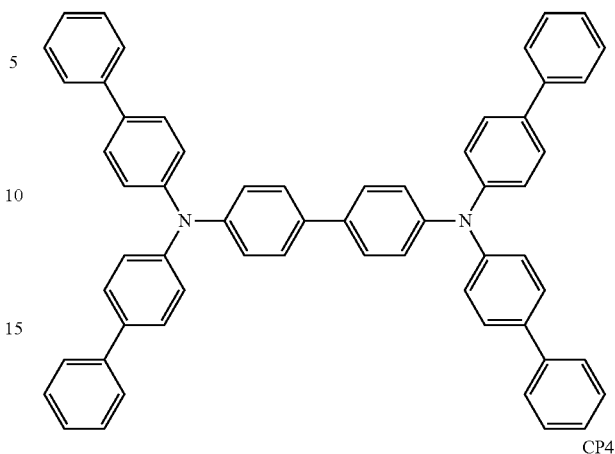
CP3

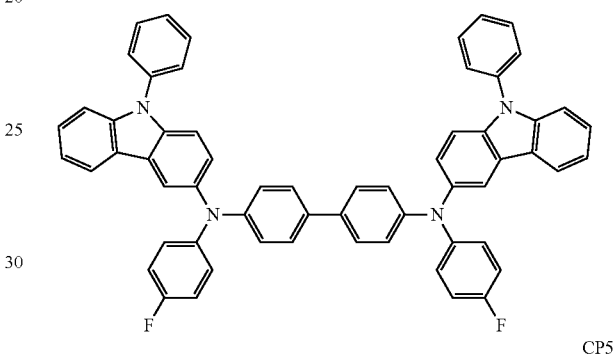
CP4

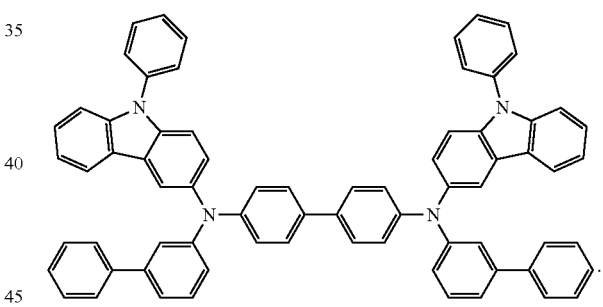
CP5

Layers constituting the hole transport region, an emission layer, and layers constituting the electron transport region may be formed in a certain region by using one or more suitable methods such as vacuum deposition, spin coating, casting, Langmuir-blodgett (LB) deposition, ink-jet printing, laser printing, and laser-induced thermal imaging.

When layers constituting the hole transport region, an emission layer, and layers constituting the electron transport region are each independently formed by vacuum deposition, the vacuum deposition may be performed at a temperature in a range of about 100° C. to about 500° C. at a vacuum degree in a range of about $10^{-8}$ torr to about $10^{-3}$ torr, and/or at a rate in a range of about 0.01 Angstroms per second (Å/sec) to about 100 Å/sec, depending on the compound to be included in each layer and the structure of each layer to be formed.

When layers constituting the hole transport region, the emission layer, and layers constituting the electron transport region are each independently formed by spin coating, the spin coating may be performed at a coating rate of about 2,000 revolutions per minute (rpm) to about 5,000 rpm, and at a heat treatment temperature of about 80 to about 200° C., depending on the compound to be included in each layer and the structure of each layer to be formed.

The term "$C_1$-$C_{60}$ alkyl group" as used herein refers to a linear or branched aliphatic hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a hydrocarbon group having at least one carbon-carbon double bond in the middle or at the terminus of the $C_2$-$C_{60}$ alkyl group. Examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group. Examples thereof include an ethynyl group and a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (where $A_{101}$ is a $C_1$-$C_{60}$ alkyl group). Examples thereof include a methoxy group, an ethoxy group, and an isopropyloxy group.

The term "$C_3$-$C_{10}$ cycloalkyl group" as used herein refers to a monovalent saturated hydrocarbon monocyclic group including 3 to 10 carbon atoms. Examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent monocyclic group including at least one heteroatom selected from N, O, Si, P, and S as a ring-forming atom and 1 to 10 carbon atoms. Examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one double bond in its ring, and is not aromatic. Examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group including at least one heteroatom selected from N, O, Si, P, and S as a ring-forming atom, 1 to 10 carbon atoms, and at least one double bond in its ring. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkylene group" as used herein refers to a divalent group having the same structure as the $C_1$-$C_{10}$ heterocycloalkyl group.

The term "$C_6$-$C_{60}$ aryl group" as used herein refers to an aromatic monovalent group having 6 to 60 carbon atoms. The term "$C_6$-$C_{60}$ arylene group" as used herein refers to an aromatic divalent group having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each independently include two or more rings, the respective rings may be fused.

The term "$C_1$-$C_{60}$ heteroaryl group" as used herein refers to a monovalent group having a heterocyclic aromatic system that has at least one heteroatom selected from N, O, Si, P, and S as a ring-forming atom and 1 to 60 carbon atoms. The term "$C_1$-$C_{60}$ heteroarylene group" as used herein refers to a divalent group having a heterocyclic aromatic system including at least one heteroatom selected from N, O, P, and S as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each independently include two or more rings, the respective rings may be fused.

The term "$C_6$-$C_{60}$ aryloxy group" as used herein refers to a group represented by —$OA_{102}$ (where $A_{102}$ is a $C_6$-$C_{60}$ aryl group). The term "$C_6$-$C_{60}$ arylthio group" as used herein refers to a group represented by —$SA_{103}$ (where $A_{103}$ is a $C_6$-$C_{60}$ aryl group).

The term "monovalent non-aromatic condensed polycyclic group" as used herein refers to a monovalent group that has two or more rings condensed and only carbon atoms (e.g., 8 to 60 carbon atoms) as ring forming atoms, wherein the entire molecular structure is non-aromatic. An example of the monovalent non-aromatic condensed polycyclic group is a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group that has two or more condensed rings and at least one heteroatom selected from N, O, Si, P, and S, in addition to carbon atoms (for example, 1 to 60 carbon atoms), as a ring-forming atom, wherein the entire molecular structure is non-aromatic. An example of the monovalent non-aromatic condensed heteropolycyclic group is a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{60}$ carbocyclic group" as used herein refers to a monocyclic or polycyclic group having 5 to 60 carbon atoms only as ring-forming atoms. The term "$C_5$-$C_{60}$ carbocyclic group" as used herein refers to an aromatic carbocyclic group or a non-aromatic carbocyclic group. The term "$C_5$-$C_{60}$ carbocyclic group" as used herein refers to a ring (such as a benzene group), a monovalent group (such as a phenyl group), or a divalent group (such as a phenylene group). In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having the same structure as the $C_1$-$C_{60}$ carbocyclic group, except that at least one heteroatom selected from N, O, Si, P, and S is used as a ring-forming atom, in addition to carbon atoms (e.g., 1 to 60 carbon atoms).

In the present specification, at least one substituent of the substituted $C_5$-$C_{60}$ carbocyclic group, substituted $C_1$-$C_{60}$ heterocyclic group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, a substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_1$ to $Q_6$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph" as used herein refers to a phenyl group. The term "Me" as used herein refers to a methyl group. The term "Et" as used herein refers to an ethyl group. The term "ter-Bu" or "Bu$^t$" as used herein refers to a tert-butyl group. The term "OMe" as used herein refers to a methoxy group.

The term "biphenyl group" as used herein refers to a phenyl group substituted with a phenyl group. In other words, the "biphenyl group" may be a substituted phenyl group having a $C_6$-$C_{60}$ aryl group as a substituent.

The term "terphenyl group" as used herein refers to a phenyl group substituted with a biphenyl group. In other words, the "terphenyl group" may be a substituted phenyl group having a $C_6$-$C_{60}$ aryl group substituted with a $C_6$-$C_{60}$ aryl group as a substituent.

The symbols * and *' as used herein, unless defined otherwise, refer to a binding site to an adjacent atom in a corresponding formula.

Hereinafter a compound and an organic light-emitting device according to one or more embodiments will be described in detail with reference to Synthesis Examples and Examples. The expression "B was used instead of A" used in describing Synthesis Examples means that an identical molar equivalent of B was used in place of A.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Synthesis Examples

Synthesis Example 1: Synthesis of Compound 1

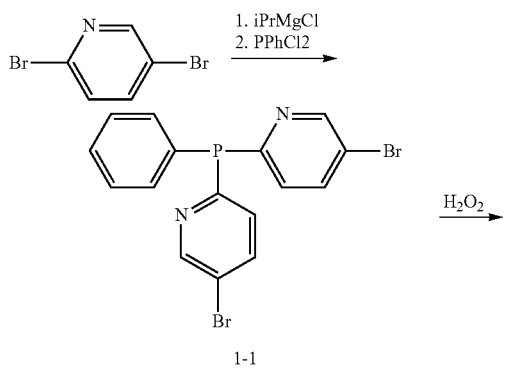

1-1

-continued

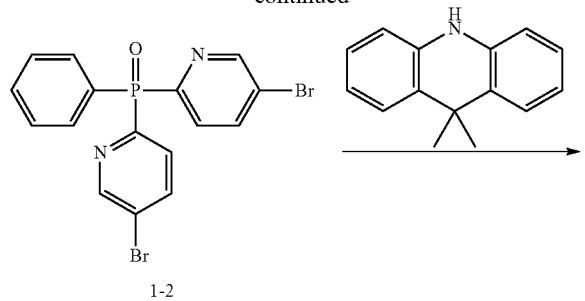

1-2

Synthesis of Intermediate 1-1

2,5-dibromopyridine was dissolved in tetrahydrofuran (THF). Isopropyl magnesium chloride was added to the solution, and the solution was stirred to obtain a Grignard reagent. Dichlorophenyl phosphine (PPhCl$_2$) was added to the Grignard reagent, and then the mixture was stirred to obtain Intermediate 1-1. Intermediate 1-1 was identified by liquid chromatography-mass spectrometry (LC-MS).

$C_{16}H_{11}Br_2N_2P$: M+1 420.8

Synthesis of Intermediate 1-2

Intermediate 1-1 was oxidized using a hydrogen peroxide solution to obtain Intermediate 1-2. Intermediate 1-2 was identified by LC-MS.

$C_{16}H_{11}Br_2N_2OP$: M+1 436.8

Synthesis of Compound 1

5.0 g of Intermediate 1-2, 5.0 g of 9,9-dimethyl-9,10-dihydroacridine (CAS No. 6267-02-3), 0.10 g of palladium (II) acetate, 0.24 g of triphenylphosphine, and 1.65 g of NaOtBu were dissolved in 50 mL of toluene, and then the resulting solution was refluxed for 3 hours. The obtained reaction solution was cooled to ambient temperature, an organic layer was extracted using ethyl acetate, and then the organic layer was washed with water. The obtained organic layer was dried by using magnesium sulfate (MgSO$_4$), a solvent was removed therefrom by evaporation, and the obtained residue was separated and purified through silica gel chromatography to thereby obtain 4.9 g of Compound 1 (yield: 62%). Compound 1 was identified by LC-MS and $^1$H-NMR.

$C_{46}H_{39}N_4OP$: M+1 695.3

$^1$H NMR (500 MHz, CDCl$_3$) δ=7.94 (d, 2H), 7.80 (s, 2H), 7.72 (d, 2H), 7.51-7.42 (m, 3H), 7.21 (d, 2H), 7.21-7.11 (m, 12H), 6.99 (t, 4H), 1.62 (s, 12).

Synthesis Example 2: Synthesis of Compound 4

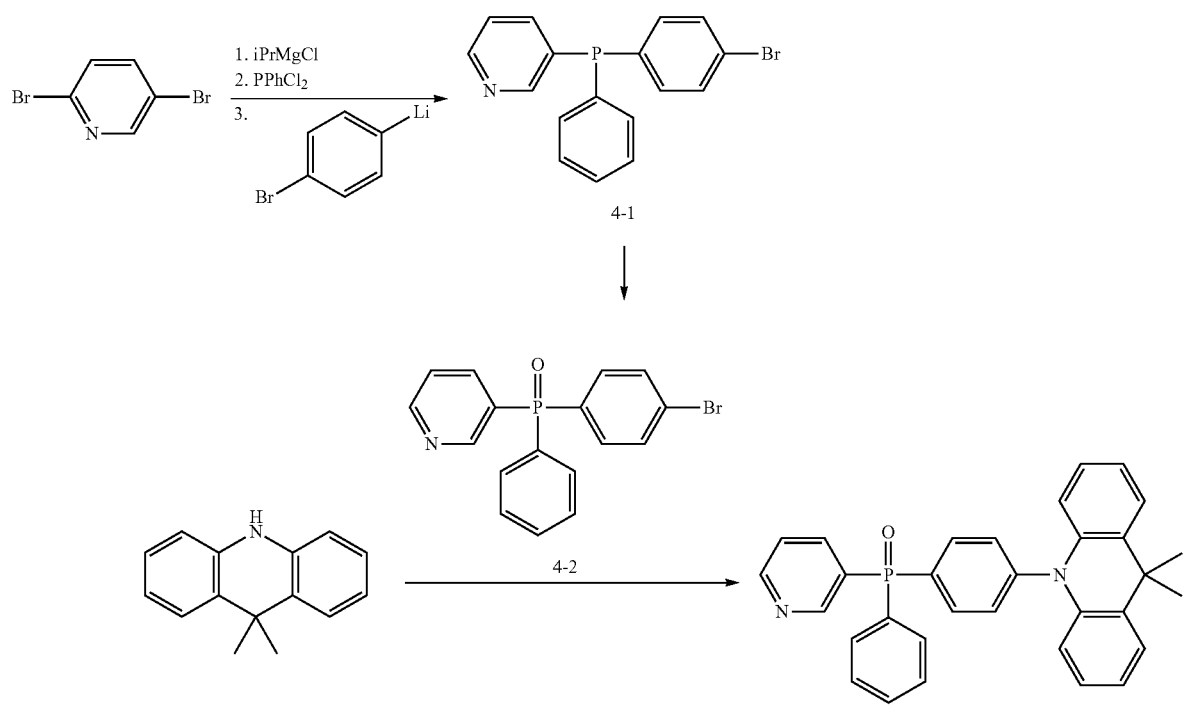

Synthesis of Intermediate 4-1

2,5-dibromopyridine was dissolved in THF, isopropyl magnesium chloride was added to the solution, and the solution was stirred to obtain a Grignard reagent. Dichlorophenyl phosphine was added to the Grignard reagent, 4-bromophenyl lithium was added to the mixture, and then the mixture was stirred continuously to obtain Intermediate 4-1. Intermediate 4-1 was identified by LC-MS.

$C_{17}H_{13}BrNP$: M+1 341.8

Synthesis of Intermediate 4-2

Intermediate 4-1 was oxidized using a hydrogen peroxide solution to obtain Intermediate 4-2. Intermediate 4-2 was identified by LC-MS.

$C_{17}H_{13}BrNOP$: M+1 357.9

Synthesis of Compound 4

5.1 g of Compound 4 was obtained (yield: 52%) in substantially the same manner as in Synthesis of Compound 1, except that Intermediate 4-2 was used instead of Intermediate 1-2. Compound 4 was identified by LC-MS and 1H-NMR.

$C_{32}H_{27}N_2OP$: M+1 487.19

$^1$H NMR (500 MHz, CDCl$_3$) δ=9.14 (s, 1H), 8.77 (d, 1H), 8.28 (d, 1H), 7.75-7.70 (m, 2H), 7.52 (d, 1H), 7.21-7.11 (m, 6H), 6.93 (t, 2H), 1.67 (s, 6H).

Synthesis Example 3: Synthesis of Compound 5

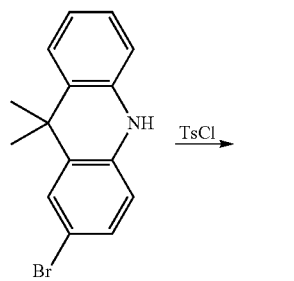

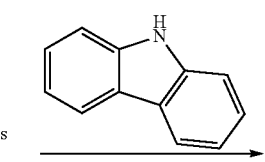

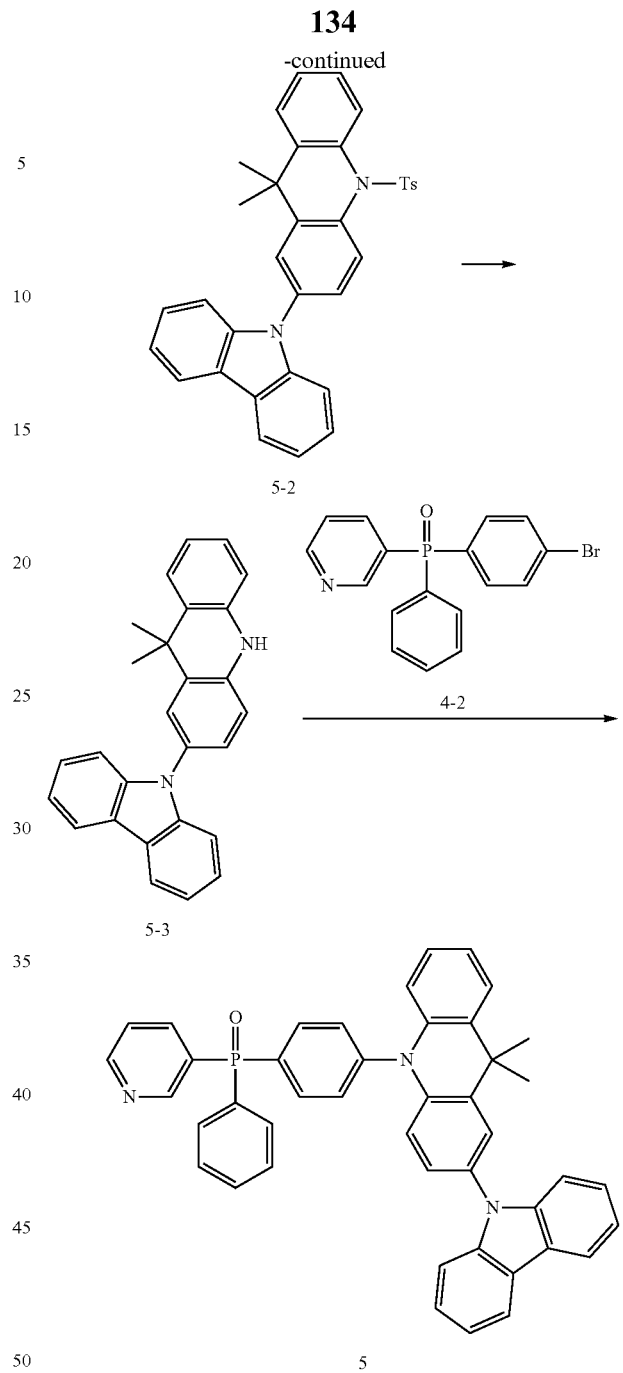

Synthesis of Intermediate 5-1

2-bromo-9,9-dimethyl-9,10-dihydroacridine (CAS No. 1443680-94-1) was reacted with tosyl chloride (TsCl) under basic conditions to obtain Intermediate 5-1. Intermediate 5-1 was identified by LC-MS.

$C_{22}H_{20}BrNO_2S$: M+1 442.1

Synthesis of Intermediate 5-2

Intermediate 5-1 and carbazole was reacted using a copper catalyst to obtain Intermediate 5-2. Intermediate 5-2 was identified by LC-MS.

$C_{34}H_{28}N_2O_2S$: M+1 529.3

Synthesis of Intermediate 5-3

Under an acidic condition, the protective groups of Compound 5-2 were removed therefrom to obtain Intermediate 5-3. Intermediate 5-3 was identified by LC-MS.

$C_{27}H_{22}N_2$: M+1 375.2

Synthesis of Compound 5

3.9 g of Intermediate 5-3, 3.7 g of Intermediate 4-2, 0.09 g of palladium (II) acetate, 0.22 g of triphenyl phosphine, and 1.00 g of NaOtBu were dissolved in 50 mL of toluene, and then the resulting solution was refluxed for 3 hours. The obtained reaction solution was cooled to ambient temperature, an organic layer was extracted using ethyl acetate, and then the organic layer was washed with water. The obtained organic layer was dried by using $MgSO_4$, a solvent was removed therefrom by evaporation, and the obtained residue was separated and purified through silica gel chromatography to thereby obtain 3.9 g of Compound 5 (yield: 58%). Compound 5 was identified by LC-MS and 1H-NMR.

$C_{44}H_{34}N_3OP$: M+1 652.3

$^1$H NMR (500 MHz, CDCl$_3$) δ=9.17 (s, 11H), 8.77 (d, 1H), 8.54 (d, 2H), 8.24 (d, 1H), 7.93 (d, 2H), 7.75-7.70 (m, 3H), 7.56-7.49 (m, 3H), 7.38-7.31 (m, 5H), 7.19-7.15 (m, 4H), 6.89 (t, 1H).

Synthesis Example 4: Synthesis of Compound 11

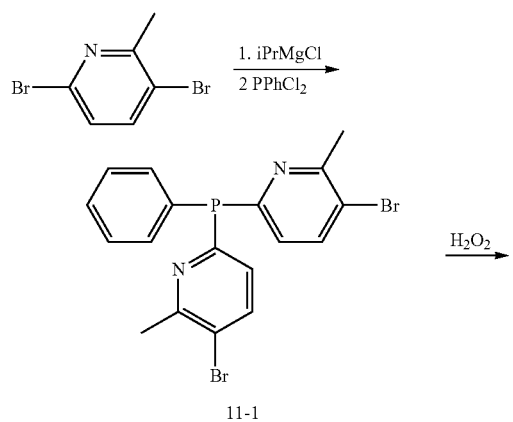

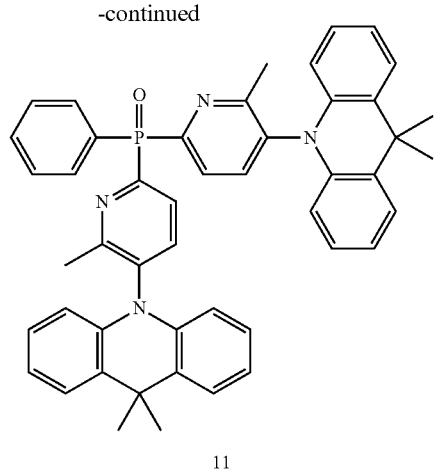

11

Synthesis of Intermediate 11-1

Intermediate 11-1 was obtained in substantially the same manner as in Synthesis of Intermediate 1-1, except that 3,6-dibromo-2-methyl pyridine was used instead of 2,5-dibromopyridine. Intermediate 11-1 was identified by LC-MS.

$C_{18}H_{15}Br_2N_2P$: M+1 448.9

Synthesis of Intermediate 11-2

Intermediate 11-1 was oxidized using a hydrogen peroxide solution to obtain Intermediate 11-2. Intermediate 11-2 was identified by LC-MS.

$C_{18}H_{15}Br_2N_2OP$: M+1 464.9

Synthesis of Compound 11

5.2 g of Compound 11 was obtained (yield: 63%) in substantially the same manner as in Synthesis of Compound 1, except that Intermediate 11-2 was used instead of Intermediate 1-2. Compound 11 was identified by LC-MS and $^1$H-NMR.

$C_{48}H_{43}N_4OP$: M+1 723.3

$^1$H NMR (500 MHz, CDCl$_3$) δ=7.78 (d, 4H), 7.52-7.49 (m, 3H), 7.27 (d, 2H), 7.21-7.11 (m, 12H), 6.92 (t, 4H), 2.51 (s, 3H), 1.69 (s, 12H).

Synthesis Example 5: Synthesis of Compound 16

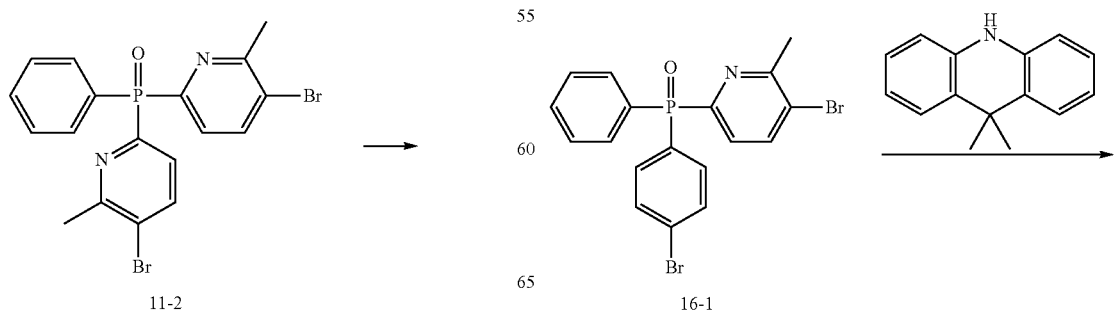

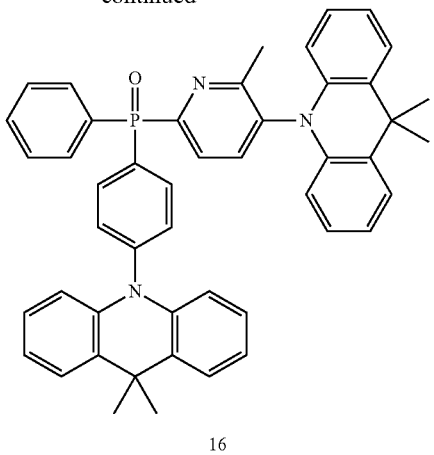

Synthesis of Intermediate 16-1

Intermediate 16-1 was obtained in substantially the same manner as in Synthesis of Intermediate 4-1, except that 3,6-dibromo-2-methyl pyridine was used instead of 2,5-dibromopyridine. Intermediate 16-1 was identified by LC-MS.

$C_{18}H_{15}BrNOP$: M+1 372.2

Synthesis of Compound 16

5.7 g of Compound 16 was obtained (yield: 71%) in substantially the same manner as in Synthesis of Compound 4, except that Intermediate 16-1 was used instead of Intermediate 4-1. Compound 16 was identified by LC-MS and $^1$H-NMR.

$C_{48}H_{42}N_3OP$: M+1 708.7

$^1$H NMR (500 MHz, CDCl$_3$) δ=7.78-7.72 (m, 5H), 7.52-7.49 (m, 3H), 7.37-7.14 (m, 15H), 6.94 (t, 4H), 2.51 (s, 3H), 1.67 (s, 12H).

Synthesis Example 6: Synthesis of Compound 20

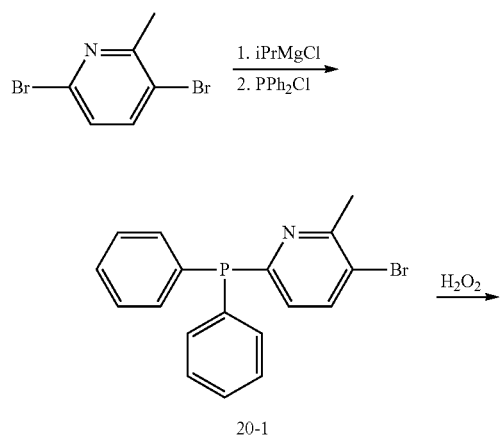

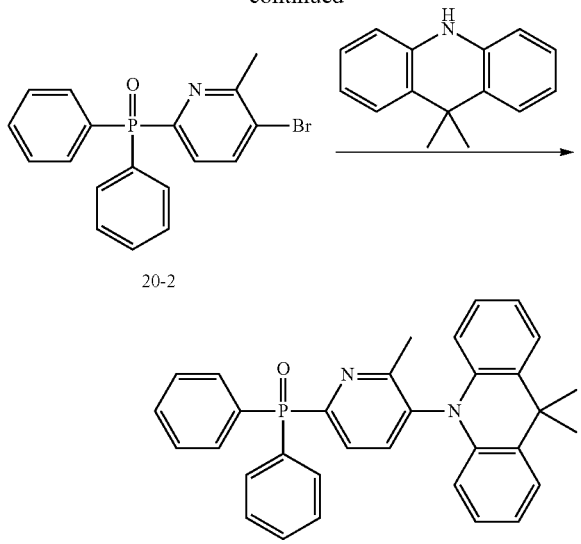

Synthesis of Intermediate 20-1

3,6-dibromo-2-methyl pyridine was dissolved in THF, isopropyl magnesium chloride (iPrMgCl) was added dropwise thereto, and the mixture was stirred to obtain a Grignard reagent. Diphenyl chlorophosphine (PPhCl$_2$) was added to the Grignard reagent, and then the mixture was stirred to obtain Intermediate 20-1. Intermediate 20-1 was identified by LC-MS.

$C_{18}H_{15}BrNP$: M+1 356.1

Synthesis of Intermediate 20-2

Intermediate 20-1 was oxidized using a hydrogen peroxide solution to obtain Intermediate 20-2. Intermediate 20-2 was identified by LC-MS.

$C_{18}H_{15}BrNOP$: M+1 372.3

Synthesis of Compound 20

2.2 g of Intermediate 20-2, 1.2 g of 9,9-dimethyl-9,10-dihydroacridine, 0.053 g of palladium (II) acetate, 0.12 g of triphenyl phosphine, and 0.85 g of NaOtBu were dissolved in 30 mL of toluene, and then the resulting solution was refluxed for 3 hours. The obtained reaction solution was cooled to ambient temperature, an organic layer was extracted using ethyl acetate, and then the organic layer was washed with water. The obtained organic layer was dried by using MgSO$_4$, a solvent was removed therefrom by evaporation, and the obtained residue was separated and purified through silica gel chromatography to thereby obtain 2.3 g of Compound 20 (yield: 77%). Compound 20 was identified by LC-MS and $^1$H-NMR.

$C_{33}H_{29}N_2OP$: M+1 501.5

$^1$H NMR (500 MHz, CDCl$_3$) δ=7.80-7.71 (m, 6H), 7.51-7.49 (m, 6H), 7.28 (d, 2H), 7.21-7.13 (m, 6H), 6.94 (t, 2H), 2.54 (s, 3H), 1.62 (s, 6H).

Synthesis Example 7: Synthesis of Compound 27

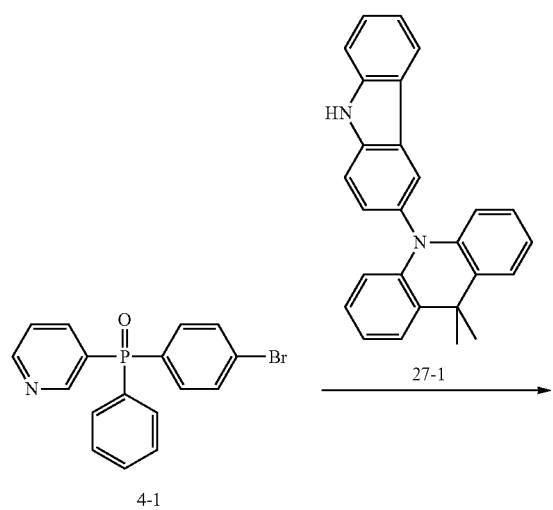

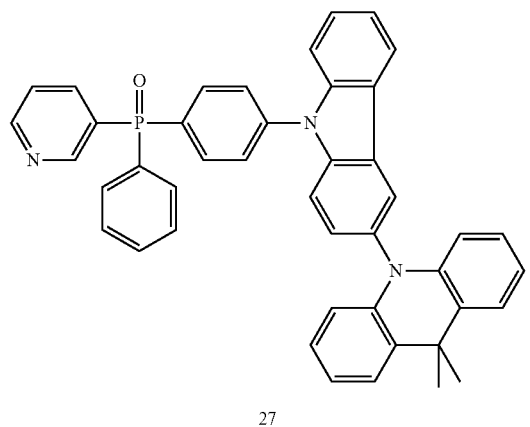

Synthesis of Compound 27

5.2 g of Intermediate 4-1, 5.5 g of Intermediate 27-1 (CAS No. 1821228-18-5), 0.13 g of palladium (II) acetate, 0.31 g of triphenyl phosphine, and 1.4 g of NaOtBu were dissolved in 80 mL of toluene, and then the resulting solution was refluxed for 3 hours. The obtained reaction solution was cooled to ambient temperature, an organic layer was extracted using ethyl acetate, and then the organic layer was washed with water. The obtained organic layer was dried by using $MgSO_4$, a solvent was removed therefrom by evaporation, and the obtained residue was separated and purified through silica gel chromatography to thereby obtain 4.7 g of Compound 27 (yield: 49%). Compound 27 was identified by LC-MS and $^1$H-NMR.

$C_{44}H_{34}N_3OP$: M+1 652.3

$^1$H NMR (500 MHz, $CDCl_3$) δ=9.13 (s, 1H), 8.75 (d, 1H), 8.54 (d, 1H), 8.29 (d, 1H), 7.98-7.90 (m, 9H), 7.58-7.50 (m, 2H), 7.38-7.31 (m, 3H), 7.21-7.11 (m, 7H), 6.94 (t, 2H), 1.71 (s, 6H).

Synthesis Example 8: Synthesis of Compound 28

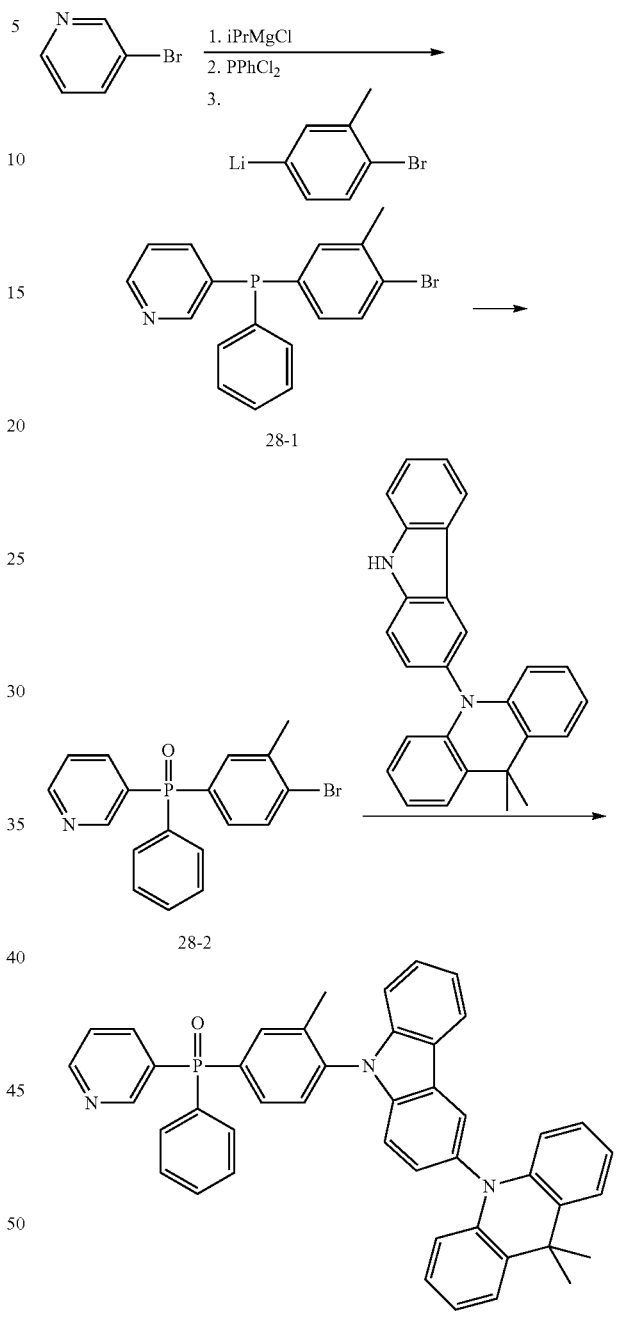

Synthesis of Intermediate 28-1

3-bromopyridine was dissolved in THF, isopropyl magnesium chloride (iPrMgCl) was added dropwise thereto, and the mixture was stirred to obtain a Grignard reagent. The Grignard reagent was allowed to react with phenyl dichlorophosphine, a (4-bromo-3-methylphenyl) lithium solution (CAS No. 17989-26-3) was added dropwise thereto, and then the mixture was stirred to obtain Intermediate 28-1. Intermediate 28-1 was identified by LC-MS.

$C_{18}H_{15}BrNP$ M+1: 356.1

Synthesis of Intermediate 28-2

Intermediate 28-1 was oxidized using a hydrogen peroxide solution to obtain Intermediate 28-2. Intermediate 28-2 was identified by LC-MS.

$C_{18}H_{15}BrNOP$: M+1 372.1

Synthesis of Compound 28

3.2 g of Compound 28 was obtained (yield: 43%) in substantially the same manner as in Synthesis of Compound 4, except that Intermediate 28-2 was used instead of Intermediate 4-2. Compound 28 was identified by LC-MS and $^1$H-NMR.

$C_{45}H_{36}N_3OP$: M+1 666.4

$^1$H NMR (500 MHz, CDCl$_3$) δ=8.74 (d, 1H), 8.54 (d, 1H), 8.26 (d, 1H), 7.94 (d, 1H), 7.89-7.72 (m, 6H), 7.55-7.49 (m, 5H), 7.38-7.12 (m, 10H), 6.92 (t, 2H), 1.89 (s, 3H), 1.69 (s, 6H).

Synthesis Example 10: Synthesis of Compound 55 washed with water. The obtained organic layer was dried by using MgSO$_4$, a solvent was removed therefrom by evaporation, and the obtained residue was separated and purified through silica gel chromatography to thereby obtain 3.2 g of Intermediate 55-2 (yield: 42%). Intermediate 55-2 was identified by LC-MS.

$C_{20}H_{17}BrN_2$: M+1 365.1

Synthesis of Compound 55

3.0 g of Intermediate 55-2, 3.7 g of Intermediate 55-1 (CAS No. 328917-29-9), 0.38 g of Pd(PPh$_3$)$_4$, 2.8 g of potassium carbonate, 40 mL of toluene, 10 mL of ethanol, and 10 mL of water were added to a round-bottom flask, and then the mixture was refluxed overnight. The obtained reaction solution was cooled to ambient temperature, an organic layer was extracted using ethyl acetate, and then the organic layer was washed with water. The obtained organic layer was dried by using MgSO$_4$, a solvent was removed therefrom by evaporation, and the obtained residue was

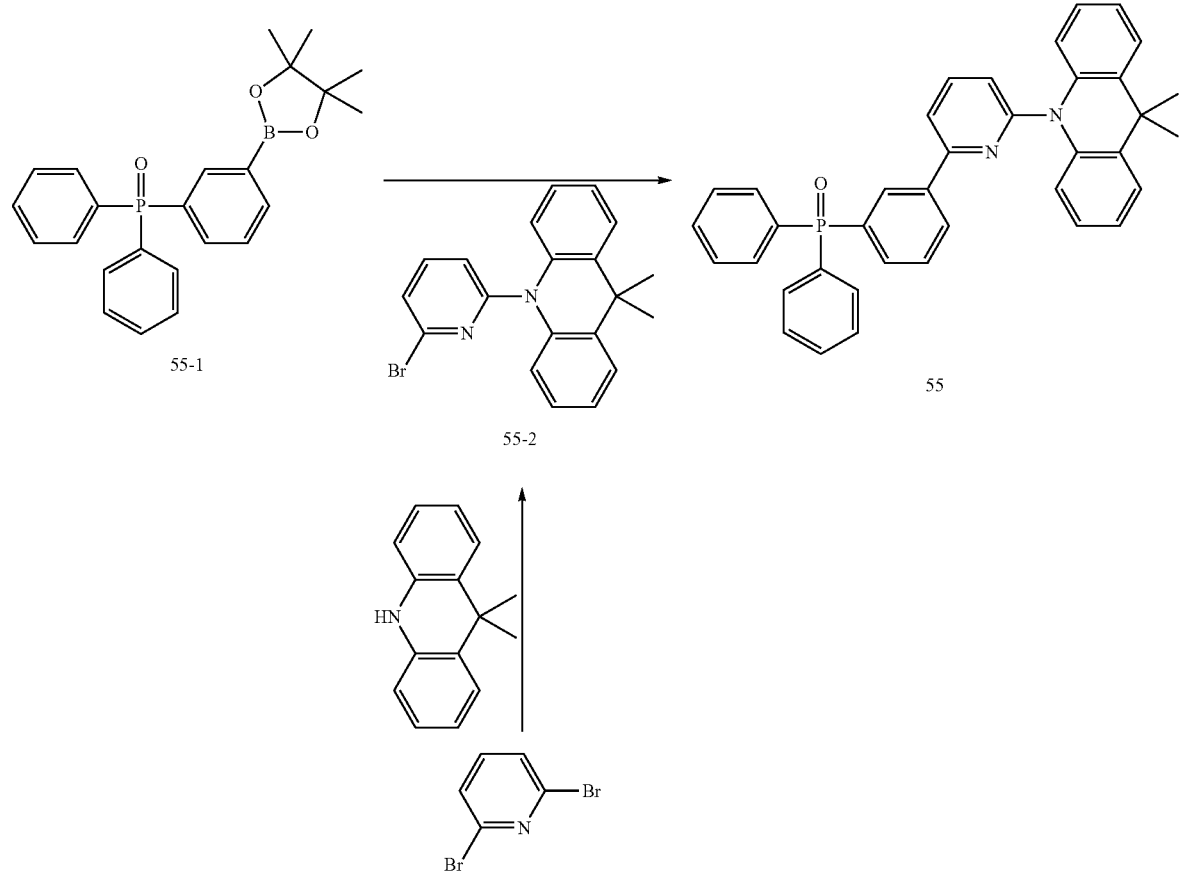

Synthesis of Intermediate 55-2

10 g of 2,6-dibromopyridine, 4.4 g of 9,9-dimethyl-9,10-dihydroacridine, 0.14 g of palladium (II) acetate, 0.33 g of triphenyl phosphine, and 3.0 g of NaOtBu were dissolved in 200 mL of toluene, and then the resulting solution was refluxed for 3 hours. The obtained reaction solution was cooled to ambient temperature, an organic layer was extracted using ethyl acetate, and then the organic layer was separated and purified through silica gel chromatography to thereby obtain 2.9 g of Compound 55 (yield: 62%). Compound 55 was identified by LC-MS and $^1$H-NMR.

$C_{38}H_{31}N_2OP$: M+1 563.2

$^1$H NMR (500 MHz, CDCl$_3$) δ=8.53 (s, 1H), 8.49 (d, 1H), 7.88 (d, 1H), 7.79-7.72 (m, 5H), 7.52-7.49 (m, 6H), 7.21-7.02 (m, 7H), 6.92 (t, 2H), 6.36 (d, 1H), 6.21 (d, 1H), 1.67 (s, 6H).

Synthesis Example 11: Synthesis of Compound 61

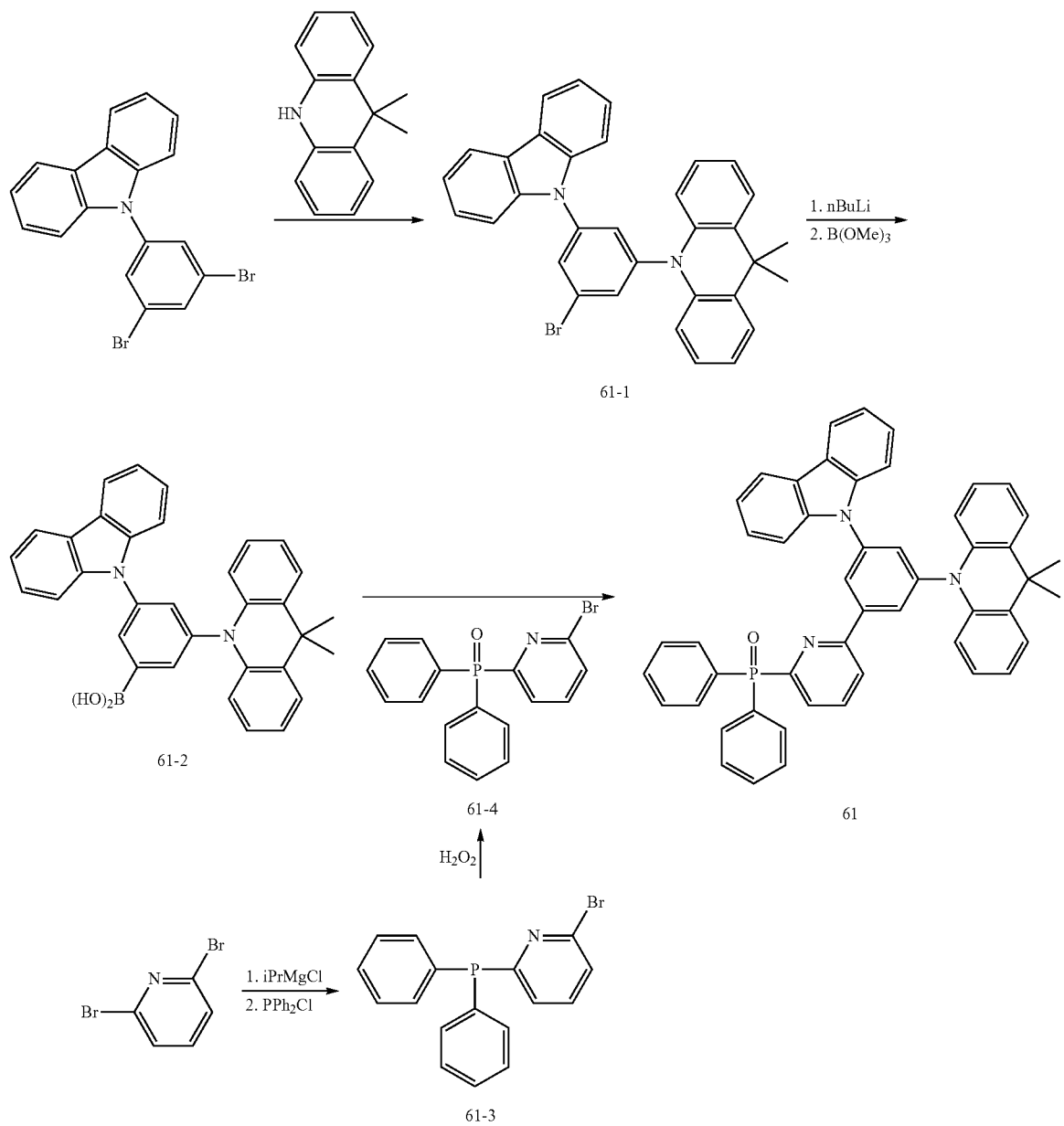

Synthesis of Intermediate 61-1

9-(3,5-dibromophenyl)-9H-carbazole (CAS No. 750573-26-3) was reacted with 9,9-dimethyl-9,10-dihydroacridine using a palladium catalyst to obtain Intermediate 61-1. Intermediate 61-1 was identified by LC-MS.

$C_{33}H_{25}BrN_2$ M+1: 529.1

Synthesis of Intermediate 61-2

Intermediate 61-1 was reacted with n-BuLi, and B(OMe)$_3$ was added dropwise thereto. Then, a purification process was performed thereon to obtain Intermediate 61-2. Intermediate 61-2 was identified by LC-MS.

$C_{33}H_{27}BN_2O_2$: M+1 495.3

Synthesis of Intermediate 61-3

2,6-dibromopyridine was dissolved in THF, isopropyl magnesium chloride (iPrMgCl) was added dropwise thereto, and the mixture was stirred to obtain a Grignard reagent. The Grignard reagent was reacted with chlorodiphenylphosphine to obtain Intermediate 61-3. Intermediate 61-3 was identified by LC-MS.

$C_{17}H_{13}BrNP$ M+1: 342.4

Synthesis of Intermediate 61-4

Intermediate 61-3 was oxidized using a hydrogen peroxide solution to obtain Intermediate 61-4. Intermediate 61-4 was identified by LC-MS.

$C_{17}H_{13}BNOP$: M+1 357.9

Synthesis of Compound 61

3.7 g of Intermediate 61-4, 3.7 g of Intermediate 61-2 (CAS No. 328917-29-9), 0.17 g of Pd(PPh$_3$)$_4$, 3.6 g of potassium carbonate, 45 mL of toluene, 15 mL of ethanol, and 15 mL of water were added to a round-bottom flask, and then the mixture was refluxed overnight. The obtained reaction solution was cooled to ambient temperature, an organic layer was extracted using ethyl acetate, and then the organic layer was washed with water. The obtained organic layer was dried by using MgSO$_4$, a solvent was removed therefrom by evaporation, and the obtained residue was separated and purified through silica gel chromatography to thereby obtain 4.1 g of Compound 61 (yield: 55%). Compound 61 was identified by LC-MS and $^1$H-NMR.

$C_{50}H_{38}N_3OP$: M+1 728.31

$^1$H NMR (500 MHz, CDCl$_3$) δ=8.57 (d, 2H), 8.22 (s, 1H), 7.92 (d, 2H), 7.78-7.71 (m, 4H), 7.61 (s, 1H), 7.58 (t, 11H), 7.53-7.48 (m, 7H), 7.41-7.24 (m, 4H), 7.21-7.11 (m, 8H), 6.92 (t, 2H), 1.68 (s, 6H).

Synthesis Example 12: Synthesis of Compound 71

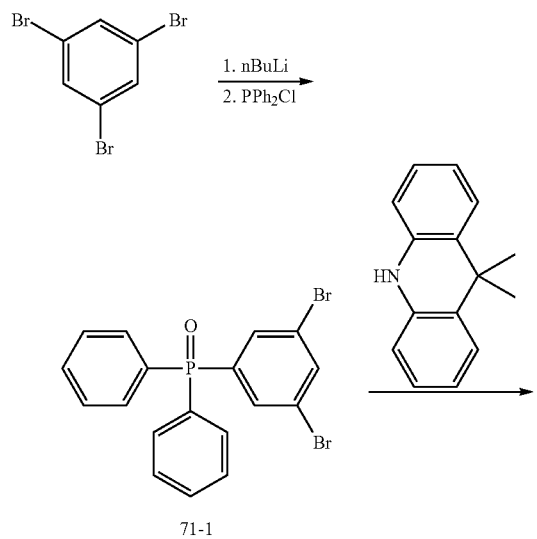

71-1

Synthesis of Intermediate 71-1

1,3,5-tribromobenzene was reacted with n-BuLi, diphenylchlorophosphine was added dropwise thereto, and then the mixture was stirred to obtain Intermediate 71-1. Intermediate 71-1 was identified by LC-MS.

$C_{18}H_{13}Br_2OP$: M+1 433.91

Synthesis of Compound 71

1.9 g of Intermediate 71-1, 1.8 g of 9,9-dimethyl-9,10-dihydroacridine (CAS No. 6267-02-3), 0.04 g of palladium (II) acetate, 0.09 g of triphenyl phosphine, and 0.63 g of NaOtBu were dissolved in 30 mL of toluene, and then the resulting solution was refluxed for 3 hours. The obtained reaction solution was cooled to ambient temperature, an organic layer was extracted using ethyl acetate, and then the organic layer was washed with water. The obtained organic layer was dried by using MgSO$_4$, a solvent was removed therefrom by evaporation, and the obtained residue was separated and purified through silica gel chromatography to thereby obtain 2.5 g of Compound 71 (yield: 82%). Compound 71 was identified by LC-MS and $^1$H-NMR.

$C_{48}H_{41}N_2OP$: M+1 693.41

$^1$H NMR (500 MHz, CDCl$_3$) δ=7.79-7.72 (m, 4H), 7.53-7.42 (m, 6H), 7.23 (s, 2H), 7.19-7.08 (m, 15H), 6.92 (t, 4H), 1.65 (s, 12H).

Synthesis Example 13: Synthesis of Compound 72

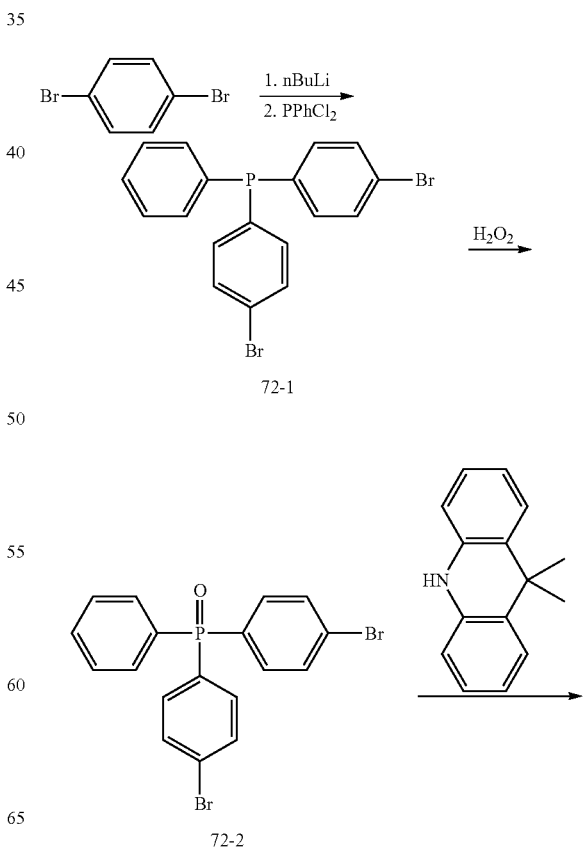

72-1

72-2

147
-continued

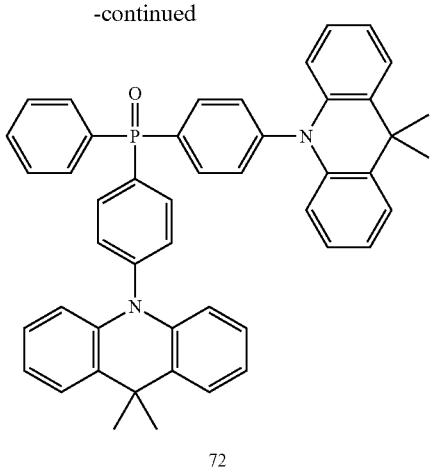

72

Synthesis of Intermediate 72-1

1,4-tribromobenzene was reacted with n-BuLi, dichlorophenylphosphine was added dropwise thereto, and then the mixture was stirred to obtain Intermediate 71-1. Intermediate 71-1 was identified by LC-MS.

$C_{18}H_{13}Br_2P$: M+1 418.8

Synthesis of Intermediate 72-2

Intermediate 72-1 was oxidized using a hydrogen peroxide solution to obtain Intermediate 72-2.

$C_{18}H_{13}Br_2OP$: M+1 434.7

Synthesis of Compound 72

2.44 g of Compound 72 was obtained (yield: 81%) in substantially the same manner as in Synthesis of Compound 71, except that Intermediate 72-2 was used instead of Intermediate 71-1.

$C_{48}H_{41}N_2OP$: M+1 693.4

$^1$H NMR (500 MHz, CDCl$_3$) δ=7.81-7.70 (m, 6H), 7.53-7.48 (m, 3H), 7.41-7.34 (m, 4H), 7.21-7.11 (m, 12H), 6.95 (t, 4H), 1.71 (s, 12H).

Example 1

A Corning 15 ohms per square centimeter (Ω/cm²) (1,200 Å thickness) ITO glass substrate was cut to a size of 50 millimeters (mm)×50 mm×0.7 mm, sonicated in isopropyl alcohol and pure water for 5 minutes each, and cleaned by exposure to ultraviolet rays and ozone, so that the resulting ITO glass substrate could be used as a substrate and an anode. Then, the glass substrate was mounted on a vacuum deposition apparatus.

NPD was vacuum-deposited on the ITO anode formed on the substrate to form a hole injection layer having a thickness of 300 Å, and mCP was vacuum-deposited as a hole transporting compound on the hole injection layer to form a hole transport layer having a thickness of 200 Å.

Compound 1 and FIrpic were co-deposited in a weight ratio of 92:8 on the hole transport layer to form an emission layer having a thickness of 250 Å.

Next, TAZ was deposited on the emission layer to form an electron transport layer having a thickness of 200 Å, LiF was deposited on the electron transport layer to form an electron injection layer having a thickness of 10 Å, and aluminum was vacuum-deposited on the electron injection layer to form a LiF/Al cathode having a thickness of 100 Å, thereby completing the manufacture of an organic light-emitting device.

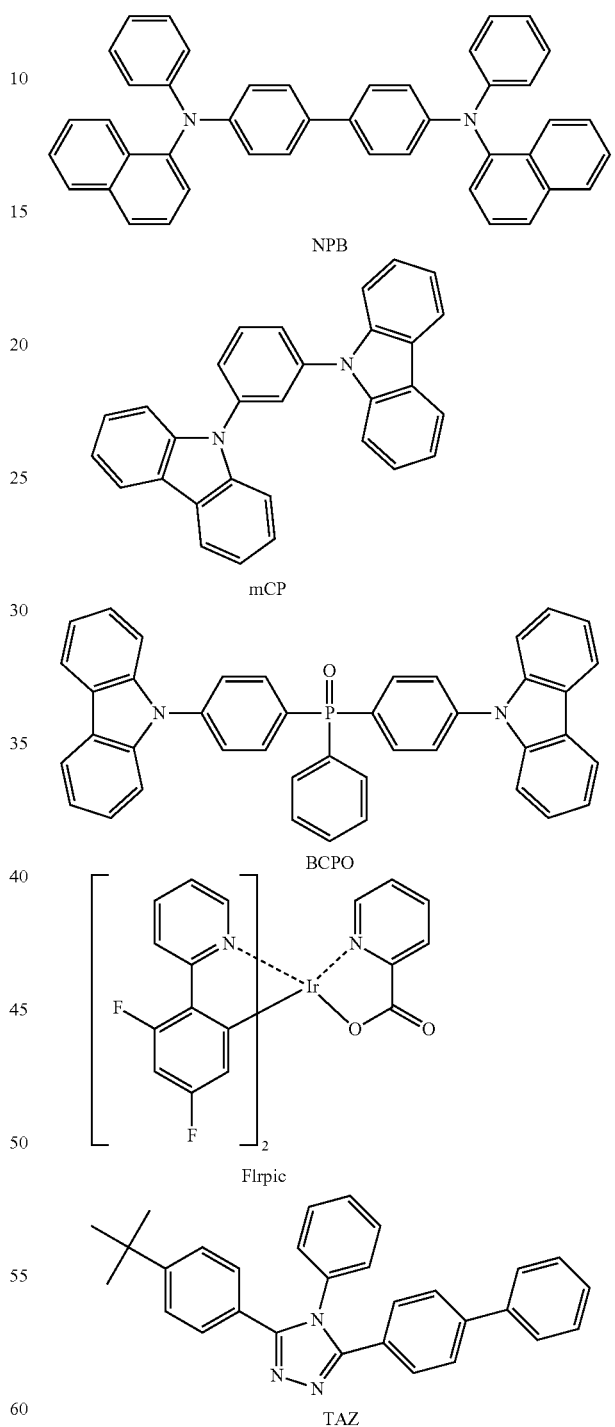

Examples 2 to 7 and Comparative Examples 1 to 3

Organic light-emitting devices were manufactured in substantially the same manner as in Example 1, except that the compounds shown in Table 1 were used instead of Compound 1 in forming each emission layer.

Evaluation Example 1

The driving voltage, current density, efficiency, and emission color of the organic light-emitting devices manufactured in Examples 1 to 7 and Comparative Examples 1 to 3 were measured. The results thereof are shown in Table 1.

TABLE 1

|  | Emission layer | Driving voltage (V) | Current density (mA/cm$^2$) | Maximum quantum efficiency (%) | Emission color |
|---|---|---|---|---|---|
| Example 1 | 1 | 3.0 | 1 | 24.4 | blue |
| Example 2 | 5 | 2.7 | 1 | 28.5 | blue |
| Example 3 | 27 | 3.1 | 1 | 20.2 | blue |
| Example 4 | 55 | 2.7 | 1 | 27.3 | blue |
| Example 5 | 61 | 2.9 | 1 | 28.8 | blue |
| Example 6 | 71 | 3.2 | 1 | 23.9 | blue |
| Example 7 | 72 | 3.1 | 1 | 22.7 | blue |
| Comparative Example 1 | BCPO | 3.5 | 1 | 19.2 | blue |
| Comparative Example 2 | A | 3.4 | 1 | 20.1 | blue |
| Comparative Example 3 | B | 3.1 | 1 | 19.9 | blue |

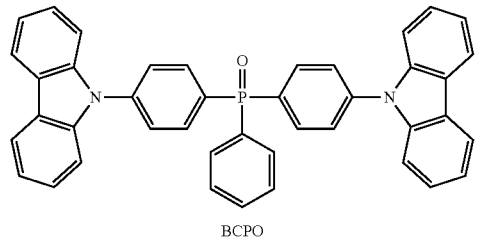

BCPO

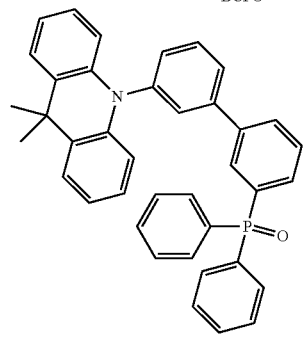

A

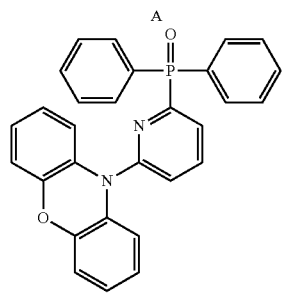

B

Referring to Table 1, the organic light-emitting devices of Examples 1 to 7 were found to have low driving voltage and excellent efficiency, as compared with the organic light-emitting devices of Comparative Examples 1 to 3.

Example 8

A Corning 15 Ω/cm$^2$ (1,200 Å thickness) ITO glass substrate was cut to a size of 50 mm×50 mm×0.7 mm, sonicated in isopropyl alcohol and pure water for 5 minutes each, and cleaned by exposure to ultraviolet rays and ozone, so that the resulting ITO glass substrate could be used as a substrate and an anode. Then, the glass substrate was mounted on a vacuum deposition apparatus.

NPD was vacuum-deposited on the ITO anode formed on the substrate to form a hole injection layer having a thickness of 300 Å, and TCTA was vacuum-deposited as a hole transporting compound on the hole injection layer to form a hole transport layer having a thickness of 200 Å.

A hole transport layer compound CzSi was vacuum-deposited on the hole transport layer to a thickness of 100 Å, and then DPEPO and Compound 4 were co-deposited in a weight ratio of 90:10 to form an emission layer having a thickness of 200 Å.

Next, DPEPO was deposited on the emission layer to form an electron transport layer having a thickness of 200 Å, TPBI was deposited on the electron transport layer to a thickness of 300 Å, LiF was deposited thereon to a thickness of 10 Å to form an electron injection layer, and aluminum was vacuum-deposited on the electron injection layer to form a LiF/Al cathode having a thickness of 3,000 Å, thereby completing the manufacture of an organic light-emitting device.

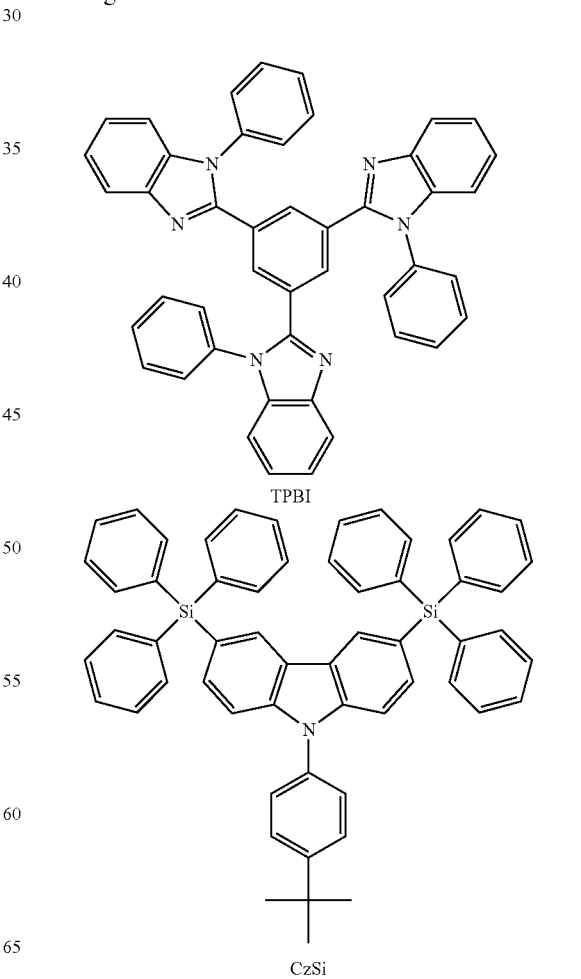

-continued

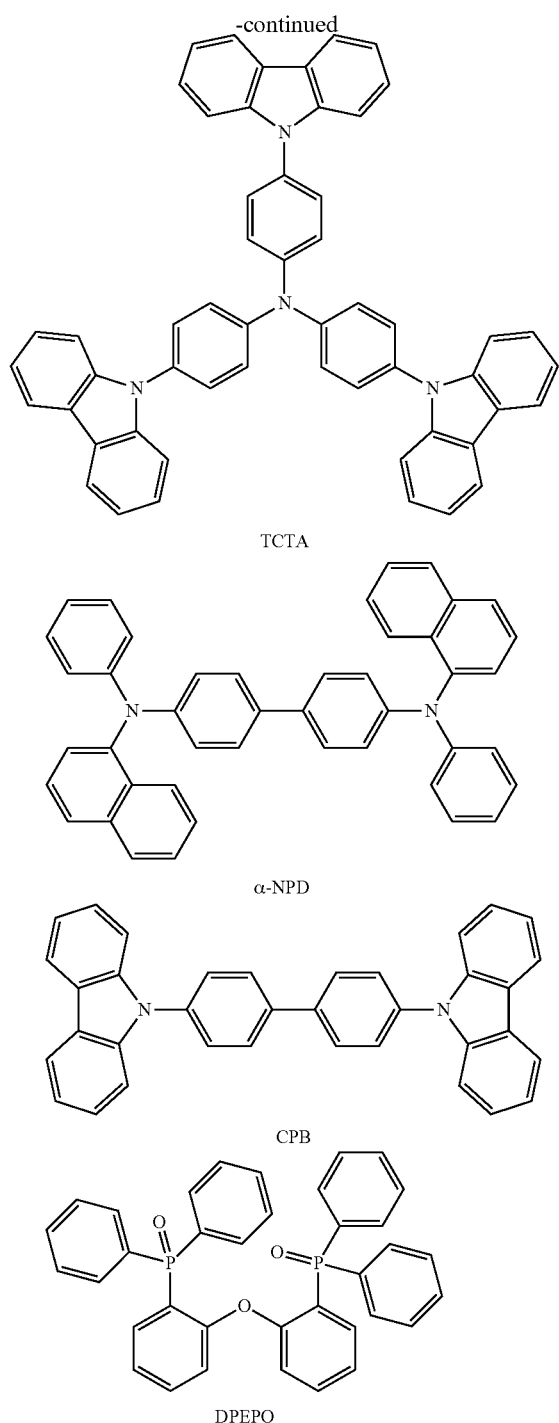

TCTA

α-NPD

CPB

DPEPO

Examples 9 and 14 and Comparative Examples 4 to 6

Organic light-emitting devices were manufactured in substantially the same manner as in Example 8, except that the compounds shown in Table 2 were used instead of Compound 4 in forming each emission layer.

Evaluation Example 2

The driving voltage, current density, efficiency, and emission color of the organic light-emitting devices manufactured in Examples 8 to 14 and Comparative Examples 4 to 6 were measured. The results thereof are shown in Table 2.

TABLE 2

| | Emission layer | Driving voltage (V) | Current density (mA/cm$^2$) | Efficiency (cd/A) | Emission color |
|---|---|---|---|---|---|
| Example 8 | 4 | 5.9 | 1 | 7.7 | blue |
| Example 9 | 5 | 7.1 | 1 | 8.6 | blue |
| Example 10 | 11 | 6.7 | 1 | 8.4 | blue |
| Example 11 | 16 | 6.6 | 1 | 7.9 | blue |
| Example 12 | 20 | 6.9 | 1 | 7.6 | blue |
| Example 13 | 28 | 6.0 | 1 | 8.2 | blue |
| Example 14 | 71 | 6.8 | 1 | 7.9 | blue |
| Comparative Example 4 | DPS | 7.4 | 1 | 7.2 | blue |
| Comparative Example 5 | A | 7.5 | 1 | 5.1 | blue |
| Comparative Example 6 | B | 7.2 | 1 | 5.9 | blue |

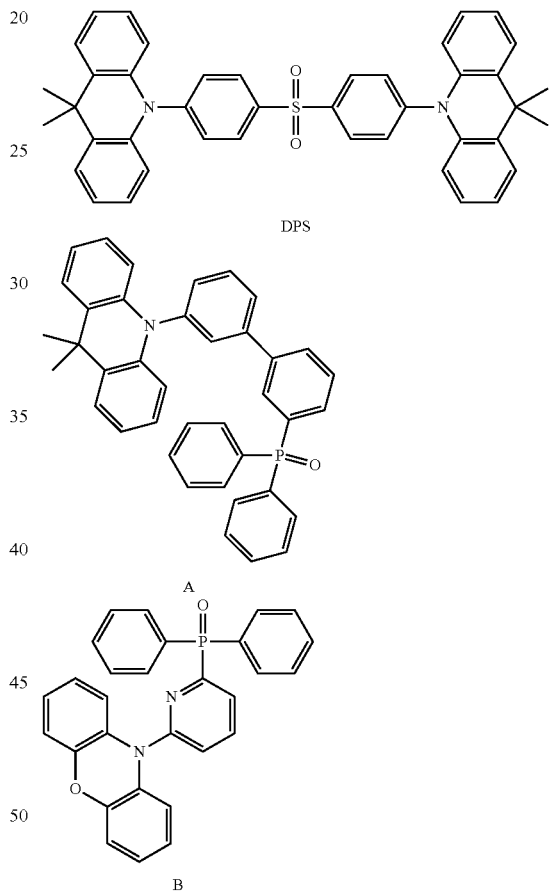

DPS

A

B

Referring to Table 2, the organic light-emitting devices of Examples 8 to 14 were found to have low driving voltage and excellent efficiency, as compared with the organic light-emitting devices of Comparative Examples 4 to 6.

As apparent from the foregoing description, an organic light-emitting device including the heterocyclic compound may have low driving voltage, high luminance, high efficiency, and a long lifespan.

The embodiments may provide an organic light-emitting device with low driving voltage, high luminance, high efficiency, and long lifespan characteristics.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound represented by Formula 1:

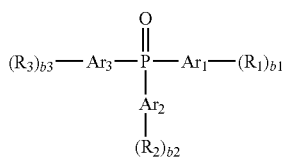

Formula 1 wherein:
$Ar_1$, $Ar_2$ and $Ar_3$ are each independently selected from optionally substituted $C_5$-$C_{60}$ carbocyclyl and optionally substituted $C_2$-$C_{60}$ heterocyclyl;
$R_1$, $R_2$ and $R_3$ are each independently represented by the following Formula 2;
b1, b2 and b3 are each independently 0, 1, 2 or 3;
with the proviso that (i) the sum of b1, b2 and b3 is greater than or equal to 1; or (ii) when $Ar_1$, $Ar_2$ and $Ar_3$ are each optionally substituted phenyl, the sum of b1, b2 and b3 is greater than or equal to 2;
Formula 2 is represented by:

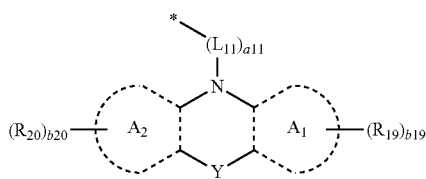

Formula 2 wherein:
$A_1$ and $A_2$ are each independently selected from phenyl, naphthalenyl, phenanthrenyl, fluoranthenyl, triphenylenyl, pyrenyl, chrysenyl, pyridinyl and pyrimidinyl;
$L_{11}$ is selected from optionally substituted $C_3$-$C_{10}$ cycloalkylenyl, optionally substituted $C_1$-$C_{10}$ heterocycloalkylenyl, optionally substituted $C_3$-$C_{10}$ cycloalkenylenyl, optionally substituted $C_1$-$C_{10}$ heterocycloalkenylenyl, optionally substituted $C_6$-$C_{60}$ arylenyl, optionally substituted $C_1$-$C_{60}$ heteroarylenyl, optionally substituted divalent non-aromatic condensed polycyclyl and optionally substituted divalent non-aromatic condensed heteropolycyclyl;
$Q_1$, $Q_2$, $Q_{11}$, $Q_{12}$, $Q_{13}$, $Q_{21}$, $Q_{22}$, $Q_{23}$, $Q_{31}$, $Q_{32}$ and $Q_{33}$ are each independently selected from hydrogen, deuterium, fluoro, chloro, bromo, iodo, hydroxy, cyano, nitro, amidino, hydrazino, hydrazono, $C_1$-$C_{60}$ alkyl, $C_2$-$C_{60}$ alkenyl, $C_2$-$C_{60}$ alkynyl, $C_1$-$C_{60}$ alkoxy, $C_3$-$C_{10}$ cycloalkyl, $C_1$-$C_{10}$ heterocycloalkyl, $C_3$-$C_{10}$ cycloalkenyl, $C_1$-$C_{10}$ heterocycloalkenyl, $C_6$-$C_{60}$ aryl, $C_1$-$C_{60}$ heteroaryl, monovalent non-aromatic condensed polycyclyl, monovalent non-aromatic condensed heteropolycyclyl, biphenyl and terphenyl;
$R_{17}$, $R_{18}$, $R_{19}$ and $R_{20}$ are each independently selected from hydrogen, deuterium, fluoro, chloro, bromo, iodo, hydroxy, cyano, nitro, amidino, hydrazino, hydrazono, optionally substituted $C_1$-$C_{60}$ alkyl, optionally substituted $C_2$-$C_{60}$ alkenyl, optionally substituted $C_2$-$C_{60}$ alkynyl, optionally substituted $C_1$-$C_{60}$ alkoxy, optionally substituted $C_3$-$C_{10}$ cycloalkyl, optionally substituted $C_1$-$C_{10}$ heterocycloalkyl, optionally substituted $C_3$-$C_{10}$ cycloalkenyl, optionally substituted $C_1$-$C_{10}$ heterocycloalkenyl, optionally substituted $C_6$-$C_{60}$ aryl, optionally substituted $C_6$-$C_{60}$ aryloxy, optionally substituted $C_6$-$C_{60}$ arylthio, optionally substituted $C_1$-$C_{60}$ heteroaryl, optionally substituted monovalent non-aromatic condensed polycyclyl, optionally substituted monovalent non-aromatic condensed heteropolycyclyl, —S(=O)($Q_1$) and —P(=O)($Q_1$)($Q_2$);
Y is selected from C($R_{17}$)($R_{18}$), (S), Si($R_{17}$)($R_{18}$), S(=O), S(=O)$_2$ and P(=O)($R_{17}$);
a11 is 1;
b19 and b20 are each independently 0, 1, 2, 3, 4, 5, 6, 7 or 8; and
* is a binding site to an adjacent atom;
wherein the optional substituents in Formula 1 and Formula 2 are selected from:
(i) deuterium, fluoro, chloro, bromo, iodo, hydroxy, cyano, nitro, amidino, hydrazino, hydrazono, $C_1$-$C_{60}$ alkyl, $C_2$-$C_{60}$ alkenyl, $C_2$-$C_{60}$ alkynyl, $C_1$-$C_{60}$ alkoxy, $C_3$-$C_{10}$ cycloalkyl, $C_1$-$C_{10}$ heterocycloalkyl, $C_3$-$C_{10}$ cycloalkenyl, $C_1$-$C_{10}$ heterocycloalkenyl, $C_6$-$C_{60}$ aryl, $C_6$-$C_{60}$ aryloxy, $C_6$-$C_{60}$ arylthio, $C_1$-$C_{60}$ heteroaryl, monovalent non-aromatic condensed polycyclyl, monovalent non-aromatic condensed heteropolycyclyl, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$) and —P(=O)($Q_{31}$)($Q_{32}$);
(ii) $C_1$-$C_{60}$ alkyl, $C_2$-$C_{60}$ alkenyl, $C_2$-$C_{60}$ alkynyl and $C_1$-$C_{60}$ alkoxy, each optionally substituted with at least one substituent selected from deuterium, fluoro, chloro, bromo, iodo, hydroxy, cyano, nitro, amidino, hydrazino, hydrazono, $C_3$-$C_{10}$ cycloalkyl, $C_1$-$C_{10}$ heterocycloalkyl, $C_3$-$C_{10}$ cycloalkenyl, $C_1$-$C_{10}$ heterocycloalkenyl, $C_6$-$C_{60}$ aryl, $C_6$-$C_{60}$ aryloxy, $C_6$-$C_{60}$ arylthio, $C_1$-$C_{60}$ heteroaryl, monovalent non-aromatic condensed polycyclyl, monovalent non-aromatic condensed heteropolycyclyl, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$) and —P(=O)($Q_{11}$)($Q_{12}$); and
(iii) $C_3$-$C_{10}$ cycloalkyl, $C_1$-$C_{10}$ heterocycloalkyl, $C_3$-$C_{10}$ cycloalkenyl, $C_1$-$C_{10}$ heterocycloalkenyl, $C_6$-$C_{60}$ aryl, $C_6$-$C_{60}$ aryloxy, $C_6$-$C_{60}$ arylthio, $C_1$-$C_{60}$ heteroaryl, monovalent non-aromatic condensed polycyclyl and monovalent non-aromatic condensed heteropolycyclyl, each optionally substituted with at least one substituent selected from deuterium, fluoro, chloro, bromo, iodo, hydroxy, cyano, nitro, amidino, hydrazino, hydrazono, $C_1$-$C_{60}$ alkyl, $C_2$-$C_{60}$ alkenyl, $C_2$-$C_{60}$ alkynyl, $C_1$-$C_{60}$ alkoxy, $C_3$-$C_{10}$ cycloalkyl, $C_1$-$C_{10}$ heterocycloalkyl, $C_3$-$C_{10}$ cycloalkenyl, $C_1$-$C_{10}$ heterocycloalkenyl, $C_6$-$C_{60}$ aryl, $C_6$-$C_{60}$ aryloxy, $C_6$-$C_{60}$ arylthio, $C_1$-$C_{60}$ heteroaryl, monovalent non-aromatic condensed polycyclyl, monovalent non-aromatic condensed heteropolycyclyl, —Si(Q$_{21}$)(Q$_{22}$)(Q$_{23}$), —N(Q$_{21}$)(Q$_{22}$), —B(Q$_{21}$)(Q$_{22}$), —C(═O)(Q$_{21}$), —S(═O)$_2$(Q$_{21}$) and —P(═O)(Q$_{21}$)(Q$_{22}$).

2. The compound of claim 1, wherein at least one of Ar$_1$, Ar$_2$ and Ar$_3$ is an optionally substituted π-electron-depleted nitrogen-containing C$_2$-C$_{60}$ heterocyclyl.

3. The compound of claim 1, wherein:
Ar$_1$, Ar$_2$ and Ar$_3$ are each independently selected from phenyl, naphthalenyl, pyridinyl, pyrazinyl, pyrimidinyl, pyridazinyl, triazinyl, quinolinyl, isoquinolinyl, acridinyl, phenanthridinyl, phthalazinyl, naphthyridinyl, quinoxalinyl or quinazolinyl, each optionally substituted with at least one substituent selected from deuterium, fluoro, chloro, bromo, iodo, hydroxy, cyano, nitro, amidino, hydrazino, hydrazono, C$_1$-C$_{20}$ alkyl, C$_1$-C$_{20}$ alkoxy, cyclopentyl, cyclohexyl, cycloheptyl, cyclopentenyl, cyclohexenyl, phenyl, phenyl substituted with C$_1$-C$_{10}$ alkyl, phenyl substituted with fluoro, biphenyl, terphenyl, pentalenyl, indenyl, naphthyl, azulenyl, heptalenyl, indacenyl, acenaphthyl, fluorenyl, spiro-bifluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, thiophenyl, furanyl, carbazolyl, indolyl, isoindolyl, benzofuranyl, benzothiophenyl, dibenzofuranyl, dibenzothiophenyl, benzocarbazolyl, dibenzocarbazolyl, dibenzosilolyl, pyridinyl, —Si(Q$_{31}$)(Q$_{32}$)(Q$_{33}$) and —N(Q$_{31}$)(Q$_{32}$); and
Q$_{31}$, Q$_{32}$, and Q$_{33}$ are each independently selected from C$_1$-C$_{10}$ alkyl, C$_1$-C$_{10}$ alkoxy, phenyl, biphenyl, terphenyl and naphthyl.

4. The compound of claim 1, wherein A$_1$ and A$_2$ are each independently phenyl.

5. The compound of claim 1, wherein L$_{11}$ is selected from Formula 3-1, Formula 3-2, Formula 3-3, Formula 3-4, Formula 3-5, Formula 3-6, Formula 3-7, Formula 3-8, Formula 3-9, Formula 3-10, Formula 3-11, Formula 3-12, Formula 3-13, Formula 3-14, Formula 3-15, Formula 3-16, Formula 3-17, Formula 3-18, Formula 3-19, Formula 3-20, Formula 3-21, Formula 3-22, Formula 3-23, Formula 3-24, Formula 3-25, Formula 3-26, Formula 3-27, Formula 3-28, Formula 3-29, Formula 3-30, Formula 3-31, Formula 3-32, Formula 3-33, Formula 3-34, Formula 3-35, Formula 3-36, Formula 3-37, Formula 3-38, Formula 3-39, Formula 3-40, Formula 3-41, Formula 3-42, Formula 3-43, Formula 3-44, Formula 3-45 and Formula 3-46:

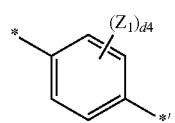

Formula 3-1

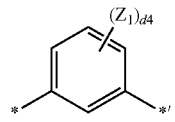

Formula 3-2

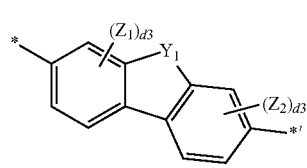

Formula 3-3

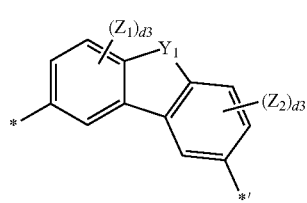

Formula 3-4

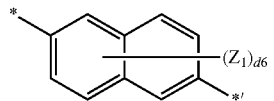

Formula 3-5

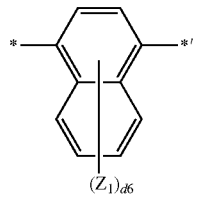

Formula 3-6

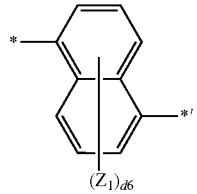

Formula 3-7

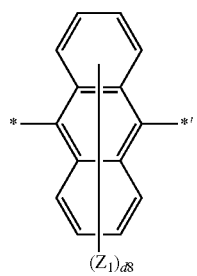

Formula 3-8

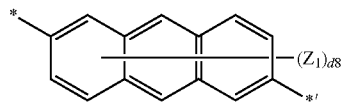

Formula 3-9

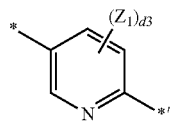

Formula 3-10

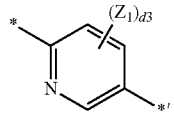

Formula 3-11

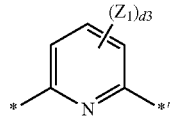

Formula 3-12

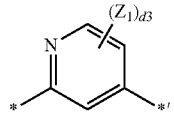

Formula 3-13

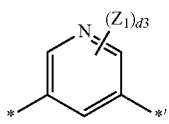
Formula 3-14
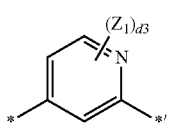
Formula 3-15
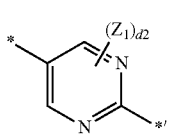
Formula 3-16
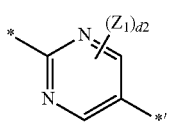
Formula 3-17
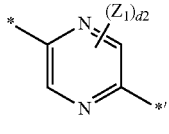
Formula 3-18
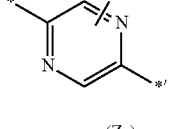
Formula 3-19
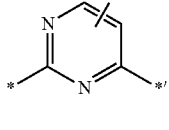
Formula 3-20
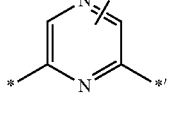
Formula 3-21
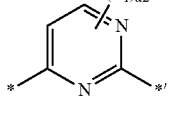
Formula 3-22
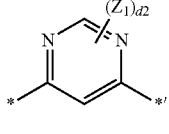
Formula 3-23
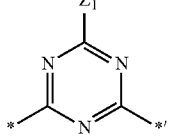
Formula 3-24
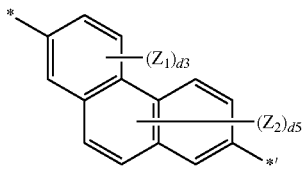
Formula 3-25
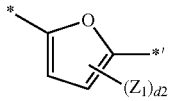
Formula 3-26
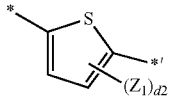
Formula 3-27
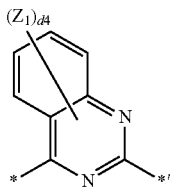
Formula 3-28
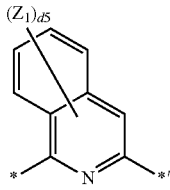
Formula 3-29
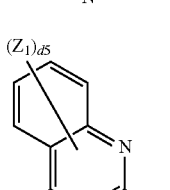
Formula 3-30
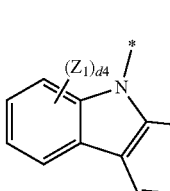
Formula 3-31
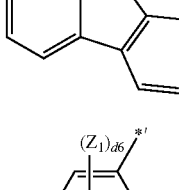
Formula 3-32
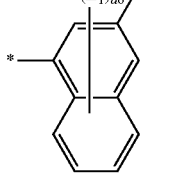
Formula 3-33

-continued
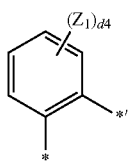
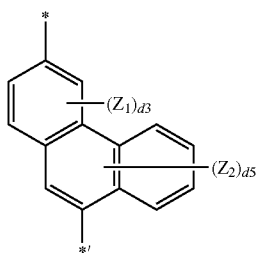
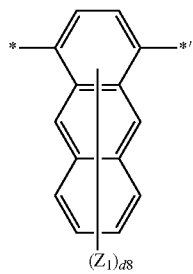
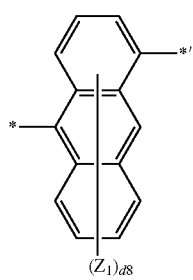
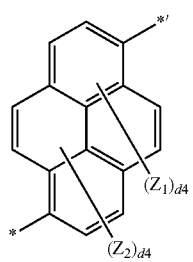
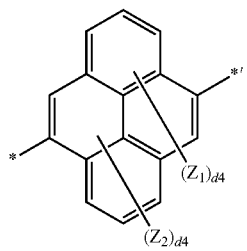
-continued
Formula 3-34
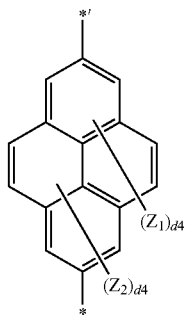
Formula 3-35
Formula 3-36
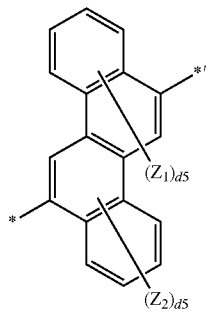
Formula 3-37
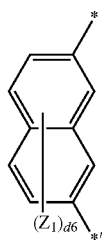
Formula 3-38
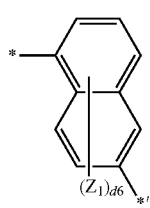
Formula 3-39
Formula 3-40
Formula 3-41
Formula 3-42
Formula 3-43
Formula 3-44
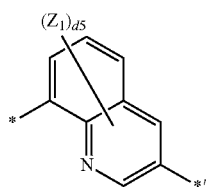
Formula 3-45

-continued

Formula 3-46

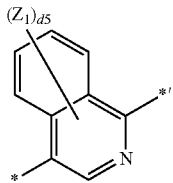

wherein:
Y$_1$ is selected from O, S, C(Z$_3$)(Z$_4$), N(Z$_5$) and Si(Z$_6$)(Z$_7$);
Z$_1$, Z$_2$, Z$_3$, Z$_4$, Z$_5$, Z$_6$ and Z$_7$ are each independently selected from hydrogen, deuterium, fluoro, chloro, bromo, iodo, hydroxy, cyano, nitro, amidino, hydrazino, hydrazono, C$_1$-C$_{20}$ alkyl, C$_1$-C$_{20}$ alkoxy, cyclopentyl, cyclohexyl, cycloheptyl, cyclopentenyl, cyclohexenyl, phenyl, biphenyl, terphenyl, pentalenyl, indenyl, naphthyl, azulenyl, indacenyl, acenaphthyl, fluorenyl, spiro-bifluorenyl, spiro-benzofluorene-fluorenyl, benzofluorenyl, dibenzofluorenyl, phenalenyl, phenanthrenyl, anthracenyl, fluoranthenyl, triphenylenyl, pyrenyl, chrysenyl, perylenyl, pentacenyl, pyrrolyl, thiophenyl, furanyl, silolyl, imidazolyl, pyrazolyl, thiazolyl, isothiazolyl, oxazolyl, isoxazolyl, pyridinyl, pyrazinyl, pyrimidinyl, pyridazinyl, indolyl, isoindolyl, indazolyl, purinyl, quinolinyl, isoquinolinyl, benzoquinolinyl, isoquinolinyl, phthalazinyl, naphthyridinyl, quinoxalinyl, benzoquinoxalinyl, quinazolinyl, benzoquinazolinyl, cinnolinyl, phenanthridinyl, acridinyl, phenanthrolinyl, phenazinyl, benzimidazolyl, benzofuranyl, benzothiophenyl, benzosilolyl, benzothiazolyl, isobenzothiazolyl, benzoxazolyl, isobenzoxazolyl, triazolyl, tetrazolyl, oxadiazolyl, triazinyl, carbazolyl, dibenzofuranyl, dibenzothiophenyl, dibenzosilolyl, benzocarbazolyl, a naphthobenzofuranyl, naphthobenzothiophenyl, naphthobenzosilolyl, dibenzocarbazolyl, dinaphthofuranyl, dinaphthothiophenyl, dinaphthosilolyl, thiadiazolyl, imidazopyridinyl, imidazopyrimidinyl, oxazolopyridinyl, thiazolopyridinyl, benzonaphthyridinyl, azafluorenyl, azaspiro-bifluorenyl, azacarbazolyl, azadibenzofuranyl, azadibenzothiophenyl, azadibenzosilolyl, indenopyrrolyl, indolopyrrolyl, indenocarbazolyl and indolocarbazolyl;
d2 is 1 or 2;
d3 is 1, 2 or 3;
d4 is 1, 2, 3 or 4;
d5 is 1, 2, 3, 4 or 5;
d6 is 1, 2, 3, 4, 5 or 6;
d8 is 1, 2, 3, 4, 5, 6, 7 or 8; and
* and *' are each independently a binding site to an adjacent atom.

6. The compound of claim 5, wherein L$_{11}$ is selected from Formula 3-2, Formula 3-12 and Formula 3-31.

7. The compound of claim 1, wherein:
L$_{11}$ is selected from phenylenyl, pentalenylenyl, indenylenyl, naphthylenyl, azulenylenyl, indacenylenyl, acenaphthylenyl, fluorenylenyl, spirobifluorenylenyl, spiro-benzofluorene-fluorenylenyl, benzofluorenylenyl, dibenzofluorenylenyl, phenalenylenyl, phenanthrenylenyl, anthracenylenyl, fluoranthenylenyl, triphenylenylenyl, pyrenylenyl, chrysenylenyl, perylenylenyl, pentacenylenyl, pyrrolylenyl, thiophenylenyl, furanylenyl, silolylenyl, imidazolylenyl, pyrazolylenyl, thiazolylenyl, isothiazolylenyl, oxazolylenyl, isoxazolylenyl, pyridinylenyl, pyrazinylenyl, pyrimidinylenyl, pyridazinylenyl, indolylenyl, isoindolylenyl, indazolylenyl, purinylenyl, guinolinylenyl, isoguinolinylenyl, benzoguinolinylenyl, benzoisoguinolinylenyl, phthalazinylenyl, naphthyridinylenyl, guinoxalinylenyl, guinazolinylenyl, cinnolinylenyl, phenanthridinylenyl, acridinylenyl, phenanthrolinylenyl, phenazinylenyl, benzimidazolylenyl, benzofuranylenyl, benzothiophenylenyl, benzosilolylenyl, benzothiazolylenyl, isobenzothiazolylenyl, benzoxazolylenyl, isobenzoxazolylenyl, triazolylenyl, tetrazolylenyl, oxadiazolylenyl, triazinylenyl, carbazolylenyl, dibenzofuranylenyl, dibenzothiophenylenyl, dibenzosilolylenyl, benzocarbazolylenyl, naphthobenzofuranylenyl, naphthobenzothiophenylenyl, naphthobenzosilolylenyl, dibenzocarbazolylenyl, dinaphthofuranylenyl, dinaphthothiophenylenyl, dinaphthosilolylenyl, thiadiazolylenyl, imidazopyridinylenyl, imidazopyrimidinylenyl, oxazolopyridinylenyl, thiazolopyridinylenyl, benzonaphthyridinylenyl, azafluorenylenyl, azaspiro-bifluorenylenyl, azacarbazolylenyl, azadibenzofuranylenyl, azadibenzothiophenylenyl, azadibenzosilolylenyl, indenopyrrolylenyl, indolopyrrolylenyl, indenocarbazolylenyl and indolocarbazolylenyl, each optionally substituted with at least one substituent selected from deuterium, fluoro, chloro, bromo, iodo, hydroxy, cyano, nitro, amidino, hydrazino, hydrazono, C$_1$-C$_{20}$ alkyl, C$_1$-C$_{20}$ alkoxy, C$_3$-C$_{10}$ cycloalkyl, C$_1$-C$_{10}$ heterocycloalkyl, C$_3$-C$_{10}$ cycloalkenyl, C$_1$-C$_{10}$ heterocycloalkenyl, C$_6$-C$_{20}$ aryl, C$_1$-C$_{20}$ heteroaryl, monovalent non-aromatic condensed polycyclyl, monovalent non-aromatic condensed heteropolycyclyl, methylphenyl, biphenyl and —Si(Q$_{31}$)(Q$_{32}$)(Q$_{33}$); and
Q$_{31}$, Q$_{32}$ and Q$_{33}$ are each independently selected from (i) C$_1$-C$_{10}$ alkyl and C$_1$-C$_{10}$ alkoxy; and (ii) phenyl, biphenyl, terphenyl, naphthyl, pyridinyl, pyrimidinyl, pyrazinyl, quinolinyl, isoquinolinyl, quinoxalinyl and quinazolinyl, each optionally substituted with at least one substituent selected from C$_1$-C$_{10}$ alkyl, C$_1$-C$_{10}$ alkoxy and phenyl.

8. The compound of claim 1, wherein:
Y is selected from C(R$_{17}$)(R$_{18}$) and Si(R$_{17}$)(R$_{18}$); and
R$_{17}$ and R$_{18}$ are each independently selected from hydrogen, deuterium, methyl, ethyl, n-propyl, isopropyl, n-butyl, isobutyl, sec-butyl and tert-butyl.

9. The compound of claim 1, wherein R$_{19}$ and R$_{20}$ are each independently selected from:
(i) hydrogen, deuterium, fluoro, chloro, bromo, iodo, hydroxy, cyano, nitro, amidino, hydrazino, hydrazono, C$_1$-C$_{20}$ alkyl and C$_1$-C$_{20}$ alkoxy; and
(ii) phenyl, biphenyl, terphenyl, pentalenyl, indenyl, naphthyl, azulenyl, indacenyl, acenaphthyl, fluorenyl, spiro-bifluorenyl, spiro-benzofluorene-fluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, thiophenyl, furanyl, carbazolyl, indolyl, isoindolyl, benzofuranyl, benzothiophenyl, dibenzofuranyl, dibenzothiophenyl, benzocarbazolyl, dibenzocarbazolyl, dibenzosilolyl, pyridinyl, pyrimidinyl, pyrazinyl, quinolinyl, isoquinolinyl, quinoxalinyl and quinazolinyl, each optionally substituted with at least one substituent selected from deuterium, fluoro, chloro, bromo, iodo, hydroxy, cyano, nitro, amidino, hydrazino, hydrazono, C$_1$-C$_{20}$ alkyl, C$_1$-C$_{20}$ alkoxy, cyclopentyl, cyclohexyl, cycloheptyl, cyclopentenyl, cyclohexenyl, phenyl, phenyl substituted with $C_1$-$C_{10}$ alkyl, phenyl substituted with fluoro, biphenyl, terphenyl, pentalenyl, indenyl, naphthyl, azulenyl, heptalenyl, indacenyl, acenaphthyl, fluorenyl, spiro-bifluorenyl, benzofluorenyl, dibenzofluorenyl, phenalenyl, phenanthrenyl, anthracenyl, fluoranthenyl, triphenylenyl, pyrenyl, chrysenyl, naphthacenyl, picenyl, perylenyl, pentaphenyl, hexacenyl, pentacenyl, rubicenyl, coronenyl, ovalenyl, thiophenyl, furanyl, carbazolyl, indolyl, isoindolyl, benzofuranyl, benzothiophenyl, dibenzofuranyl, dibenzothiophenyl, benzocarbazolyl, dibenzocarbazolyl, dibenzosilolyl, pyridinyl, pyrimidinyl, pyrazinyl, quinolinyl, isoquinolinyl, quinoxalinyl, —Si($Q_{31}$)($Q_{32}$)($Q_{33}$), —N($Q_{31}$)($Q_{32}$), —P(=O)($Q_1$)($Q_2$) and —S(=O)($Q_1$); and $Q_1$, $Q_2$, $Q_{31}$, $Q_{32}$ and $Q_{33}$ are each independently selected from $C_1$-$C_{10}$ alkyl, $C_1$-$C_{10}$ alkoxy, phenyl, biphenyl, terphenyl and naphthyl.

10. The compound of claim 1, wherein b19 and b20 are each independently 0, 1, 2, 3 or 4.

11. The compound of claim 1, wherein:
Formula I is represented by Formula 1-1:

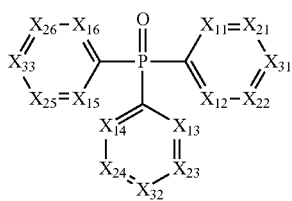

Formula 1-1 wherein:
$X_{11}$ is N or C($R_{11}$);
$X_{12}$ is N or C($R_{12}$);
$X_{13}$ is N or C($R_{13}$);
$X_{14}$ is N or C($R_{14}$);
$X_{15}$ is N or C($R_{15}$);
$X_{16}$ is N or C($R_{16}$);
$X_{21}$ is N or C($R_{21}$);
$X_{22}$ is N or C($R_{22}$);
$X_{23}$ is N or C($R_{23}$);
$X_{24}$ is N or C($R_{24}$);
$X_{25}$ is N or C($R_{25}$);
$X_{26}$ is N or C($R_{26}$);
$X_{31}$ is N or C($R_{31}$);
$X_{32}$ is N or C($R_{32}$);
$X_{33}$ is N or C($R_{33}$); and
$R_{11}$, $R_{12}$, $R_{13}$, $R_{14}$, $R_{15}$, $R_{16}$, $R_{21}$, $R_{22}$, $R_{23}$, $R_{24}$, $R_{25}$, $R_{26}$, $R_{31}$, $R_{32}$ and $R_{33}$ are each independently selected from hydrogen, deuterium, fluoro, chloro, bromo, iodo, hydroxy, cyano, nitro, amidino, hydrazino, hydrazono, $C_1$-$C_{60}$ alkyl, $C_2$-$C_{60}$ alkenyl, $C_2$-$C_{60}$ alkynyl $C_1$-$C_{60}$ alkoxy and Formula 2-1:

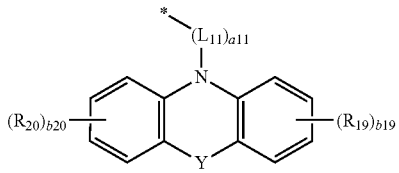

Formula 2-1 wherein *, a11, b19, b20, $L_{11}$, $R_{19}$ and $R_{20}$ are as defined in Formula 2;

with the proviso that:
(i) when $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{21}$ is C($R_{21}$), $X_{22}$ is C($R_{22}$), $X_{23}$ is C($R_{23}$), $X_{24}$ is C($R_{24}$), $X_{25}$ is C($R_{25}$), $X_{26}$ is C($R_{26}$), $X_{31}$ is C($R_{31}$), $X_{32}$ is C($R_{32}$) and $X_{33}$ is C($R_{33}$), at least two of $R_{11}$, $R_{12}$, $R_{21}$, $R_{22}$ and $R_{31}$ are Formula 2-1; or
(ii) when $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{21}$ is C($R_{21}$), $X_{22}$ is C($R_{22}$), $X_{23}$ is C($R_{23}$), $X_{24}$ is C($R_{24}$), $X_{25}$ is C($R_{25}$), $X_{26}$ is C($R_{26}$), $X_{31}$ is C($R_{31}$), $X_{32}$ is C($R_{32}$) and $X_{33}$ is C($R_{33}$), at least one of $R_{11}$, $R_{21}$, $R_{22}$ and $R_{31}$ and at least one of $R_{12}$, $R_{13}$, $R_{14}$, $R_{23}$, $R_{24}$ and $R_{32}$ is Formula 2-1.

12. The compound of claim 11, wherein:
at least one of $X_{11}$, $X_{12}$, $X_{13}$, $X_{14}$, $X_{15}$ and $X_{16}$ is N;
$X_{21}$ is C($R_{21}$);
$X_{22}$ is C($R_{22}$);
$X_{23}$ is C($R_{23}$);
$X_{24}$ is C($R_{24}$);
$X_{25}$ is C($R_{25}$); and
$X_{26}$ is C($R_{26}$);
with the proviso that at least one of $R_{21}$, $R_{22}$, $R_{23}$, $R_{24}$, $R_{25}$ and $R_{26}$ is Formula 2-1.

13. The compound of claim 12, wherein:
at least one of $X_{11}$, $X_{12}$, $X_{13}$, $X_{14}$, $X_{15}$ and $X_{16}$ is N;
$X_{31}$ is C($R_{31}$);
$X_{32}$ is C($R_{32}$); and
$X_{33}$ is C($R_{33}$);
with the proviso that at least one of $R_{31}$, $R_{32}$ and $R_{33}$ is Formula 2-1.

14. The compound of claim 12, wherein:
at least one of $X_{21}$, $X_{22}$, $X_{23}$, $X_{24}$, $X_{25}$ and $X_{26}$ is N;
$X_{31}$ is C($R_{31}$);
$X_{32}$ is C($R_{32}$); and
$X_{33}$ is C($R_{33}$);
with the proviso that at least one of $R_{31}$, $R_{32}$ and $R_{33}$ is Formula 2-1.

15. The compound of claim 12, wherein:
$X_{22}$ is N;
$X_{21}$ is C($R_{21}$);
$X_{25}$ is C($R_{25}$); and
$X_{26}$ is C($R_{26}$);
with the proviso that at least one of $R_{21}$, $R_{25}$ and $R_{26}$ is Formula 2-1.

16. The compound of claim 11, wherein:
at least one of $X_{31}$, $X_{32}$ and $X_{33}$ is N;
$X_{21}$ is C($R_{21}$);
$X_{22}$ is C($R_{22}$);
$X_{23}$ is C($R_{23}$);
$X_{24}$ is C($R_{24}$);
$X_{25}$ is C($R_{25}$); and
$X_{26}$ is C($R_{26}$);
with the proviso that at least one of $R_{21}$, $R_{22}$, $R_{23}$, $R_{24}$, $R_{25}$ and $R_{26}$ is Formula 2-1.

17. The compound of claim 1, wherein the compound is selected from the group consisting of:

-continued
26
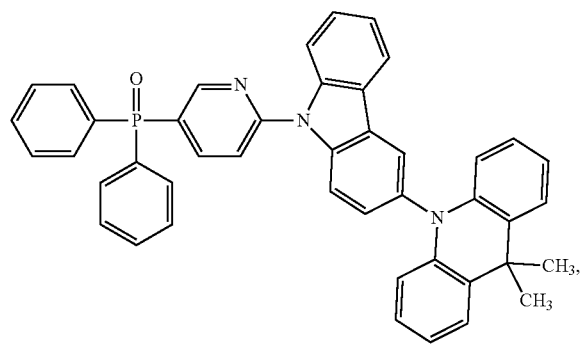
27
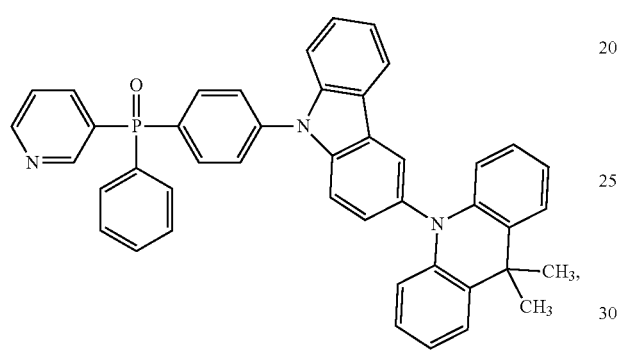
28
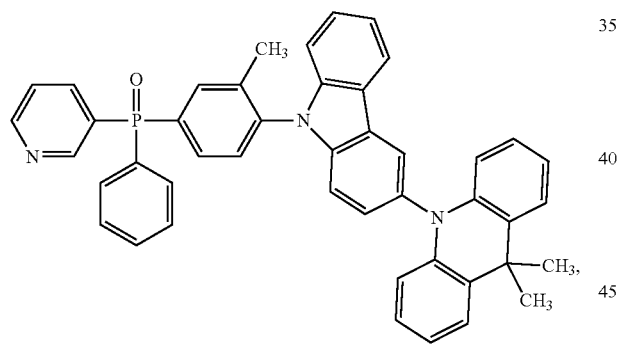
29
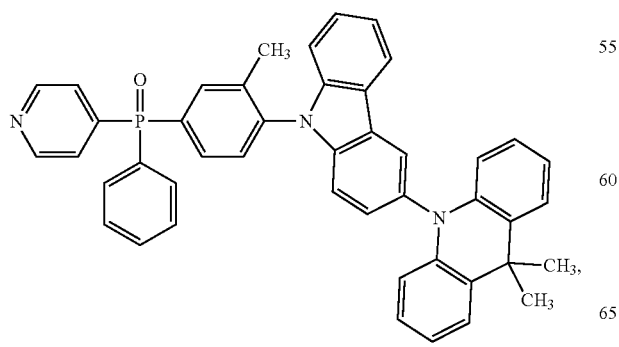
30
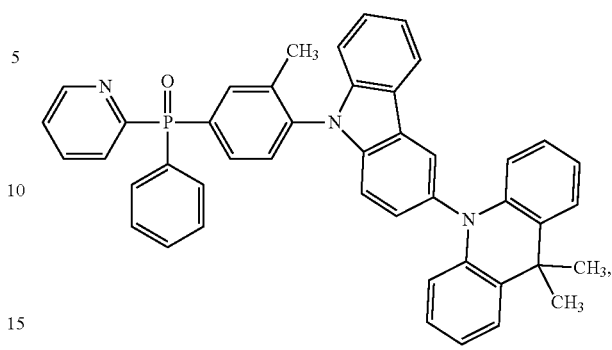
55
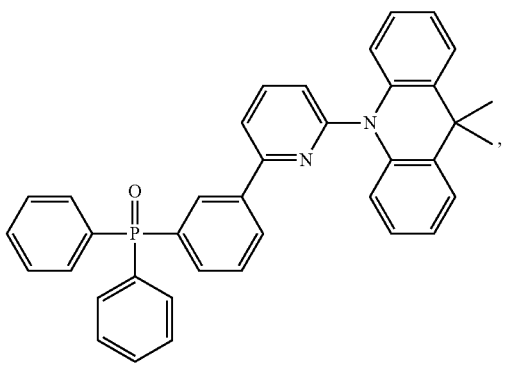
56
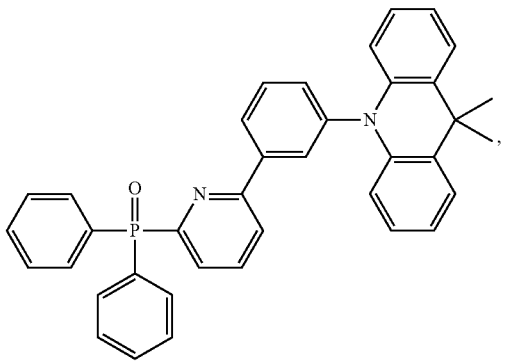
57
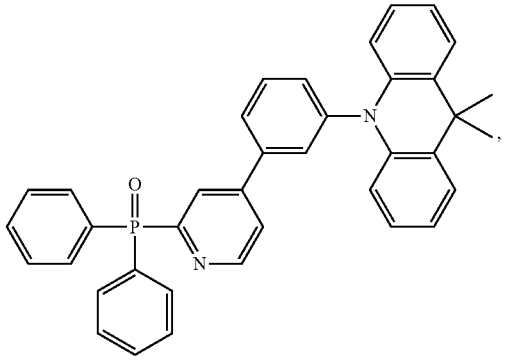

58
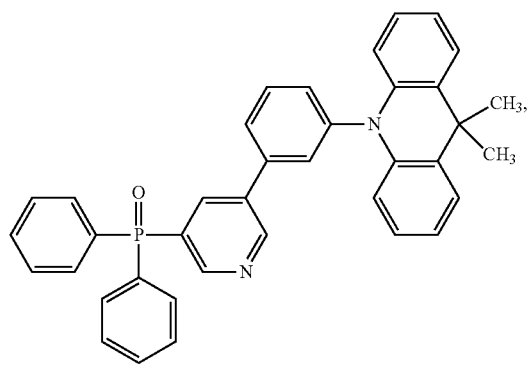
59
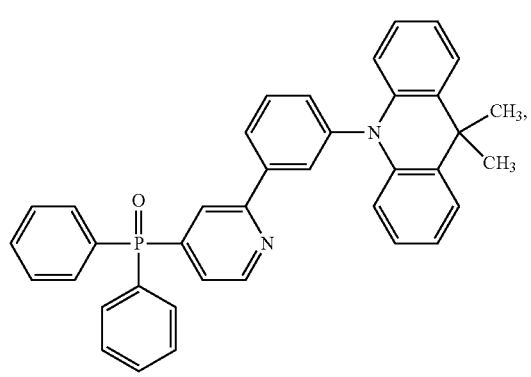
60
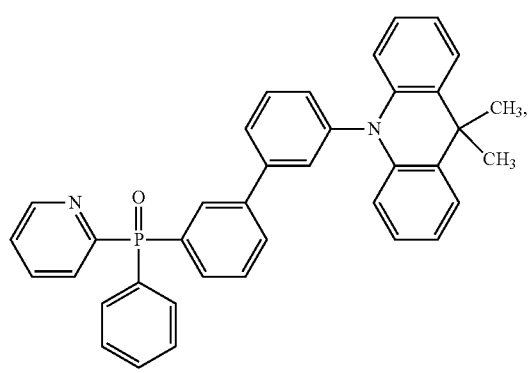
61
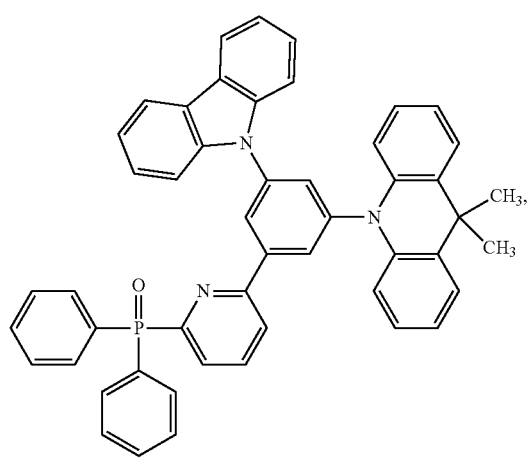
62
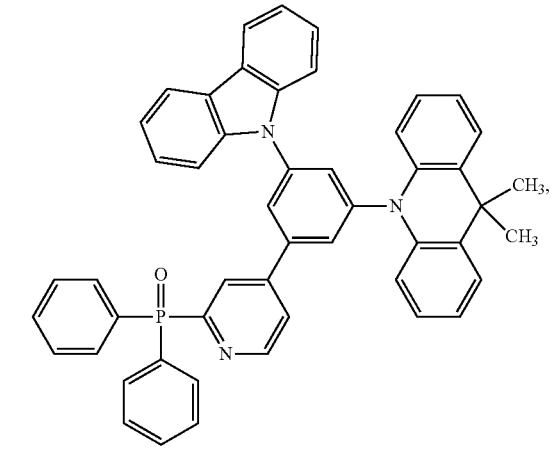
63
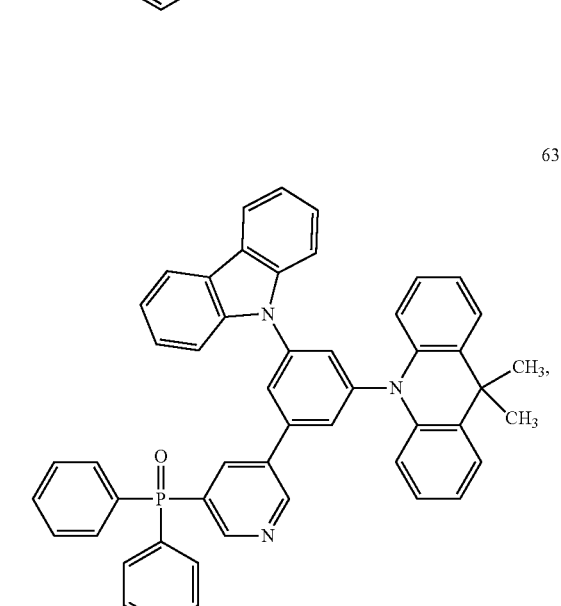
64
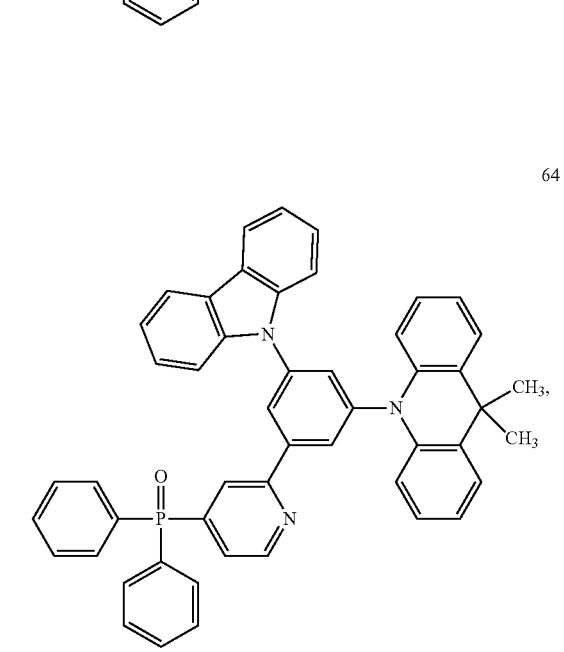

-continued

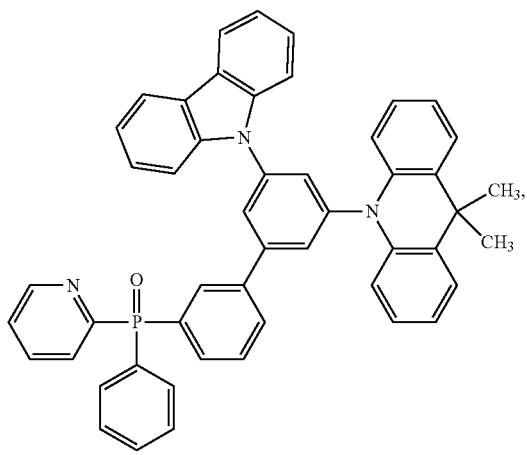
65

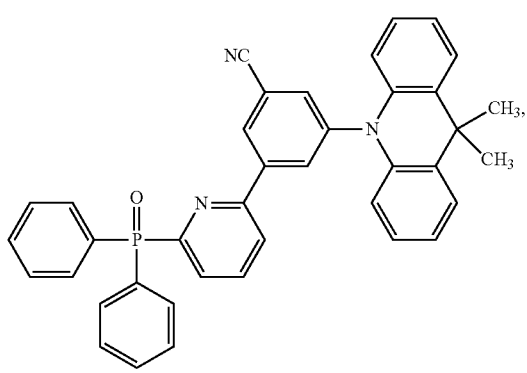
66

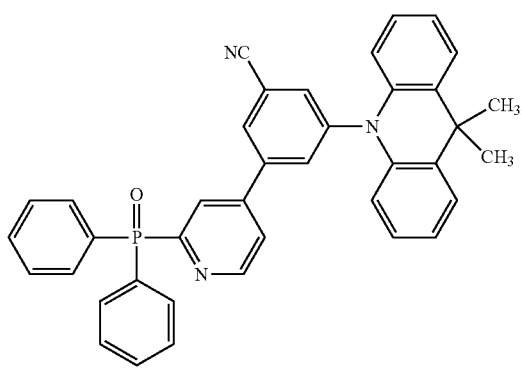
67

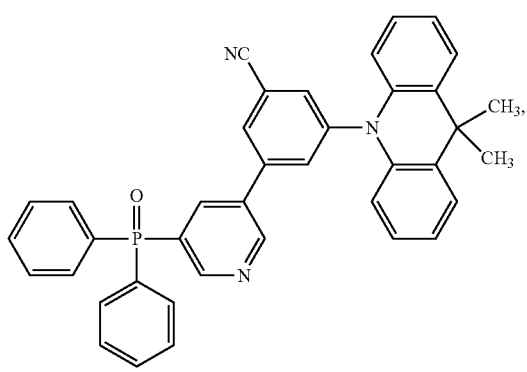
68

-continued

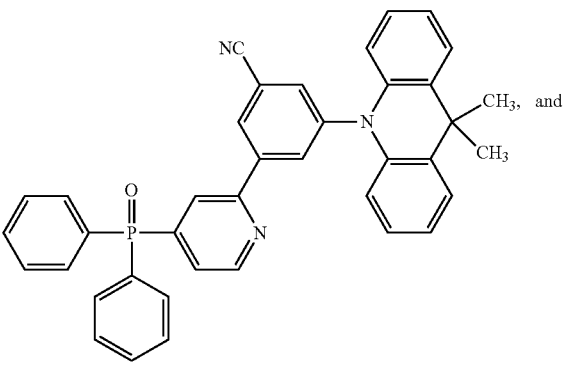
69

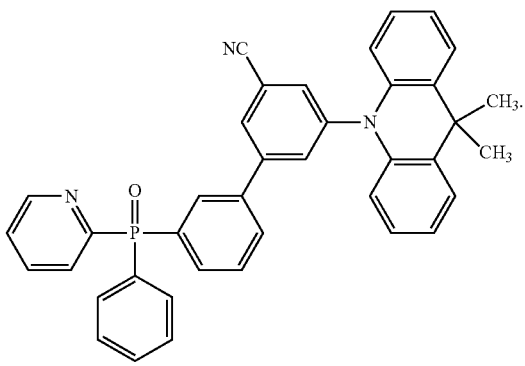
70 and

18. An organic light emitting device comprising:
(i) a first electrode;
(ii) a second electrode facing the first electrode; and
(iii) an organic layer between the first electrode and the second electrode,
wherein the organic layer comprises an emission layer and the compound of claim 1.

19. The organic light emitting device of claim 18, wherein:
(i) the emission layer comprises a host and a dopant; and
(ii) at least one selected from the host and the dopant comprises the compound of claim 1.

* * * * *